(12) United States Patent
Lim et al.

(10) Patent No.: US 7,339,091 B2
(45) Date of Patent: Mar. 4, 2008

(54) **RECOMBINANT *BACILLUS* PHYTASES AND USES THEREOF**

(75) Inventors: Boon Leong Lim, Hong Kong (CN); Wing Kin Yip, Hong Kong (CN)

(73) Assignee: The University of Hong Kong, Hong Kong (HK)

( * ) Notice: Subject to any disclaimer, the term of this patent is extended or adjusted under 35 U.S.C. 154(b) by 325 days.

(21) Appl. No.: 10/299,641

(22) Filed: Nov. 19, 2002

(65) Prior Publication Data

US 2007/0277257 A1 Nov. 29, 2007

Related U.S. Application Data

(60) Provisional application No. 60/332,060, filed on Nov. 21, 2001.

(51) Int. Cl.
- C12N 15/29 (2006.01)
- C12N 15/82 (2006.01)
- C12N 5/04 (2006.01)
- A01H 4/00 (2006.01)
- A01H 5/00 (2006.01)

(52) U.S. Cl. .................. 800/278; 800/298; 800/306; 800/322; 800/293; 800/292; 800/294; 435/320.1; 435/419; 435/430

(58) Field of Classification Search ............. 435/320.1, 435/419, 468; 536/23.1, 23.6; 800/278, 800/298, 306, 320.2, 322
See application file for complete search history.

(56) References Cited

U.S. PATENT DOCUMENTS 5,593,963 A * 1/1997 Van Ooijen et al. .......... 514/12

OTHER PUBLICATIONS

Wyss et al (1999, Applied and Environmental Microbiology 65(2):367-373).*
Fourgoux-Nicol et al (1999, Plant Molecular Biology 40 :857-872).*
Kerovuo et al (1998, Applied and Environmental Microbiology 64(6):2079-2085).*
Berka, R.M., Rey M.W., Brown K.M., Byun T, Klotz A.V. (1998) Molecular characterization and expression of a phytase gene from the thermophilic fungus *Fusarium venenatum*. *Applied and Environmental Microbiology.* 64(11), 4423-4427.
Craxton A., Caffrey J.J., Burkhart W., Safrany S.T., Shears S.B. (1997) Molecular cloning and expression of a rat hepatic multiple inositol polyphosphate phosphatase. *Biochemistry Journal*, 328, 75-81.
Dassa J., Marck C. and Boquet P.L. (1990) The complete Nucleotide Sequence of the *Escherichia coli* gene *appA* reveals significant homology between pH 2.5 acid phosphatase and glucose-1-phosphtase, *Journal of Bacteriology 172*(9), 5497-5500.
Engelen A.J., Heeft F.C., Randsdorp P.H.G., Smit E.L.C. (1994) Simple and Rapid Determination of Phytase Activity. *Journal of AOAC International 77*(3), 760-764.

Greiner R., Haller, E., Konietzny U., Jany K.D. (1997) Purification and characterization of a phytase from *Klebsiella terrigena*. *Archives of Biochemistry and Biophysics.* 341(2), 201-206.
Han Y. Wilson, D.B., Lei X.G. (1999) Expression of an *Asperigillus niger* phytase gene (*phyA*) in *Saccharomyces cerevisiae*. *Applied and Environmental Microbiology.* 65(5), 1915-1928.
Han Y & Lei X.G. (1999) Role of glycosylation in the functional expression of an *Asperigillus* phytase (*phyA*) in *Pichia pastoris*. *Archives of Biochemistry and Biophysics.* 364(1), 83-90.
Hiei Y, Ohta S, Komari T, Kumashiro T. Efficient transformation of rice (Oryza sativa L.) mediated by Agrobacterium and sequence analysis of the boundaries of the T-DNA. Plant J, 1994, 6:271-282.
Höfgen R, Willimitzer L (1988) Storage of competent cells for Agrobacterium transformation. Nucleic Acids Res 16:9877.
Kerovuo J., Laurarus M., Nurminen P., Kalkkinen N., Apajalahti J. (1998) Isolation, characterization, molecular gene cloning, and sequencing of a novel phytase from *Bacillus subtilis, Applied and Environmental Microbiology.* 64(6), 2079-2085.
Kim Y.O., Lee J.K., Kim H.K., Yu J.H., Oh T.K. (1998) Cloning of the thermostable phytase gene (phy) from *Bacillus* sp. DS11 and its overexpression in *Escherichia coli*. *FEMS Microbiology Letters*, 162, 182-191.
Leung Y.C. & Erington J. (1995) Characterization of an insertion in the phage f105 genome that blocks host *Bacillus subtilis* lysis and provides strong expression of heterologous genes. *Gene*, 154, 1-6.
Maugenest S., Martinez I & Lescure A. (1997) Cloning and characterization of a cDNA encoding a maize seedling phytase. *Biochemistry Journal*, 322, 511-517.
Mayer A.F., Hellmuth, K., Schlieker H., Ulibarri R.L., Oertel S., Dahlems U., Strasser A.W.M. Strasser, Loon A.P.G.M. (1998) An expression eyetem matures: A highly efficient and cost-effective process for phytase production by recombinant strains of *Hansenula polymorpha*. *Biotechnology and Bioengineering.* 63(3), 373-381.
Osburne M.S., Craig R. J. and Rothstein D. M. (1985) Thermoniducible transcription system for *Bacillus subtilis* that utilizes control elements from temperate phage f 105. *J. of Bacteriology 16*, 1101-1108.
Ostanin K., Harms E.H., Stevis P.E., Kuciel R., Zhou M.M., Van Etten R.L. (1992) Overpression, site-directed mutagenesis, and mechanism of *Escherichia coli* and phosphatase. *Journal of Bacteriology*, 267(32), 22830-22836.

(Continued)

*Primary Examiner*—Stuart F. Baum
(74) *Attorney, Agent, or Firm*—Dickstein Shapiro LLP

(57) ABSTRACT

In this invention, two phytase genes from two generally-regarded-as-safe microorganisms, *Bacillus licheniformis* and *Bacillus subtilis* 168, were cloned and characterized. A process for phytase enzyme over-expression and purification was also developed. The enzymes have molecular weight of about 48 kilodaltons and showed extracellular phytate-hydrolyzing activities. The recombinant enzyme can be used to enhance phytase utilization in various commercial areas, including preparation of animal feed and transgenic plants that have increased growth rates for maturity, flowering and fruiting.

28 Claims, 23 Drawing Sheets
(3 of 23 Drawing Sheet(s) Filed in Color)

OTHER PUBLICATIONS

Pasamontes L, Haiker M, Wyss M, Tessier M, Loon A.P.G. (1997) Gene cloning, purification, and characterization of a heat-stable phytase from the fungus *Aspergillus fumigantus*. *Applied and Environmental Microbiology.* 63(5), 1696-1700.

Pen J. Verwored T.C., Hoekema A. (1993) Phytase-containing transgenic seeds as novel feed additive for improved phosphorus utilization. *Bio/Technology*, 11, 811-814.

Phillippy B.Q. and Mullaney E.J. (1997) Expression of an *Aspergillus niger* phytase (*phyA*) in *Escherichia coli*. *Journal of Agricultural Food Chemistry*, 45, 3337-3342.

Powar V.K. and Jagannathan V. (1982) Purification and properties of Phytase-Specific Phosphatase from *Bacillus substilis*. *Journal of Bacteriology.* 151(3), 1102-1108.

Rashid H, Yokoi S, Toriyama K, Hinata K (1996) Transgenic plant production mediated by *Agrobacterium* in Indica rice. Plant cell Rep, 15:727-730.

Reddy N. R., Pierson M. D., Sathe S. K. & Salunkhe D. K. (1989) Phytases in legumes and cereals. *CRC Press, Inc.*, Boca Raton, Florida.

Rodriguez E., Mullaney E.J., Lei X.G. (2000) Expression of the *Aspergillus fumigatus* phytase gene in *Pichia pastoris* and characterization of the recombinant enzyme. *Biochemical and Biophysical Research Communications*, 268, 373-378.

Rodriguez E., Han Y. and Lei X.G. (1999) Cloning, Sequencing, and Expression of an *Escherichia coli* Acid Phosphatase/phytase Gene (*appA2*) Isolated from Pig Colon. *Biochemical and Biophysical Research Communications*, 257, 117-123.

Thornwwell S. J., Ease A.K., Errington J. (1993) An efficient expression and secretion system based on *Bacillus subtilis* phage f105 and its use for the production of *B. cereus* β-lactarnase I. *Gene*, 133, 47-53.

Ullah A.H., Cummins B.J. (1988) *Aspergillus ficuum* extracellular pH 6.0 optimum acid phosphatase: purification, N-terminal amino acid sequence, and biochemical characterization. *Preparative Biochemistry*, 18(1), 37-65.

Ullah A.H.J., Sethumadhavan K., Mullaney E.J. (1999) Characterization of recombinant fungal phytase (*phyA*) expressed in tobacco leaves. *Biochemical and Biophysical Research Communications*, 264, 201-206.

Chu C-C, Wang J-J, Sun J-S, Xu Z, Yin G-C, Zhu Z-Y, Bi F-Y (1975), Establishment of an efficient medium for anther culture of rice through comparative experiments on the nitrogen sources. Sci Sin, 18:659-668.

* cited by examiner

```
ttttacccga  tggatgggga  cttaaacgaa  cttgcgtttg  agatatacat  tccgattcat  tgagagatag  cgatgttaaa
ggcagccccc  ggaaaaaatt  ccggggttt   tctttgggtt  tcgtactcta  gagtatcggc  ggtctttttt  agccatcact
tttaacaaaa  gtttacatac  cctcaaatga  taattttcat  tggtttgcta  ggataaatgt  tatgaaaagg  agttaatat
ATGAACTTTT  ACAAAACGCT  CGCTTTATCA  ACACTCGCAG  CATCCTTATG  GTCTCCCTCA  TGGAGCAGTC  TCCCCATAA
CGAAGCTGCG  GCTCACAAAG  AATTCACGGT  GACTGCCGAT  GCAGAGACAG  AGCCGGTGGA  TACCCCTGAC  GACGCGGCAG
ATGACCCGGC  GATTTGGGTT  CATCCGAAGC  AGCCTGAAAA  AAGCAGGCTC  ATCACCACAA  ACAAAAAGTC  GGGCTTAATC
GTCTATGATT  TGAAGGGAAA  ACAGCTTGCG  GCCTATCCGT  TTGGCAAATT  AAACAATGTC  GACCTGCGCT  ACAATTTTCC
GCTCGATGGC  AAAAAAATTG  ATATTGCCGG  CGGTCAGACG  CGGTCAGACG  GCAAAAACAC  GGTTGAAATT  TACGCCTTTG
ACGGCGAAAA  AAGCAAGCTG  AAGAACATCG  TCAATCCTCA  AAAACCTATT  CAAACCGATA  TCCAGGAGGT  ATATGGCTTC
AGCCTGTATC  ACAGCCAGAA  AACCGGCAAG  TTCTACGCCA  TGGTGACCGG  AAAGAACGGA  GAATTCGAGC  AATATGAACT
GTTTGACAAC  GGAAAAGGAC  AAGTCGAGGG  CAAAAAGTC   CGCTCATTCA  AATGAGCTC   TCAAACAGAA  GGGCTTGCGG
CAGATGATGA  ATACGGCAAA  ATGTACATCG  CCGAAGAAGA  CGTTGCGATT  TGGTCTTTCA  CGCCGAGCC   GGACGGCGGA
GATAAAGGAA  AAATCGTCGA  TCGTGCCGAC  GGACCGCATC  TAACTTCTGA  TATTGAAGGG  CTGACGATTT  ACTACGAGA
AGACGGAGAA  GGGTATTTGA  TCGCGTCCAG  TCAGGCGAT   AACCGCTATG  CCATCTATGA  CCGGCGGG    AAAACGACT
ACGTCACTGC  TTTTTCAATT  GAGGACGGCA  AAGAAATCGA  CGGGACAAGC  GATACCGATG  GAATCGACGT  CATCGGCTTC
GGCCTTCGGC  AAACATATCC  ATACGGCATC  TTTGTCGCCC  AAGACGGCGA  AAATACGACAA  AATGACGAC  CGGCCAATCA
GAACTTCAAA  ATTGTCTCCT  GGGAAAAAT  CGCCGACGCG  CTGGACGACA  AACCTGATAT  CGATGATCAG  GTCGATCCCC
GAAAACTGAA  AACCGAGCC   AAATAAGGAC
```

*Fig. 1A*

```
MNFYKTLALS TLAASLWSPS WSSLPHNEAA AHKEFTVTAD AETEPVDTPD DAADDPAIWV HPKQPEKSRL ITTNKKSGLI
VYDLKGKQLA AYPFGKLNNV DLRYNFPLDG KKIDIAGASN RSDGKNTVEI YAFDGEKSKL KNIVNPQKPI QTDIQEVYGF
SLYHSQKTGK FYAMVTGKNG EFEQYELFDN GKGQVEGKKV RSFKMSSQTE GLAADDEYGK MYIAEEDVAI WSFSAEPDGG
DKGKIVDRAD GPHLTSDIEG LTIYYGEDGE GYLIASSQGD NRYAIYDRRG KNDYVTAFSI EDGKEIDGTS DTDGIDVIGF
GLGKTYPYGI FVAQDGENTE NGQPANQNFK IVSWEKIADA LDDKPDIDDQ VDPRKLKNRA K
```

*Fig. 1B*

```
gagtcagaaa ccctataaaa aaaggttcat tttcctcacg gtaatcacct gtatatattt tacaatagta gtgttagtga
taaagagga gggtaccaaA TGAAGGTTCC AAAAACAATG CTGCTAAGCA CTGCCGCGGG TTTATTGCTT AGCCTGACAG
CAACCTCGGT GTCGGCTCAT TATGTGAATG AGGAACATCA TTTCAAAGTG ACTGCACACA CGGAGACAGA TCCGGTCGCA
TCTGGCGATG GTCGCAGCAGA TGACCCGGCC ATTTGGGTTC ATGAAAAACA CCCGAAAAA AGCAAGTTGA TTACAACAAA
TAAGAAGTCA GGGCTCGTTG TGTATGATTT AGACGGAAAA CAGCTTCATT CTTATGAGTT TGGCAAGCTC AATAATGTCG
ATCTGCGCTA TGATTTTCCA TTGAACGGCG AAAAAATTGA TATTGCTGCC GCATCCAACC GGTCCGAAGG AAAAAATACA
ATTGAAGTAT ATGCAATAGA CGGGATAAA GGAAAATTGA AAAGCATTAC AGATCCGAAC CATCCTATTT CCACCAATAT
TTCTGAGGTT TATGGATTCA GCTTGTATCA CAGCCAGAAA ACAGGAGCAT TTTACGCATT AGTGACAGGC AAACAAGGGG
AATTTGAGCA GTATGAAATT GTTGATGGTG GAAAGGGTTA TGTAACAGGG AAAAAGGTGC GTGAATTTAA GTTGAATTCT
CAGACCGAAG GCCTTGTTGC GGATGATGAG TACGGAAACC TATACATAGC AGAGGAAGAT GAGGCCATCT GGAAATTTAA
CGCTGAGCCC GGCGAGGGT CAAAGGGGCA GGTTGTTGAC CGTGCGACAG GAGATCATTT GACAGCTGAT ATTGAAGGAC
TGACAATCTA TTATGCACCA AATGGCAAAG GATATCTCAT GGCTTCAAGT CAAGAAATA ACAGCTATGC AATGTATGAA
CGGCAGGGA AAAATCGCTA TGTAGCCAAC TTTGAGATTA CAGATGGCGA GAAGATAGAC GGTACTAGTG ACACGGATGG
TATTGATGTT CTCGGTTTCG GACTTGGCCC AAAATATCCG TACGGGATTT TTGTGGCGCA GGACGGCGAA AATATTGATA
ACGGACAAGC CGTCAATCAA AATTTCAAAA TTGTATCGTG GGAACAAATT GCACAGCATC TCGGCGAAAT GCCTGATCTT
CATAAACAGG TAAATCCGAG GAAGCTGAAA GACCGTTCTG ACGGCTAGaa tagaaagcag cttgtgcagc tgcttttttc
tatgaataaa aaaatcgttc atagcaatga acgattttt aagaaagcgc cagatgaatc gctttagtt ttgcaggaag
ctcatcaaac gtaaatgcgg
```

*Fig. 2A*

```
MKVPKTMLLS TAAGLLLSLT ATSVSAHYVN EEHHFKVTAH TETDPVASGD DAADDPAIWV HEKHPEKSKL ITTNKKSGLV
VYDLDGKQLH SYEFGKLNNV DLRYDFPLNG EKIDIAAASN RSEGKNTIEV YAIDGDKGKL KSITDPNHPI STNISEVYGF
SLYHSQKTGA FYALVTGKQG EFEQYEIVDG GKGYVTGKKV REFKLNSQTE GLVADDEYGN LYIAEEDEAI WKFNAEPGGG
SKGQVVDRAT GDHLTADIEG LTIYYAPNGK GYLMASSQGN NSYAMYERQG KNRYVANFEI TDGEKIDGTS DTDGIDVLGF
GLGPKYPYGI FVAQDGENID NGQAVNQNFK IVSWEQIAQH LGEMPDLHKQ VNPRKLKDRS DG
```

Vector

0134

0042

0043

0042

0134

Vector

RECOMBINANT *BACILLUS* PHYTASES AND USES THEREOF

This application is entitled to and claims priority benefit to U.S. provisional application Ser. No. 60/332,060, filed Nov. 21, 2001, which is incorporated herein by reference in its entirety.

INTRODUCTION

The present invention relates to phytase genes from two generally-regarded-as-safe (GRAS) microorganisms, *Bacillus licheniformis* and *Bacillus subtilis* 168, and their respectively encoded protein products, as well as fragments, derivatives, analogs, and variants thereof. Methods for production and purification of the phytase enzymes, derivatives, analogs, variants and antibodies are also provided. The uses of these phytases in animal feed are also provided. The invention also provides plants transgenic for these two phytases active at neutral pH ("neutral phytases") and other neutral phytases. Such transgenic plants exhibit enhanced growth, flowering, and fruit growth.

BACKGROUND OF INVENTION

Phytate, the salt form of phytic acid (myo-inositol 1,2,3,4,5,6-hexakis dihydrogen phosphate), accounts for over 80% of total phosphorus in cereals and legumes, which, together with oilseed crops, are grown on over 90% of the world's harvested area (Reddy N. R., Pierson M. D., Sathe S. K. and Salunkhe D. K., 1989, *Phytases in legumes and cereals*. CRC Press, Inc., Boca Raton, Fla.). Although phytate is a storage form of phosphorus, phosphorus is not readily available to animals or plants, as a specific enzyme is required for the hydrolysis of phytate into inorganic phosphate.

Phytase, the enzyme that prefers phytate as its substrate, increases the availability of utilizable phosphorus by catalyzing the conversion of phytate into inorganic phosphate and myo-inositol phosphate and releasing phosphate to be utilized by animals and plants.

Over-expression of the phytase enzyme has been a long term and competitive topic in the biotechnology and enzyme production industry, due to the economical and environmental importance of the enzyme. Researchers have found ways to over-express the enzyme with the highest activity and the least number of purification steps to be carried out. Earlier studies on phytase expression were concerned with the extraction and production of the enzyme from fungal sources, which, until now, have been the only known source of for animal feed.

As early as in the 1980s, phytase was expressed in the extracellular medium from *Aspergillus ficuum/niger* (Ullah A. H. and Cummins B. J., 1988, *Aspergillus ficuum* extracellular pH 6.0 optimum acid phosphatase: purification, N-terminal amino acid sequence, and biochemical characterization. *Preparative Biochemistry*, 18(1):37-65). The enzyme was broadly studied by Ullah et al. in the same year. Until now, phytase from *A. niger* has been the most important commercial phytase. In the 1990s, the production of the enzyme was improved by a new biotechnology, i.e., expressing a recombinant protein in foreign strains, which was found promising in improving the yield of heterologous proteins. Fungal strains including *Fusarium venenatum* (Berka, R. M., Rey M. W, Brown K. M., Byun T, and Klotz A. V., 1998, Molecular characterization and expression of a phytase gene from the thermophilic fungus *Fusarium venenatum*. *Applied and Environmental Microbiology*, 64(11):4423-4427), *Aspergillus niger* and other *Aspergillus* species (Pasamontes L, Haiker M, Wyss M, Tessier M, and Loon A. P. G., 1997, Gene cloning, purification, and characterization of a heat-stable phytase from the fungus *Aspergillus fumigatus*. *Applied and Environmental Microbiology*, 63(5): 1696-1700; U.S. Pat. No. 5,830,733; U.S. Pat. No. 5,436,156; and U.S. Pat. No. 6,153,418); *Klebsiella terrigena* (Greiner R., Haller, E., Konietzny U., and Jany K. D., 1997, Purification and characterization of a phytase from *Klebsiella terrigena*. *Archives of Biochemistry and Biophysics*, 341(2):201-206); *Thermomyces* species (U.S. Pat. No. 5,866,118); and *Schwanniomyces occidentalis* (U.S. Pat. No. 5,840,561) have been reported to express heterogeneous phytase in significant amounts with appreciable activities. Many attempts to enzymatically hydrolyze phytate have been made which resulted in moderate improvements to the nutritional value of feed and a decrease in the amount of phosphorus excreted by animals, an environment benefit (Pen J., Verwoerd T. C., and Hoekema A., 1993, Phytase-containing transgenic seeds as novel feed additive for improved phosphorus utilization. *Bio/Technology*, 11:811-814).

While the enzyme production in fungi continues, other research groups have moved their focus to expressing phytase in yeast (Mayer A. F., Hellmuth, K., Schlieker H., Ulibarri R. L., Oertel S., Dahlems U., Strasser A. W. M. Strasser, and Loon A. P. G. M., 1998, An expression system matures: A highly efficient and cost-effective process for phytase production by recombinant strains of *Hansenula polymorpha*. *Biotechnology and Bioengineering*, 63(3):373-381; Han Y., Wilson, D. B., and Lei X. G., 1999, Expression of an *Aspergillus* niger phytase gene (phyA) in *Saccharomyces cerevisiae*. *Applied and Environmental Microbiology*. 65(5):1915-1918; Han Y and Lei X. G., 1999, Role of glycosylation in the functional expression of an *Asperigillus* phytase (phyA) in *Pichia pastoris*. *Archives of Biochemistry and Biophysics*, 364(1):83-90; Rodriguez E., Mullaney E. J., and Lei X. G., 2000, Expression of the *Aspergillus fumigatus* phytase gene in *Pichia pastoris* and characterization of the recombinant enzyme. *Biochemical and Biophysical Research Communications*, 268:373-378), plants (Ullah A. H. J., Sethumadhavan K., Mullaney E. J., 1999, Characterization of recombinant fungal phytase (phyA) expressed in tobacco leaves. Biochemical and Biophysical Research Communications, 264:201-206), and the enteric bacteria *Escherichia coli* (*E. coli*) (Dassa J., Marck C. and Boquet P. L., 1990, The complete Nucleotide Sequence of the *Escherichia coli* gene appA reveals significant homology between pH 2.5 acid phosphatase and glucose-1-phosphtase. *Journal of Bacteriology*, 172(9):5497-5500; Ostanin K., Harms E. H., Stevis P. E., Kuciel R., Zhou M. M., and Van Etten R. L., 1992, Overexpression, site-directed mutagenesis, and mechanism of *Escherichia coli* acid phosphatase. *Journal of Bacteriology*, 267(32):22830-22836; and Rodriguez E., Han Y. and Lei X. G., 1999, Cloning, Sequencing, and Expression of an *Escherichia coli* Acid Phosphatase/Phytase Gene (appA2) Isolated from Pig Colon. *Biochemical and Biophysical Research Communications*, 257:117-123). Other phytase sources from plants (Maugenest S., Martinez I and Lescure A, 1997, Cloning and characterization of a cDNA encoding a maize seedling phytase. *Biochemistry Journal*, 322:511-517) and mammals (Craxton A., Caffrey J. J., Burkhart W., Safrany S. T., and Shears S. B., 1997, Molecular cloning and expression of a rat hepatic multiple inositol polyphosphate phosphatase. *Biochemistry Journal*, 328:75-81) were also studied.

Several phytase genes in *E. coli* and *Lactobacillus* including EcAP (Ostanin K., Harms E. H., Stevis P. E., Kuciel R., Zhou M. M., and Van Etten R. L., 1992, Overexpression, site-directed mutagenesis, and mechanism of *Escherichia coli* acid phosphatase. *Journal of Bacteriology*, 267(32): 22830-22836), appA (Dassa J., Marck C. and Boquet P. L., 1990, The complete Nucleotide Sequence of the *Escherichia coli* gene appA reveals significant homology between pH 2.5 acid phosphatase and glucose-1-phosphatase. *Journal of Bacteriology*, 172(9):5497-5500), appA2 (Rodriguez E., Han Y. and Lei X. G., 1999, Cloning, Sequencing, and Expression of an *Escherichia coli* Acid Phosphatase/Phytase Gene (appA2) Isolated from Pig Colon. *Biochemical and Biophysical Research Communications*, 257:117-123), and *Lactobacillus plantarum* (Zamudio et al., 2001, *Lactobacillus plantarum* phytase activity is due to non-specific acid phosphatase, *Lett. App. Microbiol.* 32:181-184), were identified and all were characterized as acid phosphatases with optimal enzyme activity at pH lower than 6.0. Other *E. coli*-derived phytases are disclosed in U.S. Pat. Nos. 6,183,740 and 6,190,897.

Although fungal and *E. coli* phytases have been expressed to significant amounts, the purification procedures for these phytases have been shown to be complicated and, in addition, these heterologously expressed enzymes often do not fold properly. For example, *E. coli* was found unable to express an active phytase enzyme originating from *A. niger*, because *E. coli* produces a non-glycosylated, intracellular inclusion protein that has a large molecular weight (Phillippy B. Q. and Mullaney E. J., 1997, Expression of an *Aspergillus niger* phytase (phyA) in *Escherichia coli*. *Journal of Agricultural Food Chemistry*, 45:3337-3342). Moreover, *E. coli* is an enteric bacterium that carries a risk of infecting animal gastro-intestinal tracts.

Several *Bacillus* strains are known to be GRAS bacterial strains. Genes encoding phytases have been cloned from *Bacillus subtilis* strains, VTT E-68013 (phyC; Kerovuo J., Laurarus M., Nurminen P., Kalkkinen N., and Apajalahti J., 1998, Isolation, characterization, molecular gene cloning, and sequencing of a novel phytase from *Bacillus subtilis*. *Applied and Environmental Microbiology*, 64(6):2079-2085, which is hereby incorporated by reference in its entirety) and DS11 (phyK; Kim Y. O., Lee J. K., Kim H. K., Yu J. H., and Oh T. K., 1998, Cloning of the thermostable phytase gene (phy) from *Bacillus* sp. DS11 and its overexpression in *Escherichia coli*, *FEMS Microbiology Letters*, 162:182-191; and U.S. Pat. No. 6,255,098, which are hereby incorporated by reference in their entireties). These reports showed characteristic differences of *Bacillus* phytases from fungal, *E. coli*, plant, and mammal phytases in that *Bacillus* phytases do not possess the conserved RHGXRXP domain sequence that are found in known phytases (Kerovuo et al., 1998, supra; Kim et al., 1998, supra). In addition, phytases from *B. subtilis* have been shown to have specific calcium dependence for its activity and thermostability (Kerovuo et al., 2000, The metal dependence of *Bacillus subtilis* phytase, *Biochem. Biophys. Res. Commun.* 268:365-369, which is hereby incorporated by reference in its entirety), which is not found in any other reported phytases from fungi, *E. coli*, plants and mammals. Furthermore, the pH optima for *Bacillus subtilis* phytase activity also differ from those of fungal and *E. coli* phytases. Many reports have demonstrated that the fungal as well as *E. coli* phytases are acid phosphatases with pH optima ranging from 2.5 (Rodriguez et al., 1999, supra; and Dassa et al., 1990, supra) to 5.5 (Han et al., 1999, supra). In contrast, the pH optima for *Bacillus subtilis* phytases are reported by Kerovuo et al. (1998, supra) to be 7. Thus, the phytase production using generally-regarded-as-safe (GRAS) bacterial strains has great utility as providing a new and safe source of phytase to be supplemented in commercial feeds.

Maugenest et al. (1997, Cloning and characterization of a cDNA encoding a maize seedling phytase, *Biochemistry Journal* 322:511-517) reported the cloning and characterization of a maize seedling phytase. U.S. Pat. No. 6,291,224 discloses a phytase derived from *Zea mays* and U.S. Pat. No. 6,303,766 discloses a phytase derived from soybean, both of which are known to be acidic phytases. However, in general, plant phytases are normally produced in insufficient amounts to suit industrial values, furthermore, in general, very low amounts of endogenous activity can be detected in non-germinated seeds. The extracellular phytase activity is obviously not significant enough for mobilizing phytate locked up in the soil.

Plants can obtain carbon, hydrogen and oxygen from water and photosynthesis, phosphorus, nitrogen, metal ions, calcium, and trace elements are mainly obtained from soil. Therefore, the availability of phosphorus and nitrogen in soil becomes a limiting factor for plant growth. Phosphorus, mainly in the form of inorganic phosphate, is absorbed from soil by roots and the inorganic phosphate will then be transported to the other tissues of the plant for various life processes, such as DNA and RNA synthesis, etc. However, the majority of phosphorus is locked up in plants, and stored in the form of phytate salts. For plants, the phosphorus locked up as phytate in the soil is not available for plant utilization. To supply plants with the nutritional needs, inorganic phosphate is commonly supplied in fertilizers to enhance plant growth, which constitutes another source of pollutant to the environment.

Efforts to express phytase in plants have not resulted in useful phenotypes. An acidic phytase from the fungus *Aspergillus niger* (phyA) was successfully expressed in transgenic tobacco (Ullah et al., 1999, supra). The recombinant phytase recovered from the transgenic tobacco was catalytically indistinguishable from the native phytase, except that the pH optima shifted from pH 5 to 4. The same gene was overexpressed in *Arabidopsis* (Richardson et al., 2000, Extracellular secretion of *Aspergillus* phytase from *Arabidopsis* roots enables plants to obtain phosphorus from phytate. *Plant Journal* 25(6):641-649). U.S. Pat. No. 6,022,846 discloses the expression of *Aspergillus ficuum, Aspergillus niger, Aspergillus awamori*, and *Aspergillus ridulans*, acidic phytases in the fruits, leaves, and roots of various crops, (also see U.S. Pat. No. 5,900,525). Intracellular expression of these acidic fungal phytases do not produce any significant phenotypic changes in the transformed plants.

Many monogastric animals, including pigs and chickens, were fed with feeds composed of soybean meal, corn, wheat, barley, rice bran and canola meal. Since most of the phosphorus is locked up in phytate salts, exogenous phytase enzymes with a low pH optimal, mainly from fungal origins, are frequently added as feed additives. Instead of adding exogenous phytases, incorporating transgenic plants expressing active phytases into animal feed will also enhance the availability of phosphate for animals fed with such feed. Thus, the need and desire continue to exist for methods which can affect and create biochemical pathways in plants through genetic engineering.

SUMMARY OF THE INVENTION

Efficient utilization of phosphorus is important not only for the growth of plants and animals but also for reducing the environmental pollution caused by animal waste and fertilizers containing unutilized phosphorus in phytate form. In order to utilize phosphorus in various food sources, phytases from various sources can be incorporated in animal feed so that monogastric animals can utilize phosphorus efficiently and at the same time excrete less pollution-causing phosphorus into the environment. Also, if phytase, active at neutral pH, can be expressed in plants, the transgenic plants can have significant increase in growth rates and reduction in the maturation and/or flowering times. Thus, there is a need for phytases which exhibit optimal activity in animal feed and in plants and are also safe for the health of animals and plants. Furthermore, need exists to produce great amounts of phytases for the commercial applications.

The present invention is based, in part, on the discovery of two new phytase genes (see FIGS. 1 and 2; SEQ ID NOS:1, 2, 3 and 4) from two microorganisms, *Bacillus licheniformis* and *Bacillus subtilis* 168, respectively, and the observations that expression of neutral phytases enhances plant growth, flowering, and fruiting. Accordingly, the present invention relates to nucleotide sequences of two phytase genes, designated as phyL and 168phyA, respectively, (SEQ ID NOS:1 and 3, respectively; see FIGS. 1A and 2A, respectively) from two generally-regarded-as-safe (GRAS) microorganisms and amino acid sequences of their encoded proteins, as well as fragments, derivatives, analogs, and variants thereof. Accordingly, the present invention provides isolated or recombinantly prepared phytase enzymes originating from *Bacillus licheniformis* (phyL, having amino acid sequence of SEQ ID NO:2; see FIG. 1B) and *Bacillus subtilis* strain 168 (168phyA, having amino acid sequence of SEQ ID NO:4; see FIG. 2B), respectively, and fragments, derivatives, analogs, or variants thereof, as defined herein, which are herein collectively referred to as "peptides of the invention" or "proteins of the invention." Furthermore, this invention provides nucleic acid molecules encoding the polypeptides of the invention, which are herein collectively referred to as "nucleic acids of the invention" and include cDNA, genomic DNA, and RNA.

As used herein, italicizing the name of a gene shall indicate the gene, in contrast to its encoded protein or polypeptide product which is indicated by the name of the gene in the absence of any italicizing. For example, "Gene" shall mean the Gene gene, whereas "Gene" shall indicate the protein or polypeptide product of the Gene gene.

Thus, this invention provides isolated nucleic acid molecules which comprise or consist of a nucleotide sequence that is about 30%, 35%, 40%, 45%, 50%, 55%, 60%, 65%, 70%, 75%, 80%, 85%, 90%, 95%, or 98% identical to the nucleotide sequence of SEQ ID NO: 1 or a complement thereof, or SEQ ID NO:3 or a complement thereof, and encode a protein or polypeptide having an activity of phyL or 168phyA. The activity includes antigenicity, immunogenicity, catalytic activity (i.e., phytase activity), and other activities readily assayable. Further, the activity includes functioning at a neutral pH, more particularly also having a broad temperature optimum for enzymatic activity, and having the highest activity at neutral pH at the respective temperature optima (see FIG. 7B and Section 6.4, infra). Furthermore, a high thermostability is exhibited, especially in the presence of $Ca^{2+}$. In specific embodiments, such nucleic acid molecules exclude nucleotide sequences encoding phyC (SEQ ID NO:21), phyK (SEQ ID NO:23), and fragments of at least 5, 10, 15, 20, 25, 30, 35, 40, 45, 50, 55, 60, 65, 70, 75, 80, 90, 100, 120, 140, 160, 180, 200, 220, 240, 260, 280, 300, 320, 340, 360 or 380 amino acid residues in length of phyC (SEQ ID NO:22), and phyK (SEQ ID NO:24), respectively, and having phytase catalytic activity.

This invention further provides isolated nucleic acid molecules which comprise or consist of about 25, 30, 35, 40, 45, 100, 150, 200, 250, 300, 350, 400, 450, 500, 550, 600, 650, 700, 750, 800, 850, 900, 950, 1000, 1050, 1100, 1150, 1200, 1250, 1300, 1350, or more contiguous nucleotides of the nucleotide sequence of SEQ ID NO:1, 3, or a complement thereof encoding a protein or polypeptide having one or more phyL or 168phyA activities. In specific embodiments, such nucleic acid molecules exclude nucleotide sequences encoding phyC (SEQ ID NO:21), phyK (SEQ ID NO:23), fragments of at least 5, 10, 15, 20, 25, 30, 35, 40, 45, 50, 55, 60, 65, 70, 75, 80, 90, 100, 120, 140, 160, 180, 200, 220, 240, 260, 280, 300, 320, 340, 360 or 380 amino acid residues in length of phyC (SEQ ID NO:22) and phyK (SEQ ID NO:24), respectively, having phytase catalytic activity.

The present invention provides isolated polypeptides or proteins which are encoded by a nucleic acid molecule consisting of or comprising a nucleotide sequence that is at least about 30%, 35%, 40%, 45%, 50%, 55%, 60%, 65%, 70%, 75%, 80%, 85%, 90%, 95%, or 98% identical to the nucleotide sequence of SEQ ID NO:1 or a complement thereof, or SEQ ID NO:3 or a complement thereof, wherein the polypeptides or proteins also exhibit at least one structural and/or functional feature of a polypeptide of the invention. Said functional feature of a polypeptide of the invention includes antigenicity, immunogenicity, catalytic activity, and other activities readily assayable. In specific embodiments, such polypeptides or proteins exclude polypeptides or proteins encoded by nucleotide sequences of phyC (SEQ ID NO:21) and phyK (SEQ ID NO:23), respectively, and fragments of at least 25, 30, 35, 40, 45, 100, 150, 200, 250, 300, 350, 400, 450, 500, 550, 600, 650, 700, 750, 800, 850, 900, 950, 1000, 1050, 1100, 1150, 1200, 1250, or 1280 nucleotides in length of phyC (SEQ ID NO:21) and fragments of at least 25, 30, 35, 40, 45, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, or 1700 nucleotides in length of phyK (SEQ ID NO:23).

The invention provides isolated polypeptides or proteins which are encoded by a nucleic acid molecule comprising or consisting of a nucleotide sequence that contains at least about 25, 30, 35, 40, 45, 100, 150, 200, 250, 300, 350, 400, 450, 500, 550, 600, 650, 700, 750, 800, 850, 900, 950, 1000, 1050, 1100, 1150, 1200, 1250, 1300, 1350, or more contiguous nucleotides of the nucleotide sequence of SEQ ID NO:1, 3, or a complement thereof, wherein the polypeptides or proteins also exhibit at least one structural and/or functional feature of a polypeptide of the invention. In specific embodiments, such polypeptides or proteins exclude polypeptides or proteins encoded by nucleotide sequences of phyC (SEQ ID NO:21) and phyK (SEQ ID NO:23), respectively, and fragments of at least 15, 30, 45, 60, 90, 120, 180, 240, 300, 420, 540, 780, 1020, 1140, 1260, or 1280 nucleic acids in length of phyC (SEQ ID NO:21) and fragments of at least 15, 30, 45, 60, 90, 120, 180, 240, 300, 420, 540, 780, 1020, 1140, 1260, 1280, 1300, 1350, 1400, 1450, 1500, 1550, 1600, 1650, or 1700 nucleic acids in length of phyK (SEQ ID NO:23).

The invention also features isolated nucleic acid molecules comprising a nucleotide sequence encoding a protein having an amino acid sequence that is at least about 40%, 45%, 50%, 55%, 60%, 65%, 70%, 75%, 80%, 85%, 90%, 95%, or 98% identical to the amino acid sequence of SEQ ID NO:2 or 4, or fragments, derivatives, analogs, or variants of said protein, or complements of said nucleic acid molecules, and exhibits the antigenicity, immunogenicity, catalytic activity, and other activities readily assayable, of phyC and phyK. In specific embodiments, such nucleic acid molecules exclude nucleotide sequences encoding phyC (SEQ ID NO:21), phyK (SEQ ID NO:23), and fragments of at least 5, 10, 15, 20, 25, 30, 35, 40, 45, 50, 55, 60, 65, 70, 75, 80, 90, 100, 120, 140, 160, 180, 200, 220, 240, 260, 280, 300, 320, 340, or 360 amino acid residues in length of phyC (SEQ ID NO:22), and fragments of at least 5, 10, 15, 20, 25, 30, 35, 40, 45, 50, 55, 60, 65, 70, 75, 80, 90, 100, 120, 140, 160, 180, 200, 220, 240, 260, 280, 300, 320, 340, or 360 amino acid residues in length of phyK (SEQ ID NO:24), respectively.

The invention further provides isolated nucleic acid molecules comprising a nucleotide sequence encoding a protein having an amino acid sequence that comprises or consists of at least about 10, 15, 20, 25, 30, 50, 75, 100, 125, 150, 175, 200, 225, 250, 275, 300, 325, 350, 375 or more contiguous amino acid of SEQ ID NO:2 or 4, or fragments, derivatives, analogs, or variants of said protein, or complements of said nucleic acid molecules, and exhibits the antigenicity, immunogenicity, catalytic activity, and other readily assayable activities of phyC and phyK. In specific embodiments, such nucleic acid molecules exclude nucleotide sequences encoding phyC (SEQ ID NO:21), phyK (SEQ ID NO:23), a fragment of at least 5, 10, 15, 20, 25, 30, 35, 40, 45, 50, 55, 60, 65, 70, 75, 80, 90, 100, 120, 140, 160, 180, 200, 220, 240, 260, 280, 300, 320, 340, or 360 amino acid residues in length of phyC (SEQ ID NO:22), and a fragment of at least 5, 10, 15, 20, 25, 30, 35, 40, 45, 50, 55, 60, 65, 70, 75, 80, 90, 100, 120, 140, 160, 180, 200, 220, 240, 260, 280, 300, 320, 340, or 360 amino acid residues in length of phyK (SEQ ID NO:24), respectively.

Furthermore, the invention provides isolated polypeptides or proteins comprising an amino acid sequence that is at least about 40%, 45%, 50%, 55%, 60%, 65%, 70%, 75%, 80%, 85%, 90%, 95%, or 98% identical to the amino acid sequence of SEQ ID NO:2 or 4, or fragments, derivatives, analogs, or variants of said protein, wherein the polypeptides or proteins also exhibit at least one structural and/or functional feature of a polypeptide of the invention. In specific embodiments, such polypeptides or proteins exclude polypeptides or proteins encoded by nucleotide sequences of phyC (SEQ ID NO:21) and phyK (SEQ ID NO:23), respectively, and fragments of at least 5, 10, 15, 20, 25, 30, 35, 40, 45, 50, 55, 60, 65, 70, 75, 80, 90, 100, 120, 140, 160, 180, 200, 220, 240, 260, 280, 300, 320, 340, or 360 amino acid residues in length of phyC (SEQ ID NO:22) and phyK (SEQ ID NO:24), respectively.

The invention also provides isolated polypeptides or proteins comprising an amino acid sequence that comprises or consists of at least about 10, 15, 20, 25, 30, 50, 75, 100, 125, 150, 175, 200, 225, 250, 275, 300, 325, 350, 375 or more contiguous amino acid of SEQ ID NO:2 or 4, or fragments, derivatives, analogs, or variants of said protein, wherein the polypeptides or proteins also exhibit at least one structural and/or functional feature of a polypeptide of the invention. In specific embodiments, such polypeptides or proteins exclude polypeptides or proteins encoded by nucleotide sequences of phyC SEQ ID NO:21) and phyK (SEQ ID NO:23), respectively, and fragments of at least 5, 10, 15, 20, 25, 30, 35, 40, 45, 50, 55, 60, 65, 70, 75, 80, 90, 100, 120, 140, 160, 180, 200, 220, 240, 260, 280, 300, 320, 340, or 360 amino acid residues in length of phyC (SEQ ID NO:22) and phyK (SEQ ID NO:24), respectively.

In one embodiment, this invention provides isolated nucleic acid molecules which hybridize under stringent conditions, as defined herein, to a nucleic acid having the sequence of SEQ ID NO:1 or 3, or a complement thereof, wherein the nucleic acid molecules encode proteins or polypeptides which exhibit at least one structural and/or functional feature of the polypeptides of the invention.

Furthermore, this invention also provides nucleic acid molecules which are suitable for use as primers or hybridization probes for the detection of nucleic acids encoding a polypeptide of the invention or other sequences similar to a polypeptide of the invention.

Another aspect of the invention provides vectors, e.g., recombinant expression vectors, comprising a nucleic acid molecule of the invention. Furthermore, the invention also provides host cells containing such a vector or engineered to contain and/or express a nucleic acid molecule of the invention and host cells containing a nucleotide sequence of the invention operably linked to a heterologous promoter. In certain embodiments, the host cell is a *Bacillus* sp., preferably *Bacillus subtilis* MU331. In a particular embodiment, such a heterologous promoter is a strong prophage promoter.

The invention further provides methods for preparing a polypeptide of the invention by a recombinant DNA technology in which the host cells containing a recombinant expression vector encoding a polypeptide of the invention or a nucleotide sequence encoding a polypeptide of the invention operably linked to a heterologous promoter, are cultured, and the polypeptide of the invention produced and isolated. In certain embodiments, the host cell is a *Bacillus* sp., preferably *Bacillus subtilis* MU331. In a particular embodiment, the present invention provides a rapid process for producing a large quantity of a polypeptide of the invention using phage $\phi$105 overexpression system.

Another aspect of the present invention is to provide animal feed containing a polypeptide of the invention which releases phosphorous from phytate to be available to the animal as well as a method for preparing such animal feed.

In yet another embodiment, the invention provides a transgenic plant containing a nucleic acid molecule which encodes a phytase having a catalytic ability at neutral pH. In a specific embodiment, the invention provides a transgenic plant containing a nucleic acid molecule of the invention that expresses a phytase of the invention or functionally active fragment, homolog, or analog thereof, or a nucleic acid molecule that encodes a phytase derived from *Bacillus* sp. In a preferred embodiment, the phytase is expressed intracellularly. In another preferred embodiment, the phytase is expressed extracellularly, for example, from roots of the transgenic plants. The expressed phytase is active at neutral pH and allows the plant to release phosphorus from phytate stored in the plant or in the environment, such as in the soil. The invention also provides a method for producing such a transgenic plant.

The invention further provides antibodies that immunospecifically bind a polypeptide of the invention. Such antibodies include, but are not limited to, antibodies from various animals, humanized, chimeric, polyclonal, monoclonal, bi-specific, multi-specific, single chain antibodies, Fab fragments, F(ab')$_2$ fragments, disulfide-linked Fvs, fragments containing either a VL or VH domain or even a complementary determining region (CDR), that immunospecifically binds to a polypeptide of the invention.

In one embodiment, the invention provides method for detecting the presence, activity or expression of a polypeptide of the invention or similar polypeptide in a biological material, such as cells, culture media, and so forth. The increased or decreased activity or expression of the polypeptide in a sample relative to a control sample can be determined by contacting the biological material with an agent which can detect directly or indirectly the presence, activity or expression of the polypeptide of the invention. In a particular embodiment, such an agent is an antibody or a fragment thereof which immunospecifically binds to a polypeptide of the invention. In another particular embodiment, such an agent is phytate.

In another embodiment, the invention provides a fusion protein comprising a bioactive molecule and one or more domains of a polypeptide of the invention or fragment thereof. In particular, the present invention provides fusion proteins comprising a bioactive molecule recombinantly fused or chemically conjugated (including both covalent and non-covalent conjugations) to one or more domains of a polypeptide of the invention or fragments thereof.

3.1 Definitions

The term "acidic" or "acid pH" as used herein refers to a pH value of less than 6.0, less than 5.5, less than 5.0, and less than 4.0.

The term "analog" as used herein refers to a polypeptide that possesses a similar or identical function to phyL or 168phyA, a fragment of phyL or 168phyA, but does not necessarily comprise a similar or identical amino acid sequence of phyL or 168phyA, a fragment of phyL or 168phyA, or possess a similar or identical structure of phyL or 168phyA, an antibody, or antibody fragment. A polypeptide that has a similar amino acid sequence refers to a polypeptide that satisfied at least one of the following: (i) a polypeptide having an amino acid sequence that is at least 30%, at least 35%, at least 40%, at least 45%, at least 50%, at least 55%, at least 60%, at least 65%, at least 70%, at least, 75%, at least 80%, at least 85%, at least 90%, at least 95%, or at least 99% identical to the amino acid sequence of a phyL or 168phyA, or a fragment of phyL or 168phyA, with the proviso that the polypeptide is neither phyC nor phyK, nor a fragment of at least 5, 10, 15, 20, 25, 30, 35, 40, 45, 50, 55, 60, 65, 70, 75, 80, 90, 100, 120, 140, 160, 180, 200, 220, 240, 260, 280, 300, 320, 340, or 360 aa in length of phyC or phyK; (ii) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the nucleotide sequence encoding phyL or 168phyA, a fragment of phyL or 168phyA, with the proviso that the polypeptide is neither phyC nor phyK, nor a fragment of phyC or phyK; (iii) a polypeptide encoded by a nucleotide sequence that hybridizes under stringent conditions as defined herein to a nucleotide sequence encoding phyL or 168phyA, a fragment of phyL or 168phyA, of at least 10 amino acid residues, at least 15 amino acid residues, at least 20 amino acid residues, at least 25 amino acid residues, at least 40 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, at least 225 amino acid residues, at least 250 amino acid residues, at least 275 amino acid residues, at least 300 amino acid residues, at least 325 amino acid residues, at least 350 amino acid residues, or at least 375 amino acid residues, with the proviso that the polypeptide is neither phyC nor phyK, nor a fragment of phyC or phyK. A polypeptide with similar structure and function, exhibiting the antigenicity, immunogenicity, catalytic activity, and other readily assayable activities, to a phyL or 168phyA, a fragment of phyL or 168phyA, refers to a polypeptide that has a similar secondary, tertiary, or quaternary structure of phyL or 168phyA, or a fragment of phyL or 168phyA. The structure of a polypeptide can be determined by methods known to those skilled in the art, including but not limited to, X-ray crystallography, nuclear magnetic resonance, and crystallographic electron microscopy, and the function of a polypeptide can be determined by various assays to determine biological activities of the polypeptides.

The term "an antibody or an antibody fragment which immunospecifically binds phyL or 168phyA" as used herein refers to an antibody or a fragment thereof that immunospecifically binds to phyL or 168phyA, or a fragment of phyL or 168phyA and does not non-specifically bind to other polypeptides. An antibody or a fragment thereof that immunospecifically binds to phyL or 168phyA, or a fragment of phyL or 168phyA, may cross-react with other antigens. Preferably, an antibody or a fragment thereof that immunospecifically binds to phyL or 168phyA, or a fragment of phyL or 168phyA, does not cross-react with other antigens. An antibody or a fragment thereof that immunospecifically binds phyL or 168phyA, or a fragment of phyL or 168phyA, can be identified by, for example, immunoassays or other techniques known to those skilled in the art. An antibody or an antibody fragment which immunospecifically binds phyL or 168phyA may be interchangeably referred to as "anti-phyL antibody" or "anti-168phyA antibody," respectively.

The term "derivative" as used herein refers to a given peptide or protein that is otherwise modified, e.g., by covalent attachment of any type of molecule, preferably having bioactivity, to the peptide or protein, including the incorporation of non-naturally occurring amino acids. The resulting bioactivity retains one or more biological activities of the peptide protein.

The term "fragment" as used herein refers to a fragment of a nucleic acid molecule containing at least about 25, 30, 35, 40, 45, 100, 150, 200, 250, 300, 350, 400, 5450, 500, 550, 600, 650, 700, 750, 800, 850, 900, 950, 1000, 1050, 1100, 1150, 1200, 1250, 1300, 1350, or more contiguous nucleic acids in length of the relevant nucleic acid molecule and having at least one functional feature of the nucleic acid molecule (or the encoded protein has one functional feature of the protein encoded by the nucleic acid molecule); or a fragment of a protein or a polypeptide containing at least 5, 10, 15, 20, 25, 30, 35, 40, 45, 50, 55, 60, 65, 70, 75, 80, 90, 100, 120, 140, 160, 180, 200, 220, 240, 260, 280, 300, 320, 340, or 360 amino acid residues in length of the relevant protein or polypeptide and having at least one functional feature of the protein or polypeptide.

The term "generally-regarded-as-safe (GRAS)" as used herein refers to a nature of certain substances which are classified as being "GRAS" for the intended use by the Food and Drug Administration (FDA). Such substances can be used in the production of food, provided that "good manufacturing practice" is applied. The GRAS status for an enzyme preparation can be granted by the FDA on the basis of the documentation presented. GRAS status pertains to enzymes that are obtained from plants and animals and also those from microorganisms that have been used as enzyme sources for a long time for human use without causing serious health problems.

An "isolated" or "purified" peptide or protein is substantially free of cellular material or other contaminating proteins from the cell or tissue source from which the protein is derived, or substantially free of chemical precursors or other chemicals when chemically synthesized. The language "substantially free of cellular material" includes preparations of a polypeptide/protein in which the polypeptide/protein is separated from cellular components of the cells from which it is isolated. Thus, a polypeptide/protein that is substantially free of cellular material includes preparations of the polypeptide/protein having less than about 30%, 20%, 10%, 5%, 2.5%, or 1%, (by dry weight) of contaminating protein. When the polypeptide/protein is recombinantly produced, it is also preferably substantially free of culture medium, i.e., culture medium represents less than about 20%, 10%, or 5% of the volume of the protein preparation. When polypeptide/protein is produced by chemical synthesis, it is preferably substantially free of chemical precursors or other chemicals, i.e., it is separated from chemical precursors or other chemicals which are involved in the synthesis of the protein. Accordingly, such preparations of the polypeptide/protein have less than about 30%, 20%, 10%, 5% (by dry weight) of chemical precursors or compounds other than polypeptide/protein fragment of interest. In a preferred embodiment of the present invention, polypeptides/proteins are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized, but excludes nucleic acid molecules present in recombinant DNA libraries. In a preferred embodiment of the invention, nucleic acid molecules encoding polypeptides/proteins of the invention are isolated or purified.

The term "neutral pH" as used herein refers to a pH value of between about 5.5 to about 8.5, preferably about 6.0 to about 8.0, more preferably about 6.5 to about 7.5, and most preferably about 7.0.

The term "operably linked" as used herein refers to when transcription under the control of the "operably linked" promoter produces a functional messenger RNA, translation of which results in the production of the polypeptide encoded by the DNA operably linked to the promoter.

The term "under stringent condition" refers to hybridization and washing conditions under which nucleotide sequences having at least 70%, at least 75%, at least 80%, at least 85%, at least 90%, or at least 95% identity to each other remain hybridized to each other. Such hybridization conditions are described in, for example but not limited to, *Current Protocols in Molecular Biology*, John Wiley & Sons, N.Y. (1989), 6.3.1-6.3.6.; *Basic Methods in Molecular Biology*, Elsevier Science Publishing Co., Inc., N.Y. (1986), pp. 75-78, and 84-87; and *Molecular Cloning*, Cold Spring Harbor Laboratory, N.Y. (1982), pp. 387-389, and are well known to those skilled in the art. A preferred, non-limiting example of stringent hybridization conditions is hybridization in 6× sodium chloride/sodium citrate (SSC), 0.5% SDS at about 68° C. followed by one or more washes in 2×SSC, 0.5% SDS at room temperature. Another preferred, non-limiting example of stringent hybridization conditions is hybridization in 6×SSC at about 45° C. followed by one or more washes in 0.2×SSC, 0.1% SDS at about 50-65° C.

The term "variant" as used herein refers either to a naturally occurring allelic variation of a given peptide or a recombinantly prepared variation of a given peptide or protein in which one or more amino acid residues have been modified by amino acid substitution, addition, or deletion.

BRIEF DESCRIPTION OF THE FIGURES

The patent or application file contains at least one drawing executed in color. Copies of this patent or patent application publication with color drawing(s) will be provided by the Office upon request and payment of the necessary fee.

The following figures illustrate the embodiments of the invention and are not meant to limit the scope of the invention encompassed by the claims.

FIGS. 1A and 1B show the nucleotide sequence of phyL (SEQ ID NO:1) and the amino acid sequence of phyL (SEQ ID NO:2), respectively.

FIGS. 2A and 2B show the nucleotide sequence of 168phyA (SEQ ID NO:3) and amino acid sequence of 168phyA (SEQ ID NO:4), respectively.

FIG. 13a).

DETAILED DESCRIPTION OF THE INVENTION 5.1 PhyL and 168phyA.

Figure 5A:
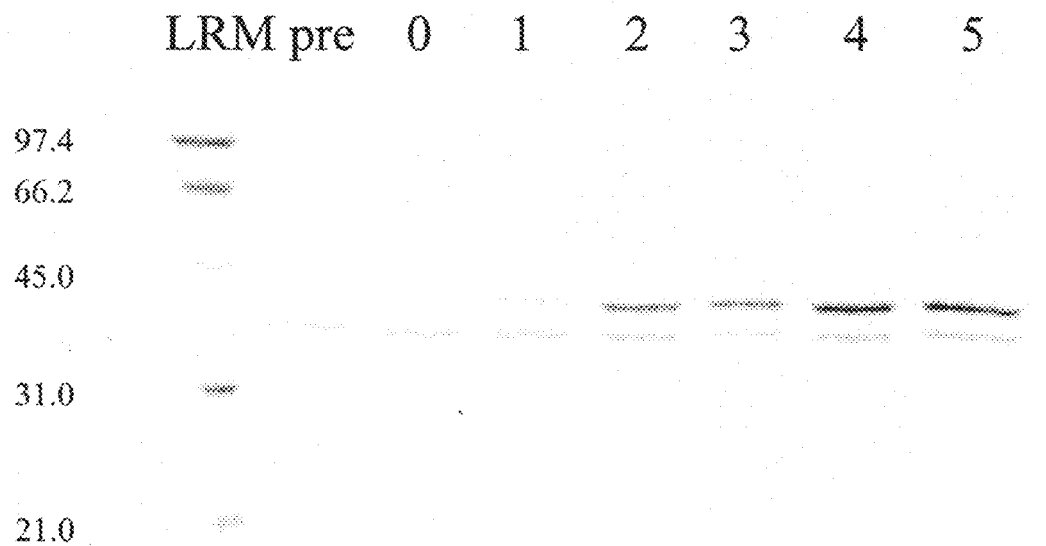
FIGS. 5A and 5B show the expression level of the two *Bacillus* phytases. Samples are taken directly from bacterial cultures and centrifuged before loading into a 10% SDS-polyacrylamide gel. Bacterial cultures were collected pre-heat induction and from 0 to 5 hours post-heat induction. It can be observed that the production of enzyme increases with time after heat induction. LRM is the low molecular weight marker (BIO-RAD, Hong Kong) with reference protein sizes marked on the left of the ladder. (A) shows the expression of enzyme encoded by 168phyA. (B) shows the expression of enzyme encoded by phyL.

An open reading frame (ORF) having high sequence homology to two published phytases in *Bacillus subtilis* were found in the genome of *B. subtilis* 168. Cloned 168phyA expressed as described in Section 6.3 showed a mature phytase 168phyA with a molecular weight (MW) of 44 kDa as determined by SDS-PAGE (see FIG. 5A). PhyL was cloned from *Bacillus licheniformis* by degenerate PCR reactions using degenerate oligonucleotides based on the conserved amino acid sequence among 168phyA, phyK (Kim Y. O., et al., 1998, Cloning of the thermostable phytase gene (phy) from *Bacillus* sp. DS11 and its overexpression in *Escherichia coli. FEMS Microbiology Letters:* 162:182-191) and phyC (Kerovuo J., et al., 1998, Isolation, characterization, molecular gene cloning, and sequencing of a novel phytase from *Bacillus subtilis. Applied and Environmental Microbiology* 64(6):2079-2085). The amino acid sequence deduced from the nucleotide sequence revealed a protein of 381 amino acid residues and, like 168phyA and other *B. subtilis* phytases, did not possess the highly conserved RHGXRXP sequence motif commonly found among fungal and *E. coli* phytases. The MW of phyL was about 47 kDa as determined by SDS-PAGE (see FIG. 5B).

Figure 7A:
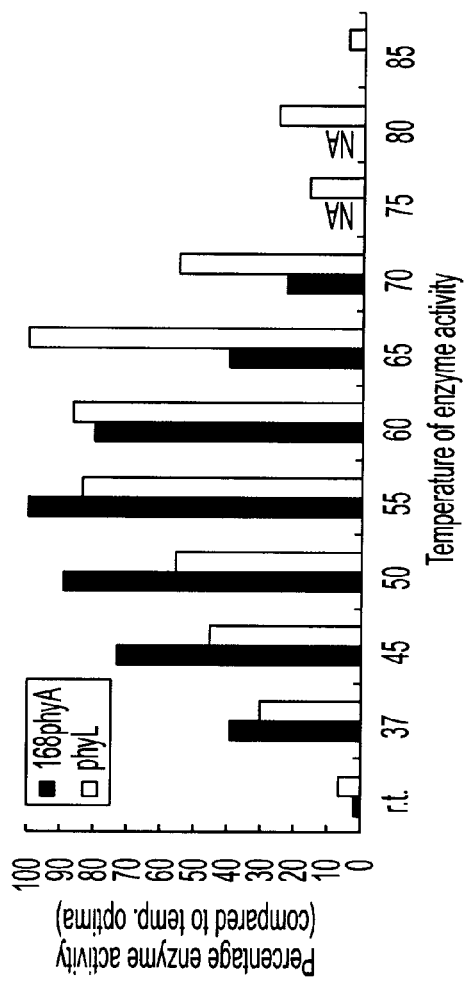
FIGS. 7A and 7B represent the temperature and pH profiles, respectfully, for the enzymes included in the present invention. Phytase activities were measured according to the method described by Engelen et al. (1994, Simple and Rapid Determination of Phytase Activity. *Journal of AOAC International*, 77(3):760-764), except that the assay was scaled down to 1 ml. Colorimetric determination was done by measuring the optical density at 405 nm. The incubation time was set at 30 minutes. All reactions were supplemented with 5 mM $CaCl_2$ to ensure enzyme activity.

The enzymatic activity of these two phytases of the invention was measured using the assay method by Engelen A. J. et al., (1994, Simple and Rapid Determination of Phytase Activity. *Journal of AOAC International* 77(3):760-764). The results showed that both 168phyA and phyL have broad temperature optima for their enzymatic activities, peaking at 65° C. for phyL and 55° C. for 168phyA (see FIG. 7A and Section 6.4, infra). In addition, the two enzymes of the invention showed the highest activity at neutral pH at the respective temperature optima (see FIG. 7B and Section 6.4, infra). Furthermore, both enzymes of the present invention exhibit high thermostability especially in the presence of $Ca^{2+}$ (see Section 6.4). These characteristics of the polypeptides of the invention, i.e., the broad optimal temperature range, high thermostability, and optimal enzymatic activity at neutral pH, implicate great commercial utility of the polypeptides as discussed in Section 5.10.

Thus, the invention provides nucleic acid molecules having sequences of SEQ ID NOS:1 and 3, phyL and 168phyA, respectively, and the encoded polypeptides thereby having sequences of SEQ ID NOS:2 and 4, phyL and 168phyA, respectively.

5.2 Analogs, Derivatives, and Variants of phyL and 168phyA

In addition to the nucleic acid molecules and polypeptides described above, the nucleic acid molecules and polypeptides of the invention also encompass those nucleic acid molecules and polypeptides having a common biological activity, similar or identical structural domain and/or having sufficient nucleotide sequence or amino acid identity (analogs) to those of the nucleic acid molecules and polypeptides of the invention described above.

Such common biological activities of the polypeptides of the invention include antigenicity, immunogenicity, catalytic activity especially at neutral pH, and other activities readily assayable by the skilled artisan.

A polypeptide that has a similar amino acid sequence refers to a polypeptide that satisfied at least one of the following: (i) a polypeptide having an amino acid sequence that is at least 30%, at least 35%, at least 40%, at least 45%, at least 50%, at least 55%, at least 60%, at least 65%, at least 70%, at least, 75%, at least 80%, at least 85%, at least 90%, at least 95%, or at least 99% identical to the amino acid sequence of a phyL (SEQ ID NO:2) or 168phyA (SEQ ID NO:4), a fragment of phyL or 168phyA, and having at least one functional feature of a polypeptide of the invention, with the proviso that the polypeptide is neither phyC nor phyK, nor a fragment of phyC or phyK; (ii) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the nucleotide sequence encoding phyL (SEQ ID NO:1) or 168phyA (SEQ ID NO:3), a fragment of phyL or 168phyA and having at least one structural and/or functional feature of the polypeptide of the invention, with the proviso that the polypeptide is neither phyC nor phyK, nor a fragment of phyC or phyK; (iii) a polypeptide encoded by a nucleotide sequence that hybridizes under stringent conditions as defined herein to a nucleotide sequence encoding phyL (SEQ ID NO:1) or 168phyA (SEQ ID NO:3), a fragment of phyL or 168phyA and having at least one structural and/or functional feature of a polypeptide of the invention, and having at least 10 amino acid residues, at least 15 amino acid residues, at least 20 amino acid residues, at least 25 amino acid residues, at least 40 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, at least 225 amino acid residues, at least 250 amino acid residues, at least 275 amino acid residues, at least 300 amino acid residues, at least 325 amino acid residues, at least 350 amino acid residues, or at least 375 amino acid residues, with the proviso that the polypeptide is neither phyC nor phyK, nor a fragment of phyC or phyK. A polypeptide with similar structure to a phyL or 168phyA, or a fragment of phyL or 168phyA, refers to a polypeptide that has a similar secondary, tertiary, or quaternary structure of phyL or 168phyA, a fragment of phyL or 168phyA and has at least one functional feature of a polypeptide of the invention. The structure of a polypeptide can be determined by methods known to those skilled in the art, including but not limited to, X-ray crystallography, nuclear magnetic resonance, and crystallographic electron microscopy. In a preferred embodiment, the polypeptides of the invention are derived from a GRAS strain of *Bacillus* bacteria.

The invention also encompasses derivatives of polypeptides of the invention. For example, but not by way of limitation, derivatives may include peptides or proteins that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, etc. Additionally, the derivative may contain one or more non-classical amino acids.

In another aspect, an isolated nucleic acid molecule of the invention encodes a variant of a polypeptide of the invention in which the amino acid sequences have been modified by genetic engineering so that biological activities of the polypeptides are either enhanced or reduced, or the local structures thereof are changed without significantly altering the biological activities. In one aspect, these variants can act as either agonists or as antagonists. An agonist can retain substantially the same or a portion of the biological activities of the polypeptides of the invention and an antagonist can inhibit one or more of the activities of the polypeptides of the invention. Such modifications include amino acid substitution, deletion, and/or insertion. Amino acid modifications can be made by any method known in the art and various methods are available to and routine for those skilled in the art.

For example, mutagenesis may be performed in accordance with any of the techniques known in the art including, but not limited to, synthesizing an oligonucleotide having one or more modifications within the sequence of a given polypeptide to be modified. Site-specific mutagenesis can be conducted using specific oligonucleotide sequences which encode the nucleotide sequence containing the desired mutations in addition to a sufficient number of adjacent nucleotides in the polypeptide. Such oligonucleotides can serve as primers which can form a stable duplex on both sides of the deletion junction being traversed. Typically, a primer of about 17 to about 75 nucleotides or more in length is preferred, with about 10 to about 25 or more residues on both sides of the junction of the sequence being altered. A number of such primers introducing a variety of different mutations at one or more positions may be used to generated a library of mutants.

The technique of site-specific mutagenesis is well known in the art, as described in various publications (e.g., Kunkel et al., *Methods Enzymol.*, 154:367-82, 1987, which is hereby incorporated by reference in its entirety). In general, site-directed mutagenesis is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as T7 DNA polymerase, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and clones are selected which include recombinant vectors bearing the mutated sequence arrangement. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

Alternatively, the use of PCR with commercially available thermostable enzymes such as Taq DNA polymerase may be used to incorporate a mutagenic oligonucleotide primer into an amplified DNA fragment that can then be cloned into an appropriate cloning or expression vector. See, e.g., Tomic et al., *Nucleic Acids Res.*, 18(6):1656, 1987, and Upender et al., *Biotechniques*, 18(1):29-30, 32, 1995, for PCR-mediated mutagenesis procedures, which are hereby incorporated in their entireties. PCR employing a thermostable ligase in addition to a thermostable polymerase may also be used to incorporate a phosphorylated mutagenic oligonucleotide into an amplified DNA fragment that may then be cloned into an appropriate cloning or expression vector (see e.g., Michael, *Biotechniques*, 16(3):410-2, 1994, which is hereby incorporated by reference in its entirety).

Other methods known to those skilled in art of producing sequence variants of a given polypeptide or a fragment thereof can be used. For example, recombinant vectors encoding the amino acid sequence of the polypeptide or a fragment thereof may be treated with mutagenic agents, such as hydroxylamine, to obtain sequence variants.

Preferably, the amino acid residues to be modified are surface exposed residues. Additionally, in making amino acid substitutions, preferably the amino acid residue to be substituted is a conservative amino acid substitution, for example, a polar residue is substituted with a polar residue, a hydrophilic residue with a hydrophilic residue, hydrophobic residue with a hydrophobic residue, a positively charged residue with a positively charged residue, or a negatively charged residue with a negatively charged residue. Moreover, preferably, the amino acid residue to be modified is not highly or completely conserved across strains or species and/or is critical to maintain the biological activities of the protein.

Accordingly, included in the scope of the invention are nucleic acid molecules encoding a polypeptide of the invention that contains amino acid modifications that are not critical to its biological activity.

5.3 Enzyme Production by the Phage ϕ105 Overexpression System

Reported methods for induction of phytase over-expression include IPTG induction for the expression of phyK gene from *B. subtilis* DS11 in *E. coli* (Kim et al., 1998, supra), methanol induction for the expression of *Aspergillus* phyA gene in the yeast *Pichia pastoris* (Han & Lei, 1999, supra) and using the substrate phytate as the inducing agent to produce the phytase from *Klebsiella terrigena* in *E. coli* (Greiner et al., 1997) and phyC encoded phytase in *E. coli*. Using phytate as an inducing agent is based on the theory of substrate specificity.

In the previously established ϕ105 system in *Bacillus subtilis* (Thornewell, S. J., Ease A. K., Errington J., 1993, An efficient expression and secretion system based on *Bacillus subtilis* phage ϕ105 and its use for the production of *B. cereus* β-lactamase I. *Gene*, 133:47-53, which is hereby incorporated by reference in its entirety), a defective prophage vector, ϕ105 MU331 was derived for high-level protein over-expression in *B. subtilis* (Leung Y. C. and Erington J., 1995, Characterization of an insertion in the phage ϕ105 genome that blocks host *Bacillus subtilis* lysis and provides strong expression of heterologous genes. *Gene*, 154:1-6, which is hereby incorporated by reference in its entirety). In this derived system, a lacZ reporter gene (i.e., lacZ-cat cartridge from plasmid pSG23; Errington, J., 1986, A general method for fusion of the *Escherichia coli* lacZ gene to chromosomal genes in *Bacillus subtilis*, *J. Gen. Microbiolo.* 132:2953-2966) is inserted into the region which resembles the lysis cassette of various phages, such as λ phage. This system provides not only efficiently inducible (by heat) transcription of the gene, but also the system where the lysis of the host cell is prevented. Thus, the enzyme produced in the culture media can be easily isolated without disruption of the cells and, therefore, the purification steps can be greatly simplified. In addition, unlike *E. coli*, Bacilli are GRAS bacteria and their protein products are also GRAS to animals, including humans.

Accordingly, the nucleic acid molecules of the present invention are inserted into the expression vector pSG to construct pSGt-pL for the expression of phyL and pSG-pA for the expression of 168phyA. The gene fragment encoding the mature phyL is amplified by PCR using the primers flanking the coding region from the translation codon ATG through the stop codon of the phyL gene and subcloned into the expression vector pSGt that is constructed by subcloning the terminator of the α-amylase gene of *B. licheniformis* into the expression vector pSG (see FIG. 4B and Section 6.2, infra). Thus, the phyL gene is under the control of the ϕ105 prophage promoter in the construct pSGt-pL. The construct PSG-pA is prepared by subcloning the PCR product obtained using the primers flanking the open reading frame (ORF) of 168phyA into the expression vector pSG. In this construct, the 168phyA gene is flanked by the ϕ105 promoter and the native terminator of the 168phyA gene (see FIG. 4A and Section 6.3). These plasmids are introduced into *E. coli* strain JM109 for amplification and selection for antibiotic resistant clones and then to the host strains, such as *B. subtilis* MU331, for the production of enzymes. Accordingly, the invention further includes vectors, host cells, and methods of recombinant production of phytases (see Sections 6.2 and 6.3 for details). In certain embodiments, the host cell is a *Bacillus* sp., preferably *Bacillus subtilis* MU331.

5.4 Fusion Proteins

The present invention further encompasses fusion proteins in which the polypeptides of the invention or fragments thereof, are recombinantly fused or chemically conjugated (e.g., covalent and non-covalent conjugations) to heterologous polypeptides (i.e., an unrelated polypeptide or portion thereof, preferably at least 10, at least 20, at least 30, at least 40, at least 50, at least 60, at least 70, at least 80, at least 90 or at least 100 amino acids of the polypeptide) to generate fusion proteins. The fusion can be direct, but may occur through linker sequences.

In one aspect, the fusion protein comprises a polypeptide of the invention which is fused to a heterologous signal sequence at its N-terminus. For example, the signal sequence naturally found in the polypeptide of the invention can be replaced by a signal sequence which is derived from a heterologous origin. Various signal sequences are commercially available. For example, the phoA secretory signal (Sambrook et al., supra; and *Current Protocols in Molecular Biology*, Ausubel et al., eds., John Wiley & Sons, 1992) and the protein A secretory signal (Pharmacia Biotech; Piscataway, N.J.) are commercially available as prokaryotic heterologous signal sequences.

In another embodiment, a polypeptide of the invention can be fused to tag sequences, e.g., a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, *Proc. Natl. Acad. Sci. USA*, 86:821-824, for instance, hexa-histidine provides for convenient purification of the fusion protein. Other examples of peptide tags are the hemagglutinin "HA" tag, which corresponds to an epitope derived from the influenza hemagglutinin protein (Wilson et al., 1984, *Cell*, 37:767) and the "flag" tag (Knappik et al., 1994, *Biotechniques*, 17(4):754-761). These tags are especially useful for purification of recombinantly produced polypeptides of the invention.

Fusion proteins can be produced by standard recombinant DNA techniques or by protein synthetic techniques, e.g., by use of a peptide synthesizer. For example, a nucleic acid molecule encoding a fusion protein can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology*, Ausubel et al., eds., John Wiley & Sons, 1992).

The nucleotide sequence coding for a fusion protein can be inserted into an appropriate expression vector, i.e., a vector which contains the necessary elements for the transcription and translation of the inserted protein-coding sequence.

In a specific embodiment, the expression of a fusion protein is regulated by an inducible promoter.

5.5 Purification of Recombinant Proteins

Once the polypeptides of the invention have been produced by the methods described above, they may be purified by any methods known in the art for the purification of recombinant proteins, for example but not by way of limitation, chromatography (e.g., ion exchange, affinity, particularly by affinity for the specific antibodies, and gel filtration chromatography), centrifugation, differential solubility, or by any other standard techniques for the purification of proteins. Further, the polypeptides of the present invention or fragments thereof may be fused to heterologous polypeptide sequences described herein or otherwise known in the art to facilitate purification.

In a specific embodiment, phyL or 168phyA expressed by the *Bacillus subtilis* is purified from the bacterial cell culture supernatant by ethanol precipitation, followed by centrifugation, and gel filtration column of the resuspended precipitate (see Sections 6.2 and 6.3).

5.6 Preparation of Animal Feed

The polypeptides of the present invention, prepared as described in Sections 5.1-5.5, supra, having a phytase activity at neutral pH, can be then utilized to provide animal feed in which phosphorus is made efficiently available to the animals fed with such feed. Thus, another aspect of the present invention is to provide animal feed containing a polypeptide of the invention which releases phosphorus from phytate to be available to the animal. Such animal feed can be prepared, for example, by mixing the feed, prior to being made to pellets, with the phytase enzyme powder of the invention having enzymatic activity of 200,000-400,000 EU/kg at a weight ratio of about 1 kg powder per ton of feed. To achieve even mixing, the enzyme powder may be first mixed with a small amount, for example, 10 kg of feed and then with the remaining portion of the feed. The dose of enzyme in the feed is at least 200 enzyme unit (EU)/kg feed, preferably at least 250 EU/kg feed, and most preferably at least 300 EU/kg feed. One enzyme unit (EU) is equal to 1 μmole ortho-phosphate liberated from 5.1 mM sodium phytate within 1 minute at 37° C. and pH 7.0. Feeds can be composed of maize, corn, wheat, barley, rice bran, soybean meal and canola meal, or any other materials commonly used for animal feed.

5.7 Preparation of Transgenic Plants

Plant growth requires elements including carbon, hydrogen, oxygen, phosphorous, nitrogen, metal ions and trace elements. While plants can obtain carbon, hydrogen and oxygen from water and photosynthesis, phosphorous, nitrogen, metal ions and trace elements are mainly obtained from soil. Therefore, the availability of phosphorous and nitrogen in soil becomes a limiting factor for plant growth.

The present invention is based upon the discovery that a phytase from an organism in another kingdom can function effectively with essential biopathway components in a plant despite the wide divergence between the gene and protein sequences and structures of the phytases between the two kingdoms. Thus, the present invention involves creation of a new biochemical pathway in the plant that can shift the form of phosphorus from unavailable phytate into available inorganic phosphate and thereby enhance the growth performance of plants as indicated by, for example, the increased number of lateral buds. Since phosphate is also required for flowering and fruiting, the present invention also provides flowering plants which have improved flowering (e.g., earlier flowering and increased number of buds/flowers) and fruiting (e.g., increased number of fruits).

Accordingly, the present invention provides a transgenic plant containing a nucleic acid molecule that encodes and expresses a phytase having an optimal catalytic activity at neutral pH. The transgenic plants of the invention have improved growth, flowering, and fruiting relative to comparable unengineered plants i.e. same species (strain). In a specific embodiment, such a phytase is from a *Bacillus* species having an optimal catalytic activity at neutral pH. In a preferred embodiment, a transgenic plant of the present invention comprises a nucleic acid molecule of the present invention and expresses phyL (SEQ ID NO:2) or 168phyA (SEQ ID NO:4) that is active at neutral pH and at broad temperature range, i.e., from about 37° C. to about 70° C. for phyL, and from about 37° C. to about 65° C. for 168phyA. In a preferred embodiment, the phytase is not secreted detectably or in significant amount (i.e., not more than 1%, 2%, 5%, or 10% of the total phytase). SEQ ID NOS:2 and 4 have a native signal peptide, but the proteins are not appreciably secreted. In another preferred embodiment, the phytase is expressed extracellularly, for example, for secretion from the root of the transgenic plant. Such an extracellular expression of the neutral phytase in plants can be achieved by fusing onto the N-terminus or replacing a nucleotide sequence encoding a native signal peptide of the phytase gene (i.e., all or a portion, particularly an N-terminal portion, of amino acid residues 1 to 80, preferably all or a portion of amino acid residues 1 to 20, for phyL (SEQ ID NO:2) or all or a portion, particularly an N-terminal portion, of amino acid residues 1 to 80, preferably all or a portion of amino acid residues 1 to 26, for 168phyA (SEQ ID NO:4)) with a heterologous nucleotide sequence encoding a plant signal peptide which can efficiently secrete the phytase upon translation thereof from the cells of a given plant. The examples of plant signal peptide include, but not by way of limitation, signal peptides from extensin or extensin-related polypeptides (Richardson et al., 2001, *Plant Journal* 25:641-649), acid phosphatase (Haran,-S; Logendra,-S; Seskar,-M; Bratanova,-M; Raskin,-I., October, 2000, Characterization of *Arabidopsis* acid phosphatase promoter and regulation of acid phosphatase expression, *Plant-Physiol.* 124(2):615-626), endoplasmic reticulum signal peptide (Borisjuk,-N-V; Borisjuk,-L-G; Logendra,-S; Petersen,-F; Gleba,-Y; Raskin,-I., May, 1999, Production of recombinant proteins in plant root exudates, *Nat-Biotechnol.* 17(5):466-9), alpha-amylase (Park C S, Chang C C, Kim J Y, Ogrydziak D M, Ryu D D., 1997, Expression, secretion, and processing of rice alpha-amylase in the yeast *Yarrowia lipolytica*, *Biol Chem* 272:6876-6881) and PVR3 (Choi,-D-W; Song,-J-Y; Oh,-M-H; Lee,-J-S; Moon,-J; Suh,-S-W; Kim,-S-G., March, 1996, Isolation of a root-specific cDNA encoding a ns-LTP-like protein from the roots of bean (*Phaseolus vulgaris* L.) seedlings, *Plant-Mol-Biol.* 30(5): 1059-66). Accordingly, in another preferred embodiment, a transgenic plant of the present invention comprises a nucleic acid molecule of the present invention and expresses phyL (SEQ ID NO:2) or 168phyA (SEQ ID NO:4) except all or a portion, particularly an N-terminus portion, of amino acid residues 1 to 80, preferably all or a portion of amino acid residues 1 to 20, of SEQ ID NO:2 or all or a portion, particularly an N-terminus portion, of amino acid residues 1 to 80, preferably all or a portion of amino acid residues 1 to 26, of SEQ ID NO:4 are replaced by a heterologous plant signal peptide by genetic engineering. In such a transgenic plant, neutral phytases are secreted into the soil and mobilize soil phytate into inorganic phosphate for plant uptake. In yet another preferred embodiment, a transgenic plant of the present invention comprises at least two nucleic acid molecules of the present invention, wherein one of the nucleic acid molecule encodes phyL (SEQ ID NO:2) and the other encodes phyL in which all or a portion, particularly an N-terminal portion, of amino acid residues 1 to 80, preferably all or a portion of amino acid residues 1 to 20, of SEQ ID NO:2 are replaced by a heterologous plant signal peptide. In another preferred embodiment, a transgenic plant of the present invention comprises at least two nucleic acid molecules of the present invention, wherein one of the nucleic acid molecule encodes 168phyA (SEQ ID NO:4) and the other encodes 168phyA in which all or a portion, particular an N-terminal portion, of amino acid residues 1 to 80, preferably all or a portion of amino acid residues 1 to 26 of SEQ ID NO:4 are replaced by a heterologous plant signal peptide. Such transgenic plants express the phytases both intracellularly and extracellularly. In another preferred embodiment, a transgenic plant of the present invention comprises a nucleic acid molecule of the present invention and expresses analogs, derivatives, and/or fragments thereof having at least one functional feature and/or structural feature of a polypeptide of the invention. In yet another preferred embodiment, a transgenic plant of the present invention comprises a nucleic acid molecule of the invention that hybridizes under stringent conditions, as defined herein, to a nucleic acid molecule having the sequence of SEQ ID NO:1 or 3, or a complement thereof, and encodes a protein or polypeptide that exhibits at least one structural and/or functional feature of the polypeptides of the invention. Specifically, the present invention provides the production of transgenic tobacco and rice that produce a neutral phytase, which contributes to improving plant physiology, such as plant growth rate and characteristics, for example, in improving the flowering response. Moreover, when these plants producing neutral phytases are fed to animals, the phytases can act on other phytate sources in the animal diet to hydrolyze phytate, releasing inorganic phosphate for animal assimilation. This reduces or obviates the need to supplement animal feed with phytase or inorganic phosphate and reduces environmental pollution problems due to the animal excretion of phosphorus. Accordingly, the invention further provides animal feed comprising the transgenic plants (particularly seeds or fruits from these transgenic plants) of the present invention.

Accordingly, the present invention also provides chimeric gene constructs for genetic modification of plants to increase their growth rate and shorten the time required for flowering by increasing the availability of phosphorus. The chimeric gene constructs comprise a sequence that encodes substantially solely for a phytase enzyme that catalyzes hydrolysis of phytate at neutral pH. Preferably such a phytase enzyme is derived from *Bacillus* bacteria. In a specific embodiment, the chimeric gene constructs comprise a nucleic acid having the sequence of SEQ ID NO:1 or SEQ ID NO:3. In another embodiment, the chimeric gene constructs comprise a nucleic acid having the sequence of SEQ ID NO:1 and/or SEQ ID NO:3 except that all or a portion of the sequence of nucleotides 241 to 480, preferably all or a portion of the sequence of nucleotides 241 to 300, of SEQ ID NO:1 and/or all or a portion of the sequence of nucleotides 100 to 339, preferably all or a portion of the sequence of nucleotides 100 to 177, of SEQ ID NO:3 are replaced by a heterologous nucleotide sequence encoding a plant signal peptide. In another preferred embodiment, the chimeric gene constructs comprise a nucleic acid molecule that encodes an analog or fragment thereof having at least one functional feature and/or structural feature of a polypeptide of the invention. In another specific embodiment, the chimeric gene constructs comprise a sequence that hybridizes under stringent conditions, as defined herein, to a nucleic acid having the sequence of SEQ ID NO:1 or 3, or a complement thereof, wherein the sequence encodes a protein or a polypeptide that exhibits at least one structural and/or functional feature of the polypeptides of the invention. Furthermore, the phytase enzymes encoded by the nucleic acid molecules contained in the chimeric gene constructs of the present invention may be any other phytases that have an optimal catalytic activity at neutral pH and, optionally have similar structural characteristics, such as having multiple calcium-binding sites, to those of the phytase enzymes of the present invention. Such phytases include, but not limited to, the following polypeptides:

Phytases from *Bacillus* sp. (Accession Nos: AAC38573, AAC31775, 7767024); phytases from *Bacillus subtilis* (Accession Nos: AAC31775, AAG17903, AAB72078, AAA87722); phytases from *Bacillus amyloliquefaciens* (Accession Nos: 7246002, 7245653); phytase from *Caulobacter crescentus* (Accession No: AAK23276); and hydrolase from *Streptomyces coelicolor* (Accession No. CAC17528).

The phytase-coding sequence is operatively linked to upstream and downstream regulatory components, preferably heterologous to the phytase sequence; for example CMV 35S promoter, which acts to cause expression of the gene (production of the enzyme) in plant cells (see Sections 6.5.1-6.5.4). When a construct containing a gene for a phytase according to this invention, is introduced into plant cells by a conventional transformation method, such as microparticle bombardment, *Agrobacterium* infection, or microinjection, the gene is expressed in the cells under the control of the regulatory sequences. The expressed phytase successfully interacts with the biosynthetic machinery that is naturally present in the plant cells to catalyze release of inorganic phosphate from phytate salts at neutral pH. By increasing the availability of inorganic phosphate, this invention also favors the growth rate of the plant, resulting in increased flowering and fruiting. Thus, the time required for the maturation of the plant and the time required for flowering is shortened. Accordingly, this invention also provides plant cells and whole plants having decreased level of phytate salts, in which the plant cells contain a chimeric gene construct according to this invention. Also provided are methods for increasing the availability of inorganic phosphate in plant cells and whole plants, comprising the step of inserting into such plant cells or the cells of such whole plants a chimeric gene construct according to this invention.

In specific embodiments, rice (see Section 6.5.3) and tobacco plant (see Section 6.5.4) were adopted as two model systems. Two chimeric constructs containing the gene coding for phytase were introduced into these two kinds of plants.

In a preferred embodiment of this invention, the phytase from *Bacillus subtilis* is used. This phytase is secreted from the cell as it contains a signal peptide for secretion. This enzyme is able to release inorganic phosphate from phytate under neutral pH and has high temperature stability. Thus, it is now discovered that a phytase from an organism in another kingdom can function effectively with essential biopathway components supplied by a plant despite the wide divergence between the gene and protein sequences and structures between the two kingdoms. Thus, this invention involves creation of a biochemical pathway in the plant that can shift phosphorus from phytate form into inorganic phosphate form. The results obtained with this invention indicate that the growth rate of plant was enhanced by this novel biochemical pathway (see Section 6.5.9 and FIGS. 12 and 13).

It has also been observed that phosphate is required for flowering. Thus, the present invention also provides transgenic flowering plants which have a shortened time for flowering due to the enhanced availability of phosphate by the expression of neutral phytase transgenes.

While any plant species can be modified using the expression cassette and methods of this invention, preferably included without limitation are species from the following genera with representative species in parentheses:

Monocots: genera Asparagus (asparagus), *Bromus* (cheatgrass), *Hemerocallis* (daylily), *Hordeum* (barley), *Lolium* (ryegrass), *Oryza* (rice), *Panicum* (witchgrass), *Pennisetum* (fountaingrass), *Sorghum, Trigonella* (fenu grass), *Triticum* (wheat), Zea (corn); and Dicots: genera *Antirrhinum* (flower sp.), *Arabidopsis* (thaliana), *Arachis* (peanut), Atropa (deadly nightshade), *Brassica* (rapeseed), *Browallia, Capsicum* (pepper), *Carthamus* (safflower), *Cichorium* (chicory), Citrus (orange, lemon), *Chrysanthemum, Cucumis* (cucumber), *Datura* (thorn apple), *Daucus* (carrot), *Digitalis* (foxglove), *Fragaria* (strawberry), *Geranium* (flower sp.), Glycine (soybean), *Helianthus* (sunflower), *Hyscyamus, Ipomoea* (morning glory), *Latuca* (lettuce), *Linum* (linseed), *Lotus* (flower sp.), *Lycopersicon* (tomato), *Majorana, Malva* (cotton), *Manihot, Medicago* (alfalfa), *Nemesia, Nicotiana* (tobacco), *Onobrychis, Pelargonium* (citrosa), *Petunia* (flower sp.), *Ranunculus* (flower sp.), *Raphanus* (radishes), *Salpiglossis, Senecio* (flower sp.), *Sinapis* (albae semen), *Solanum* (potato), *Trifolium* (clovers), *Vigna* (mungbean, faba bean), *Vitis* (grape).

Genetic engineering of plants can be achieved in several ways. The most common method is *Agrobacterium*-mediated transformation. In this method, *A. tumefaciens*, which in nature infects plants by inserting tumor causing genes into a plant's genome, is altered. Selected genes are engineered into the T-DNA of the bacterial Ti (tumor-inducing) plasmid of *A. tumefaciens* in laboratory conditions so that they become integrated into the plant chromosomes when the T-DNA is transferred to the plant by the bacteria's own internal transfer mechanisms. The only essential parts of the T-DNA are its two small (25 base pair) border repeats, at least one of which is needed for plant transformation. The bacterial genes encoding for plant hormones that promote tumor growth are excised from the T-DNA and replaced with a sequence of DNA that typically contains: a selectable marker (e.g. an antibiotic-resistance gene; usually kanamycin resistance), a restriction site—a site with a specific sequence of nucleotides where a restriction enzyme will cut the DNA, and the desired genes to be incorporated into the plant (B. Tinland, 1996. The integration of T-DNA into plant genomes. Trends in Plant Science 1, 178-184; D. Grierson (ed.) 1991. Plant Genetic Engineering. Blackie, Glasgow). *Agrobacterium* can be added to plant protoplasts (plant cells with cell walls removed) in culture, that are then allowed to regenerate cell walls at which point non-transformed plants are killed with antibiotics for which the transformed plants have been given resistance genes. Plantlets are then regenerated from the surviving transformed cells using standard plant tissue culture techniques. In an alternative technique, sterile disks or fragments of vegetative portions of plants are place in liquid culture medium with *Agrobacterium*, then hormones are used to induce rooting thereby regenerate plantlets which are grown on selection media. A third technique for delivering genes is possible for some plants such as *Arabidopsis* where the *Agrobacterium* or even "naked" DNA can be infused through the seed coat to cause transformation (Clough S J and Bent A F, 1998. Floral dip: a simplified method for *Agrobacterium*-mediated transformation of *Arabidopsis thaliana*. Plant J 16:735-43).

The biolistic method for genetic engineering of plants was developed more recently and is becoming more widely employed. In this method, very small particles (microprojectiles) of tungsten or gold coated with biologically active DNA are propelled at high-velocities into plant cells using an electrostatic pulse, air pressure, or gunpowder percussion. As the particles pass through the cell, the DNA dissolves and can then integrate into the genome of that cell and its progeny. It has been demonstrated this method can produce stable transformants (Christou, P., et al., 1988. Stable transformation of soybean callus by DNA-coated gold particles, *Plant Physiology* 87:671-674). The method can be practiced on whole plants and is particularly effective on meristematic tissue. It is also capable of delivering DNA either to the nucleus or into mitochondria (Johnston, S. A., et al., 1988. Mitochondrial transformation in yeast by bombardment with microprojectiles. Science 240, 1538-41) and chloroplasts (Svab, Z., et al., 1990, Stable transformation of plastids in higher plants, *Proc Natl Acad. Sci. USA* 87, 8526-8530).

The electroporation method of plant genetic engineering has met with less success. In this technique, protoplasts in culture take up pure DNA when treated with certain membrane-active agents or with electroporation, a rapid pulse of high-voltage direct current. Once the DNA has entered the protoplast it can be integrated into the cells genome. Standard tissue culture techniques are then used to regenerate transgenic plants.

The microinjection method of plant genetic engineering is perhaps the most difficult. In this method, DNA is microinjected into target plant cells using very thin glass needles in a method similar to that used with animals. The technique is laborious, ineffective, and impractical for generating large numbers of transgenic plants.

The method chosen for genetically engineering plants is most often dependent on the targeted plant species and which methods have been proven effective therein.

5.8 Preparation of Antibodies

Antibodies which specifically recognize a polypeptide of the invention or fragments thereof can be used for detecting, screening, and isolating the polypeptide of the invention or fragments thereof, or similar sequences that might encode similar enzymes from the other organisms. For example, in one specific embodiment, an antibody which immunospecifically binds phyL or 168phyA or fragments thereof can be used for various in vitro detection assays, including enzyme-linked immunosorbent assays (ELISA), radioimmunoassays, Western blot, etc., for the detection of the polypeptide of the invention or fragments, derivatives, analogs, or variants thereof, or similar molecules having the similar enzymatic activities as the polypeptide of the invention, in samples, for example, a biological material, including cells, cell culture media (e.g., bacterial cell culture media, mammalian cell culture media, insect cell culture media, yeast cell culture media, etc.), blood, plasma, serum, tissues, etc.

Antibodies specific for the polypeptides of the invention may be generated by any suitable method known in the art. Polyclonal antibodies to an antigen-of-interest can be produced by various procedures well known in the art. For example, an antigen derived from the polypeptide of the invention can be administered to various host animals including, but not limited to, rabbits, mice, rats, etc., to induce the production of antisera containing polyclonal antibodies specific for the antigen. Various adjuvants may be used to increase the immunological response, depending on the host species, and include but are not limited to, Freund's (complete and incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful adjuvants for humans such as BCG (*Bacille Calmette-Guerin*) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies. A Laboratory Manual*, (Cold Spring Harbor Laboratory Press, 2nd ed. 1988); Hammerling, et al., in: *Monoclonal Antibodies and T-Cell Hybridomas*, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Antibody fragments which recognize specific epitopes may be generated by known techniques. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the complete light chain, and the variable region, the CH1 region and the hinge region of the heavy chain.

The antibodies of the invention or fragments thereof can be also produced by any method known in the art for the synthesis of antibodies, in particular, by chemical synthesis or preferably, by recombinant expression techniques.

The nucleotide sequence encoding an antibody may be obtained from any information available to those skilled in the art (i.e., from Genbank, the literature, or by routine cloning). If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., supra; and Ausubel et al., eds., 1998, *Current Protocols in Molecular Biology*, John Wiley & Sons, NY, which are both incorporated by reference herein in their entireties), to generate antibodies having a different amino acid sequence by, for example, introducing amino acid substitutions, deletions, and/or insertions into the epitope-binding domain regions of the antibodies or any portion of antibodies which may enhance or reduce biological activities of the antibodies.

Recombinant expression of an antibody requires construction of an expression vector containing a nucleotide sequence that encodes the antibody. Once a nucleotide sequence encoding an antibody molecule or a heavy or light chain of an antibody, or portion thereof has been obtained, the vector for the production of the antibody molecule may be produced by recombinant DNA technology using techniques well known in the art as discussed in the previous sections. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The nucleotide sequence encoding the heavy-chain variable region, light-chain variable region, both the heavy-chain and light-chain variable regions, an epitope-binding fragment of the heavy- and/or light-chain variable region, or one or more complementarity determining regions (CDRs) of an antibody may be cloned into such a vector for expression. Thus-prepared expression vector can be then introduced into appropriate host cells for the expression of the antibody. Accordingly, the invention includes host cells containing a polynucleotide encoding an antibody specific for the polypeptides of the invention or fragments thereof. In certain embodiments, the host cell is a *Bacillus* sp., preferably *Bacillus subtilis* MU331.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides or different selectable markers to ensure maintenance of both plasmids. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, *Nature*, 322:52; and Kohler, 1980, *Proc. Natl. Acad. Sci. USA*, 77:2197). The coding sequences for the heavy and light chains may comprise cDNA or genomic DNA.

In another embodiment, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fvs, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman et al., 1995, *J. Immunol. Methods* 182:41-50; Ames et al., 1995, *J. Immunol. Methods* 184:177-186; Kettleborough et al., 1994, *Eur. J. Immunol.*, 24:952-958; Persic et al., 1997, *Gene*, 187:9-18; Burton et al., 1994, *Advances in Immunology* 57:191-280; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT publication WO 92/22324; Mullinax et al., 1992, *BioTechniques* 12(6):864-869; and Sawai et al., 1995, *AJRI* 34:26-34; and Better et al., *Science*, 240:1041-1043, 1988 (each of which is incorporated by reference in its entirety). Examples of techniques which can be used to produce single-chain Fvs and antibodies include those described in U.S. Pat. Nos. 4,946,778 and 5,258,498; Huston et al., 1991, *Methods in Enzymology* 203:46-88; Shu et al., 1993, *PNAS* 90:7995-7999; and Skerra et al., 1988, *Science* 240:1038-1040.

Once an antibody molecule of the invention has been produced by any methods described above, it may then be purified by any method known in the art for purification of an immunoglobulin molecule, for example, by chromatography (e.g., ion exchange, affinity, particularly by affinity for the specific antigen after Protein A or Protein G purification, and sizing column chromatography), centrifugation, differential solubility, or by any other standard techniques for the purification of proteins. Further, the antibodies of the present invention or fragments thereof may be fused to heterologous polypeptide sequences described herein or otherwise known in the art to facilitate purification.

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a constant region derived from a human immunoglobulin. Methods for producing chimeric antibodies are known in the art. See e.g., Morrison, *Science*, 229:1202, 1985; Oi et al., *BioTechniques*, 4:214 1986; Gillies et al., *J. Immunol. Methods*, 125:191-202, 1989; U.S. Pat. Nos. 5,807,715; 4,816,567; and 4,816,397, which are incorporated herein by reference in their entireties. Humanized antibodies are antibody molecules from non-human species that bind the desired antigen having one or more complementarity determining regions (CDRs) from the non-human species and framework regions and constant domain from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. No. 5,585,089; Riechmann et al., 1988, *Nature* 332:323, which are incorporated herein by reference in their entireties. Antibodies can be humanized using a variety of techniques known in the art including, for example, CDR-grafting (EP 239,400; PCT publication WO 91/09967; U.S. Pat. Nos. 5,225,539; 5,530, 101 and 5,585,089), veneering or resurfacing (EP 592,106; EP 519,596; Padlan, 1991, *Molecular Immunology* 28(4/5): 489-498; Studnicka et al., 1994, *Protein Engineering* 7(6): 805-814; Roguska et al., 1994, *Proc Natl. Acad. Sci. USA* 91:969-973), and chain shuffling (U.S. Pat. No. 5,565,332), all of which are hereby incorporated by reference in their entireties.

Completely human antibodies are particularly desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety.

Human antibodies can also be produced using transgenic mice which are incapable of expressing functional endogenous immunoglobulins, but which can express human immunoglobulin genes. For an overview of this technology for producing human antibodies, see Lonberg and Huszar, 1995, *Int. Rev. Immunol.* 13:65-93. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Abgenix, Inc. (Fremont, Calif.), Medarex (NJ) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., 1988, *Bio/technology* 12:899-903).

Antibodies fused or conjugated to heterologous polypeptides may be used in in vitro immunoassays and in purification methods (e.g., affinity chromatography) well known in the art. See e.g., PCT publication Number WO 93/21232; EP 439,095; Naramura et al., 1994, *Immunol. Lett.* 39:91-99; U.S. Pat. No. 5,474,981; Gillies et al., 1992, *PNAS* 89:1428-1432; and Fell et al., 1991, *J. Immunol.* 146:2446-2452, which are incorporated herein by reference in their entireties.

Antibodies may also be attached to solid supports, which are particularly useful for immunoassays or purification of the polypeptides of the invention or fragments, derivatives, analogs, or variants thereof, or similar molecules having the similar enzymatic activities as the polypeptide of the invention. Such solid supports include, but are not limited to, glass, cellulose, polyacrylamide, nylon, polystyrene, polyvinyl chloride or polypropylene.

5.9 Detection Assays

An exemplary method for detecting the presence or absence of a polypeptide or nucleic acid of the invention in a biological sample involves obtaining a biological sample from various sources and contacting the sample with a compound or an agent capable of detecting a polypeptide or nucleic acid (e.g., mRNA, genomic DNA) of the invention such that the presence of a polypeptide or nucleic acid of the invention is detected in the sample. A preferred agent for detecting mRNA or genomic DNA encoding a polypeptide of the invention is a labeled nucleic acid probe capable of hybridizing to mRNA or genomic DNA encoding a polypeptide of the invention. The nucleic acid probe can be, for example, a full-length cDNA, such as the nucleic acid of SEQ ID NO:1 or 3, or a portion thereof, such as an oligonucleotide of at least 15, 20, 25, 30, 50, 100, 250, 500, or more contiguous nucleotides in length and sufficient to specifically hybridize under stringent conditions to a mRNA or genomic DNA encoding a polypeptide of the invention.

A preferred agent for detecting a polypeptide of the invention is an antibody capable of binding to a polypeptide of the invention, preferably an antibody with a detectable label. Antibodies can be polyclonal, or more preferably, monoclonal. An intact antibody, or a fragment thereof (e.g., Fab or F(ab')$_2$) can be used. See also the detailed descriptions about antibodies in section 5.5.

The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The detection method of the invention can be used to detect mRNA, protein, or genomic DNA in a sample in vitro as well as in vivo. For example, in vitro techniques for detection of mRNA include Northern hybridizations and in situ hybridizations. In vitro techniques for detection of a polypeptide of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide of the invention include introducing into a subject organism a labeled antibody directed against the polypeptide. For example, the antibody can be labeled with a radioactive marker whose presence and location in the subject organism can be detected by standard imaging techniques, including autoradiography.

In a specific embodiment, the methods further involve obtaining a control sample from a control subject, contacting the control sample with a compound or agent capable of detecting a polypeptide of the invention or mRNA or genomic DNA encoding a polypeptide of the invention, such that the presence of the polypeptide or mRNA or genomic DNA encoding the polypeptide is detected in the sample, and comparing the presence of the polypeptide or mRNA or genomic DNA encoding the polypeptide in the control sample with the presence of the polypeptide or mRNA or genomic DNA encoding the polypeptide in the test sample.

The invention also encompasses kits for detecting the presence of a polypeptide or nucleic acid of the invention in a test sample.

The kit, for example, can comprise a labeled compound or agent capable of detecting the polypeptide or mRNA encoding the polypeptide in a test sample and means for determining the amount of the polypeptide or mRNA in the sample (e.g., an antibody which binds the polypeptide or an oligonucleotide probe which binds to DNA or mRNA encoding the polypeptide). Kits can also include instructions for use.

For antibody-based kits, the kit can comprise, for example: (1) a first antibody (e.g., attached to a solid support) which binds to a polypeptide of the invention; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a nucleic acid sequence encoding a polypeptide of the invention or (2) a pair of primers useful for amplifying a nucleic acid molecule encoding a polypeptide of the invention. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for use.

5.10 Commercial Application of Phytase and Transgenic Plants

As stated above, phytates exist in large amounts in food sources, serving as the major constituents of animal diets. However, monogastric animals, including poultry animals and fishes, are not able to utilize the phosphorus source and when it is excreted into the environment, phytate causes great pollution problems to the ecosystem. Environmental alterations may not be seen immediately, because they primarily occur at the bottom of the food chain, but as the pollution continues, the effect of these alterations will accumulate and permeate all through the ecosystem and cause permanent damage to the whole ecosystem.

Thus, the polypeptides of the invention have great commercial utility, based on their non-toxicity to monogastric animals and the mass production through the overexpression system for the polypeptides of the invention, by preparing animal feed containing the polypeptides of the invention. The polypeptides of the invention utilized by monogastric animals as feed will reduce the excretion of unutilized phosphorus into the environment and, thus, minimize the environmental pollution.

Furthermore, phosphate is commonly added to fertilizers for the enhancement of plant growth, and thus contributing to further environmental pollution. Although a phosphorus source does exist in the soil, it is locked in the form of phytate and not available to plants. Thus, the transgenic plants, with a chimeric gene construct according to the present invention, that express a phytase intracellularly and/or extracellularly have great advantages in utilizing phosphorus that is otherwise unavailable to plants themselves as well as to animals. Namely, the efficient utilization of phosphorus by the transgenic plants contributes not only to the reduction of the environmental pollution by phosphorus but also to the enhancement of plant growth, including flowering and fruiting activities, which implicate significant agricultural and horticultural applications. Furthermore, the incorporation of the transgenic plants with intracellular phytase expression of the present invention themselves into animal feed further contributes to the availability of phosphorus to animals, whose wastes cause less pollution to the environment.

EXAMPLES

The following examples illustrate the cloning, production, isolation, and characterization of the phytase and antibodies. These examples should not be construed as limiting.

6.1 The Molecular Cloning of phyL Gene

Figure 3:
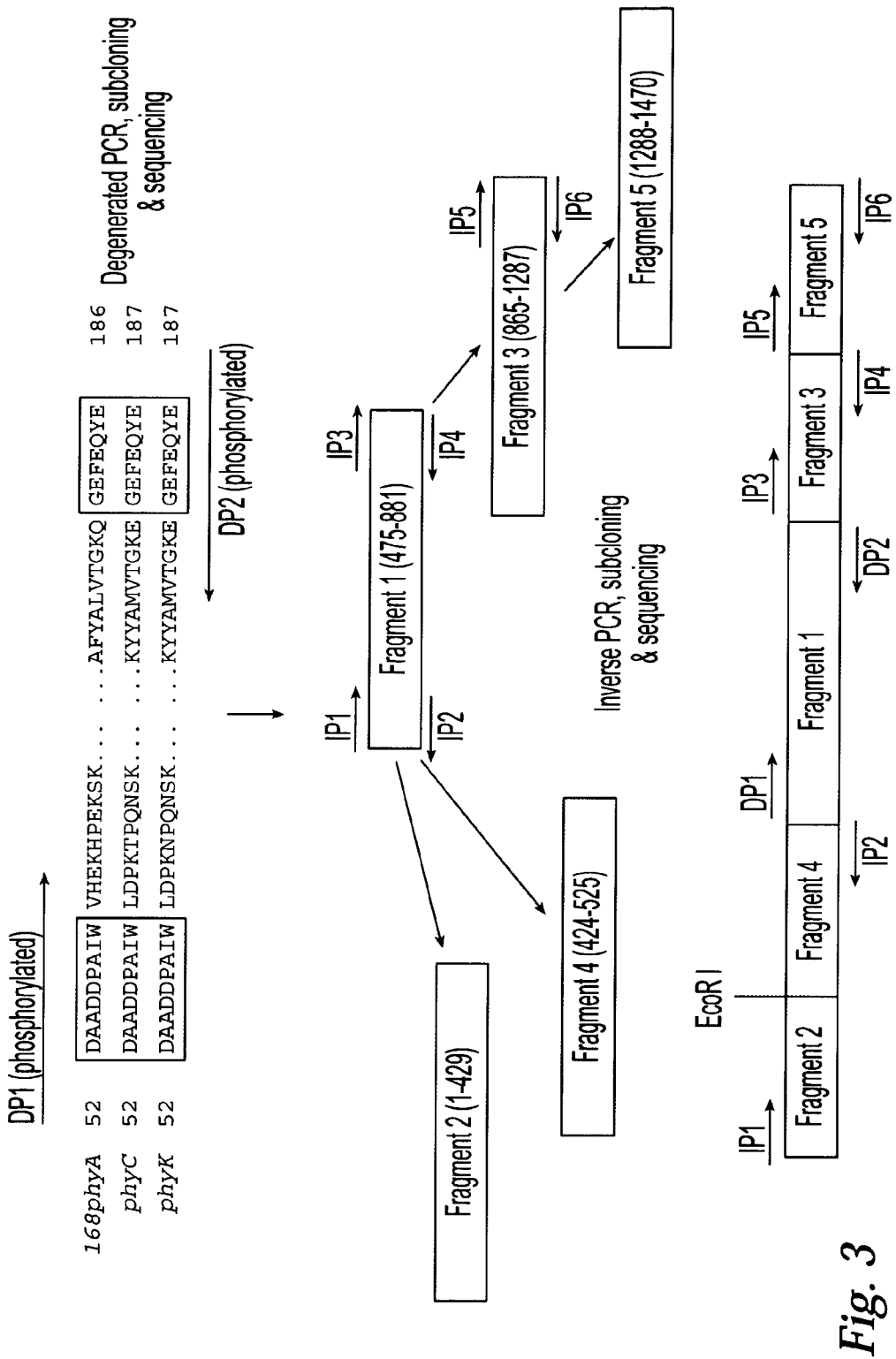
FIG. 3 represents the strategy for PCR cloning of phyL gene. DP represents degenerated primers for degenerate PCR, IP represents inverse PCR primers. Degenerated primers were designed based on the conserved amino acid sequences, DAADDPAIW (SEQ ID NO:25) and GEFEQYE (SEQ ID NO:26), found in the regions of 168phyA (residues 52-70, SEQ ID NO:27; and residues 170-186, SEQ ID NO:30), phyC (residues 52-70, SEQ ID NO:28; and residues 171-187, SEQ ID NO:31) and phyK (residues 52-70, SEQ ID NO:29; and residues 171-187, SEQ ID NO:32). The phyL gene was cloned by degenerated PCR followed by inverse PCR in subsequent steps. Fragments by inverse PCR were aligned and the whole gene was cloned from the upstream region (5' to the ATG translation initiation codon) to the stop codon of the gene.

The strategy of cloning the phyL gene from *B. licheniformis* was shown in FIG. 3. *Bacillus licheniformis* cells were obtained commercially (ATCC # 10716). Bacterial cells were grown on nutrient agar plate (2.5% [w/v] nutrient broth powder, 1.5% [w/v] bacteriological agar) at 37° C. and served as the templates for degenerated PCR reactions. Degenerated oligonucleotides (SEQ ID No:5 and SEQ ID No:6) were designed according to the conserved amino acids of PhyK (Kim Y. O., Lee J. K., Kim H. K., Yu J. H., Oh T. K., 1998, Cloning of the thermostable phytase gene (phy) from *Bacillus* sp. DS11 and its overexpression in *Escherichia coli, FEMS Microbiology Letters* 162:182-191) and PhyC (KerovuoSep. 25, 2002, J., Lauraus M., Nurminen P., Kalkkinen N., Apajalahti J., 1998, Isolation, characterization, molecular gene cloning, and sequencing of a novel phytase from *Bacillus subtilis, Applied and Environmental Microbiology* 64(6):2079-2085), and 168phyA (SEQ ID No:4) and served as primers for the PCR reactions. Amplification was carried out in a PCR machine (Robocycler gradient 40, Stratagene, USA) for 30 cycles of {45 sec at 94° C., 45 sec at 50° C., 2 min 30 sec at 72° C.} with phosphorylated oligos. Desired PCR product was excised from a 2% (w/v) agarose gel and purified by Geneclean III kit (Qbiogene, Inc, CA). The purified product was cloned into pBSSK, induced by X-gal/IPTG, and selected for ampicillin resistance. Plasmids of the positive clones cultured in LB broth supplemented with 100 μg/ml ampicillin were extracted using the Quantum mini-prep kit (Bio-Rad, Hong Kong) and sequenced (MWG Biotech AG, Germany).

The genomic DNA of *B. licheniformis* was extracted by the Genomic DNA purification kit (Promega, Hong Kong) and the DNA concentration was determined by UV photometric analysis at 260 nm. Two sets of genomic DNA (20 μg each) were subjected to partial restriction enzyme digestion for one hour by 10 units of Hae III (Boehringer Mannhem, Hong Kong) and 10 units Sau3AI (Boehringer Mannhem, Hong Kong) respectively. Digested DNA was purified and diluted to 1 μg/ml, followed by circularization using T4 DNA ligase (Life Technologies, Hong Kong). Circularized DNA was purified by phenol-chloroform extraction and ethanol precipitation.

Forward and reverse oligonucleotides (SEQ ID NOS:7-12) were designed to flank the 5' and 3' ends of the sequence generated from degenerated PCR. Inverse PCR was performed with 30 cycles of {45 sec at 94° C., 45 sec at 55° C., 2 min at 72° C.} using the partially digested genomic DNA as templates. Positive PCR products were ethanol-precipitated and digested with the corresponding restriction enzymes (Boehringer Mannhem, Hong Kong) before subcloning into the Eco RI and Bam HI sites of pBSSK. Positive clones were selected and extracted as described above. The clones were sequenced and sequence data were assembled and analyzed by DNA processing softwares including MAC DNASIS (Hitachi, Japan) and DNA Strider (Christian Marck, Service de Biochimie, Department de Biologie, Institut de Recherche Fondamentale, CEA, France). Phylogenetic analysis was done by GeneWorks for Mac (Intelligenetics, Mountain View, Calif.).

The DNA and deduced amino acid sequences of phyL are shown in SEQ ID NOS:1 and 2, respectively. A putative ribosomal binding site with a consensus sequence GGAGG was found 12 bp upstream of the start codon ATG. The amino acid sequence deduced from the nucleotide sequence revealed a protein of 381 amino acid residues, which are shorter than the other three *B. subtilis* phytases. The DNA sequence and its deduced amino acid sequence were compared to NCBI database with BLAST search. It was found that phyL had 65.7% identity with phyK, 66.8% identity with phyc, and 68.7% identity with 168phyA in protein level while it had 64.7% identity with phyk, 66.3% identity with phyC, and 67.8% identity with 168phyA in DNA level. Similar to the three *B. subtilis* phytases, phyL encoded phytase does not possess the highly conserved RHGXRXP sequence motif that occur in all identified fungal and *E. coli* phytases.

6.2 Over-Expression of Phytases Encoded by phyL

Figure 4A:
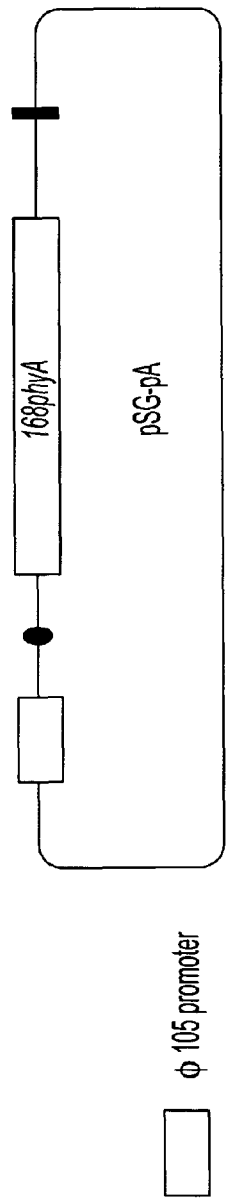
FIGS. 4A and 4B show the constructs of expression vectors for phytase overproduction. An expression plasmid for *B. subtilis* 168 phytase overexpression is shown in (A). The construct carries the φ105 promoter, followed by a Shine-Delgarno (SD) sequence, the native 168phyA gene and its native terminator. An expression plasmid for *B. licheniformis* phytase overexpression is shown in (B). The construct carries the φ105 promoter, followed by an SD sequence, the native phyL gene and the terminator of the α-amylase gene from *B. licheniformis*.
Figure 4B:
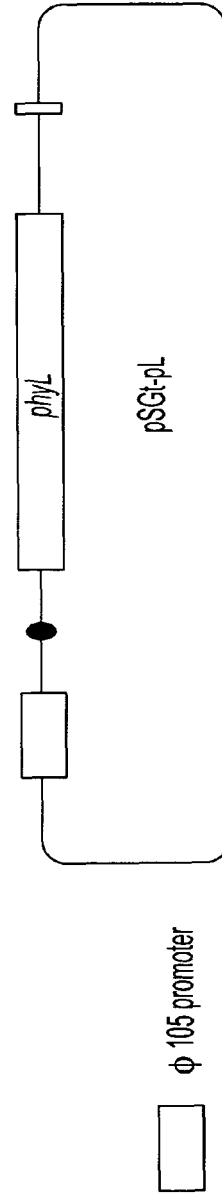

PCR primers (SEQ ID NOS:13 and 14) were designed to flank the coding region from the translation codon ATG through the stop codon of the phyL gene. The gene fragment encoding the mature enzyme was amplified by Pfu polymerase (Promega, Wis.) and sub-cloned into the expression vector pSGt, which is constructed by subcloning the terminator of the α-amylase gene of *B. licheniformis* into the expression vector pSG. Hence, the phyL gene is under the control of the φ105 prophage promoter. This vector is designated as pSGt-pL (FIG. 4B).

Plasmids were introduced into *E. coli* strain JM109 by electroporation. Bacterial colonies were screened for ampicillin resistance and positive clones were extracted and purified using the Quantum Mini-prep Kit (BIO-RAD, Hong Kong).

For the transformation of recombinant plasmids into the host strains for enzyme production, competent *Bacillus subtilis* MU331 cells were prepared by the method described by Osborne et al. (Osburne M. S. Craig R. J. and Rothstein D. M., 1985, Thermoinducible transcription system for *Bacillus subtilis* that utilizes control elements from temperate phage φ105, *J. of Bacteriology* 16:1101-1108). The transformants were screened by separately plating them on agars supplemented with chloramphenicol and erythromycin. Colonies with resistance to both antibiotics were further screened by PCR with φ105-specific primer and a primer specific for phyL (SEQ ID NO:14). A recombinant strain, pL-01, used in the enzyme characterization studies, was created in this manner and was frozen in 30% (v/v) glycerol at −80° C.

The medium of bacterial cultivation and enzyme production is as follows:

Brain heart infusion broth consisting of:

| | |
|---|---|
| Calf brain infusion solids | 12.5% |
| Beef heart infusion solids | 5% |
| Protease peptone | 10% |
| Glucose | 2% |
| Sodium chloride | 5% |
| Di-sodium phosphate | 2.5% |
| Yeast extract at neutral pH | 2.5% |

Strain pL-01 was streaked onto LB agar plates supplemented with 5 µg/ml chloramphenicol. In the following day, a single colony was picked and transferred into bacterial cultivation media supplemented with 5 µg/ml chloramphenicol. The cells were cultured with shaking at 280 rpm until the $OD_{600}$ reading reached 7.0. One (1) ml of culture was transferred to 15 ml bacterial cultivation media without antibiotics. The cells were grown to $OD_{600}$ 4.5 and heat-induced in a 50° C. water bath for 5 minutes with vigorous shaking. Samples were taken at different time points after the induction.

All enzyme purification steps were carried out at 0° C. to 4° C. unless otherwise stated. Bacteria grown in bacterial cultivation medium were collected by centrifugation at 3000 rpm for 30 minutes. The collected supernatants were mixed with 3 volumes of cold (−20° C.) ethanol and precipitated with stirring at 4° C. overnight. After the precipitate was collected by centrifugation at 6000 rpm for 30 minutes, it was air dried and resuspended in 100 mM Tris-HCl, pH 7, containing 5 mM $CaCl_2$. Resuspended enzyme was run through NAP-10 Sephadex gel-filtration column (Marsha Pharmacia, Hong Kong) for buffer exchange. The enzyme eluted with the pre-designed assay buffer was kept at −20° C. until enzyme assays were performed.

Figure 5B:
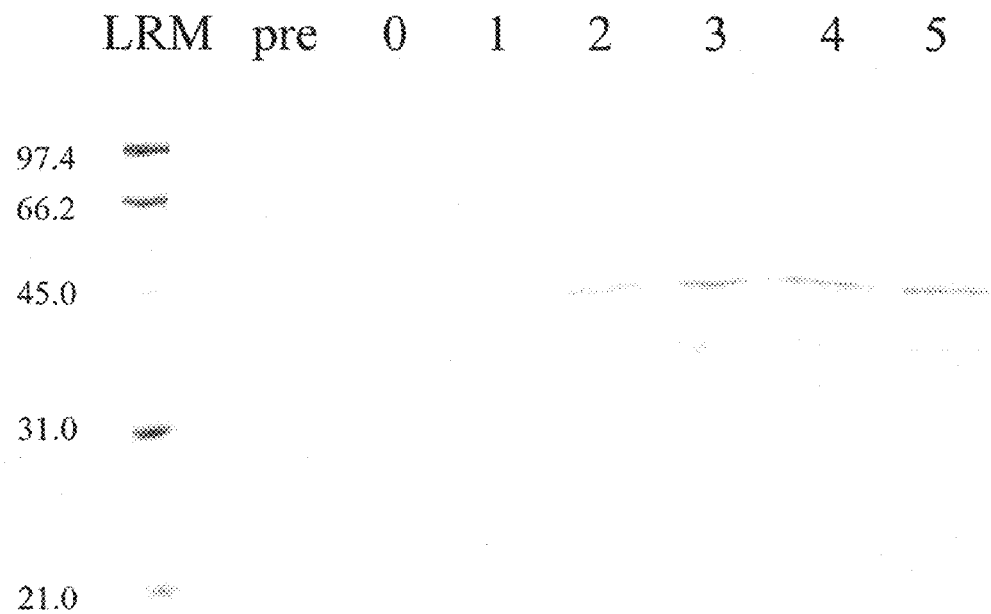
Figure 6A:
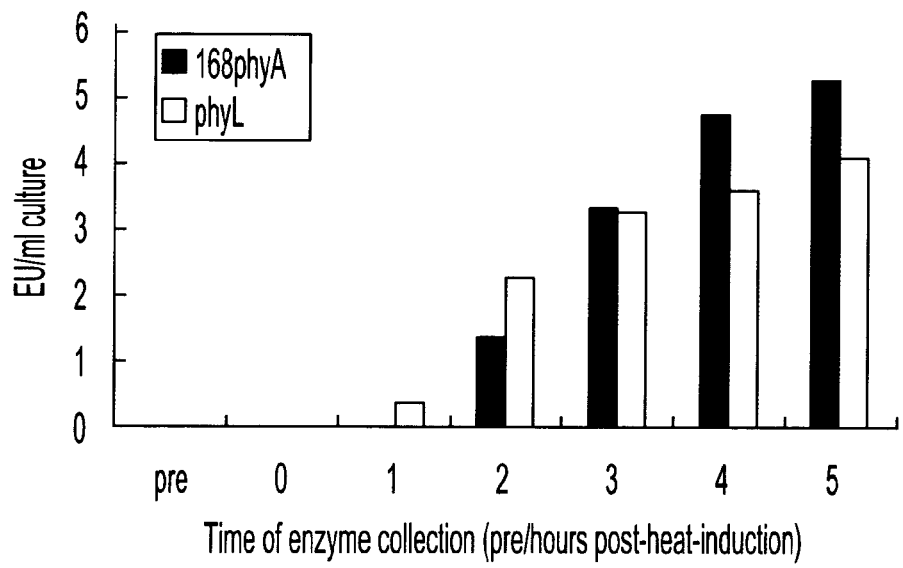
FIGS. 6A and 6B show the enzyme activities of the two phytases. (A) estimates enzyme activity in terms of enzyme units per ml culture collected, and (B) represents enzyme activity in terms of enzyme units per mg of enzyme applied in each individual reaction.
Figure 6B:
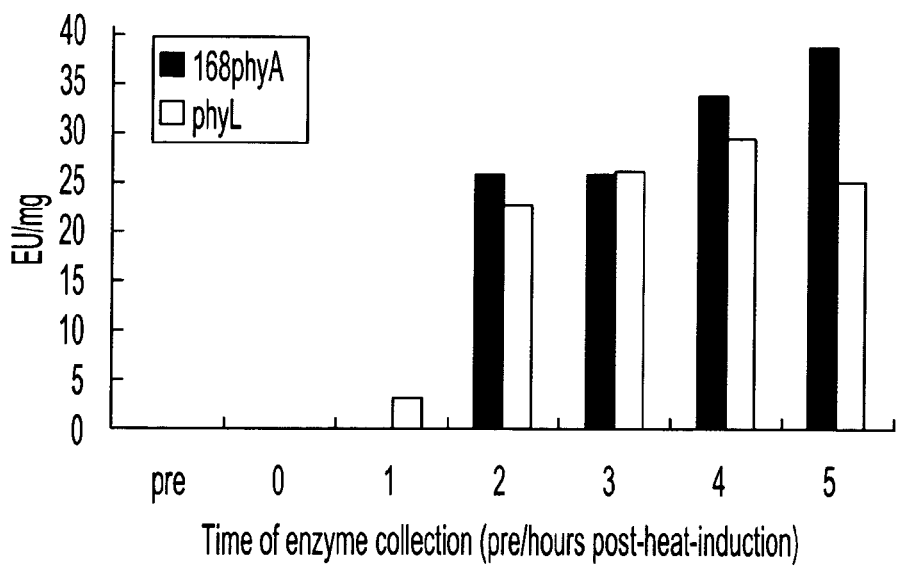

The molecular mass of the mature phytase encoded by phyL was about 47 kDa as determined by SDS-PAGE (FIG. 5B). The production of phytase encoded by phyL was found to reach 175 mg/L in the collection of 5 hours post-heat induction. The enzyme activity reached 4.1 units per ml of culture and 23.6 units per mg of enzyme used, where one unit of enzyme activity is defined as the amount of enzyme required to liberate one µmol inorganic phosphate per minute under given assay conditions (FIG. 6). When compared to *Bacillus* phytase activities measured in previous studies (Powar and Jagannathan, 1982, Purification and properties of phytate-specific phosphatase from *Bacillus subtilis, J. of Bacteriology* 151(3): 1102-1108), the novel phyL enzyme of the present invention was produced with 17-fold increase in enzyme activity within 14-fold less cultivation time. The isoelectric point of the enzyme, as determined by two-dimensional SDS-PAGE, was found to be about 5.1.

6.3 Production of 168phyA-Encoded Phytase and its Activity

By searching sequence homology in the *Bacillus subtilis* genomes, an open reading frame (ORF) sharing high sequence homology to two published phytases in *Bacillus subtilis* were found in the genome of *B. subtilis* 168. PCR primers (SEQ ID NOS:15 and 16) were designed to amplify the gene fragment flanking this ORF and the PCR product was sub-cloned into the expression vector pSG to create pSG-pA. In this construct, the 168phyA gene was flanked by the φ105 promoter and the native terminator of the 168phyA gene (FIG. 4A). The plasmid pSG-pA was transformed into the competent *Bacillus subtilis* strain MU331 as described in Section 6.2, supra, to create a recombinant strain pA-01. Positive clones were screened by PCR with a φ105-specific primer and a primer specific for 168phyA (SEQ ID NO:16). It was then used for enzyme production as described in Section 6.2, supra.

The molecular mass of the expressed mature phytase encoded by 168phyA was 44 kDa, as determined by SDS-PAGE (FIG. 5A), which confirmed the mass calculated from the amino acid sequence (SEQ ID NO:4). The production of phytase encoded by 168phyA was found to reach 246.2 mg/L in the collection of 4 hours post-heat induction. The enzyme activity reached 5.3 units per ml culture and 36.8 units per mg of enzyme used (FIG. 6). When compared to *Bacillus* phytase activities measured in previous studies (Powar and Jagannathan, 1982, supra), the novel 168phyA enzyme of the present invention was produced with 22-fold increase in enzyme activity within 18-fold less cultivation time. The isoelectric point of the enzyme was about 5.0.

To enhance the yield of enzyme production, a two-liter (2-L) scale fed-batch fermentation was carried out on the strain pA-01. In this fermentation process, addition of carbon source (glucose) and nitrogen source (tryptone) were controlled by a pH-stat method. At 6 hours post-induction, the enzyme activity reached 28 EU/ml culture, which was a 5-fold increase when compared to that generated from the simple shake flask culture described above.

6.4 Determination of Phytase Activities

Enzyme activity assays were performed in defined buffers at various pH and temperature. Buffers used for pH test included 100 mM Citrate-HCl, pH 3.5 and 6.5; 100 mM Acetate-HCl, pH 4.5-6.0; 100 mM Tris-HCl, pH 7-8.5; 100 mM Glycine-NaOH, pH 9, 9.5; and 10.5. All the buffers listed above are supplemented with 5 mM $CaCl_2$. Enzyme concentration was determined by standard Bradford protein assay (BIO-RAD, Hong Kong) on a microassay scale. The purified enzyme was diluted in assay buffers and the colorimetric assay was performed as described by Engelen et al. (1994, supra), except that the assay was scaled down to 1 ml. Briefly, the enzyme was diluted in a total volume of 200 µl in the various defined assay buffers. To the enzyme, 0.4 ml of sodium phytate constituted in distilled water to 10 mM was added and the mixture was incubated at 55° C. or 65° C. for 168phyA- and phyL-encoded phytases, respectively, for 30 minutes. To quench the enzyme activity, 0.4 ml of a freshly prepared stop solution was added to the reaction. Five minutes later, 200 µl of the quenched mixture was transferred to a 96-well ELISA plate (Nunc, Denmark) for optical density measurement at 405 nm.

Figure 7B:
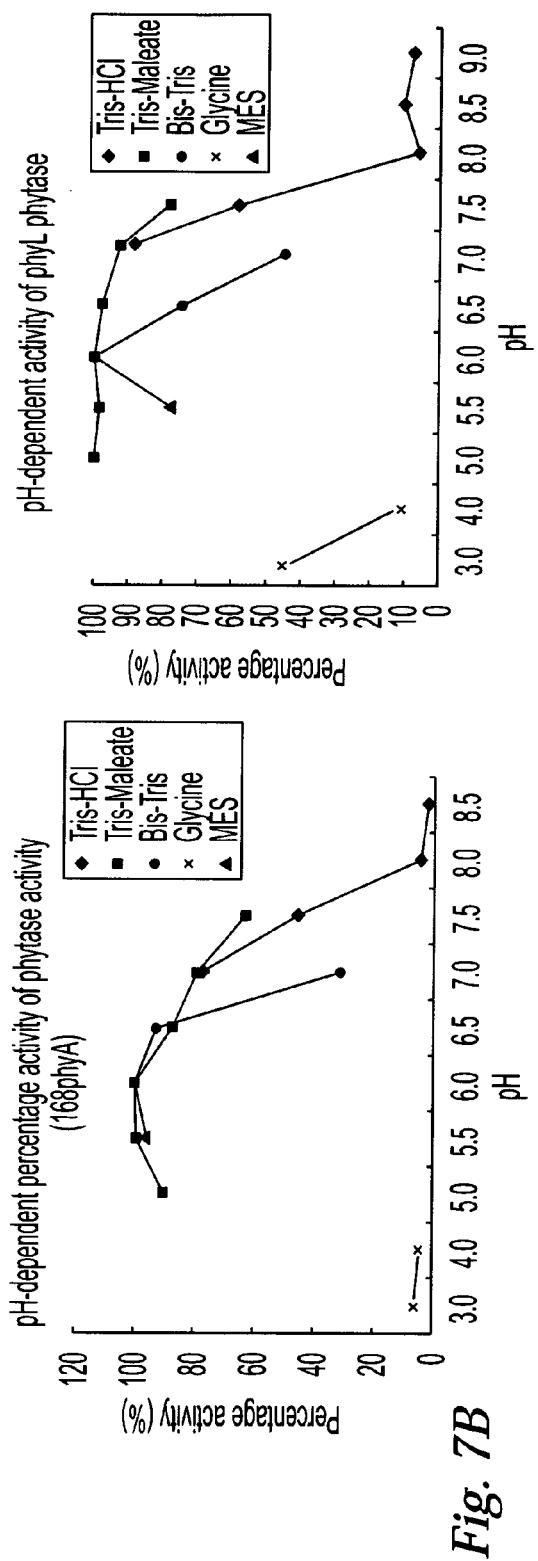

Temperature tests (FIG. 7A) carried out at neutral pH showed that both 168phyA- and phyL-encoded phytases exhibit a broad range of optimal temperature, with activity peaking at 65° C. for phyL-encoded phytase and 55° C. for 168phyA-encoded phytase. FIG. 7B shows the effect of pH on phytase activities in defined assay buffers (as described above) at the respective temperature optima. Both phytases exhibit highest activity at neutral pH.

For enzyme thermostability tests, diluted aliquots of the enzyme were incubated at different high temperatures, ranging from 70° C. to 90° C. for 10 minutes, and cooled down at room temperature for 1 hour to allow the protein refolding before the activity tests actually took place.

The phyL-encoded phytase was found to be able to recover 60-70% of its normal activity after denaturation at high temperatures, even at a low $Ca^{2+}$ concentration (1 mM). It could withstand denaturation at even up to 95° C., at which it still retained more than 50% of its original activity.

The *B. subtilis* 168phyA-encoded phytase was able to recover 50-60% of its original activity after denaturation at high temperatures at a high $Ca^{2+}$ concentration (5 mM). It could withstand a temperature at even up to 95° C., at which it still retained 46.7% of its original activity. However, 168phyA was found to retain about 20% less activity at a low $Ca^{2+}$ concentration (1 mM) than at 5 mM $Ca^{2+}$ concentration.

6.5 Generation of Transgenic Plants

Rice is an important crop worldwide especially in Asia. In China, rice accounts for 42% of the total crop grain production and 29% of the planting area. Rice is a monocot and, depending on weather and growing conditions, some tropical varieties can complete up to 3 life cycles in one year. From seedling to flowering, it will take about 60 days when the growing temperature is above 24° C. and a light period is longer than 14 hours. From flowering to seed harvesting, it will take another 30 days. In general, one rice plant gives about 500 seeds when it completes one life cycle.

Tobacco is a good model system in plant transformation because of its high transformation rate and ease of propagation in tissue cultures. Tobacco is a dicot plant recognized by its broad leaves, which have high commercial value. Tobacco is an annual plant that can complete the life cycle in 120 days. From seedling to the first flower, it will take about 96-100 days when the growing temperature is above 22° C. and a light period longer than 14 hours. Twenty to thirty fruits can be obtained in one tobacco plant; each fruit weighs about 0.3-0.4 g and contains more than a thousand seeds. In general, a tobacco plant will bear viable seeds 30 days after the blooming of the first flower.

By introducing the chimeric construct containing a gene for a phytase of the present invention into plant cells, such as rice and tobacco cells, the plants can increase their growth rates due to the increased availability of inorganic phosphate stored in the plant and/or in the soil and, thereby, shorten the time for maturity and flowering.

6.5.1 Construction of Plant Expression Vectors

Figure 8:
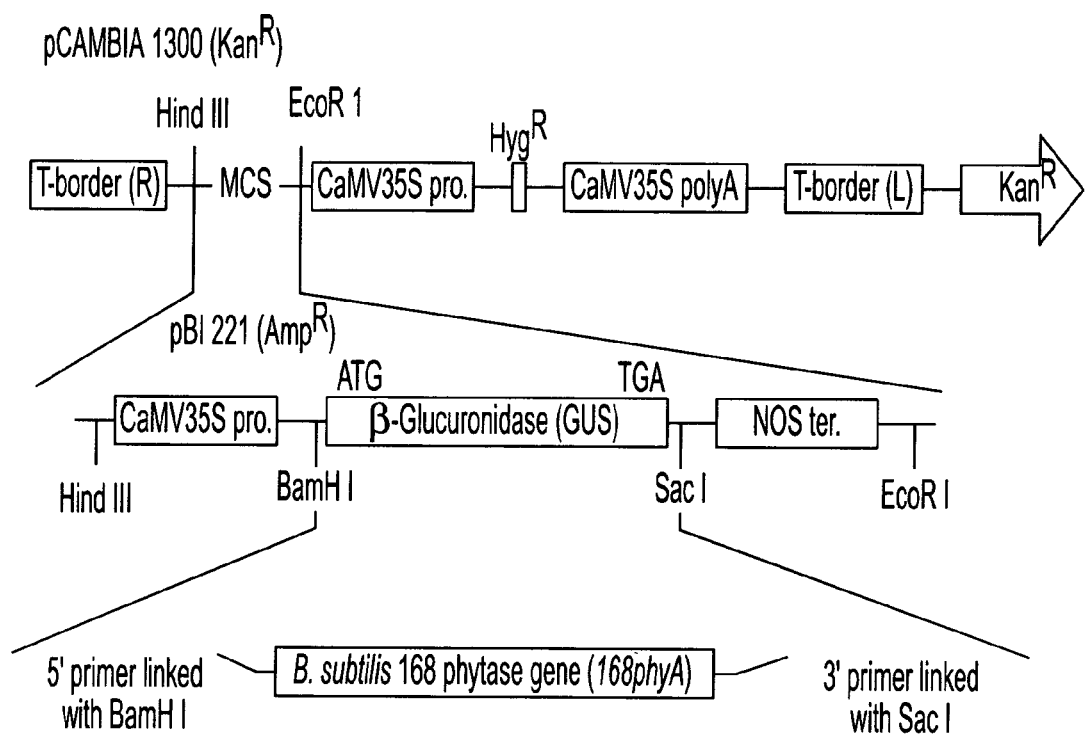
FIG. 8 is the strategy for the construction of the plant expression vector. The 168phyA gene, with its native signal peptide excluded, is cloned into the BamHI and SacI sites of the vector pBI221, replacing the E. coli β-D-glucuronidase (GUS) gene. A HindIII/EcoRI fragment carrying the 168phyA gene cassette was then released from pBI221 plasmid and subcloned into the HindIII and EcoRI sites of the binary vector pCAMBIA 1300 to generate the recombinant clone pCX0168phyA.
Figure 9:
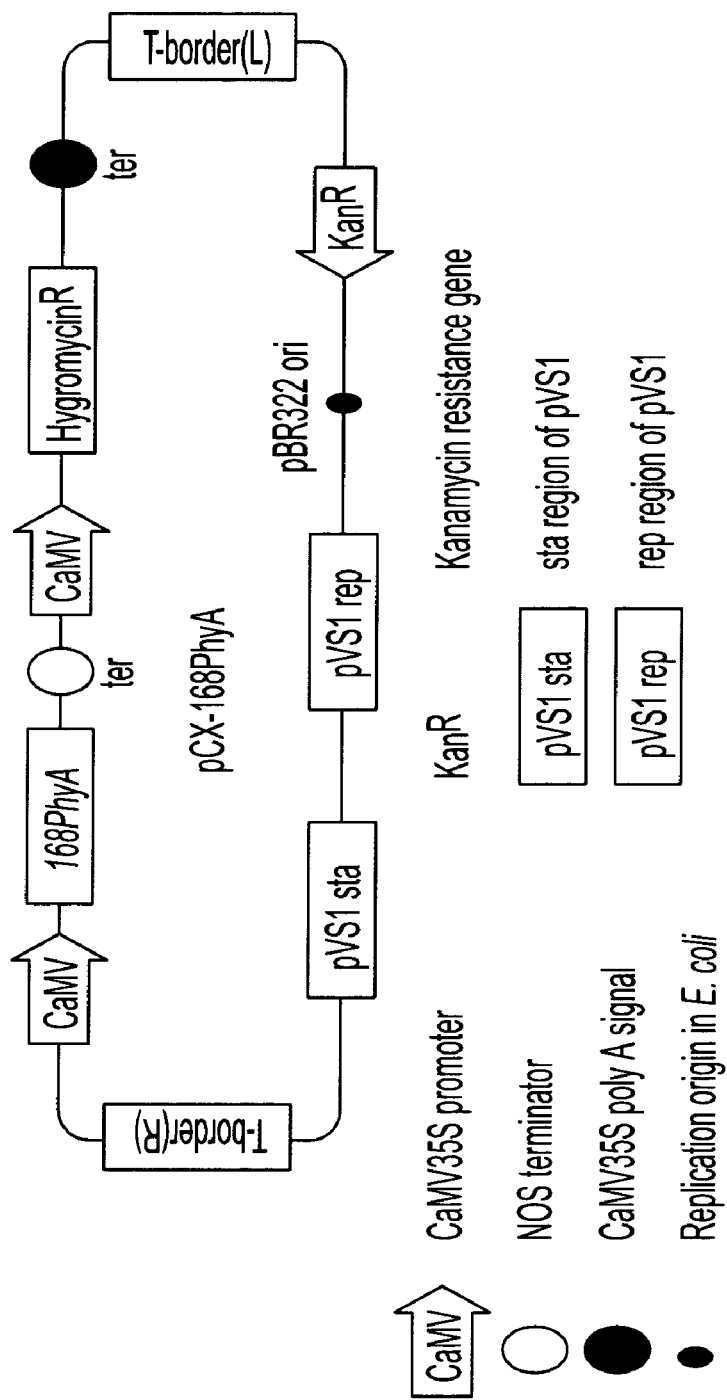
FIG. 9 is the schematic diagram of the expression vector pCX168phyA. 168PhyA: phytase gene from B. subtilis strain 168; CaMV: 35S promoter of the cauliflower mosaic virus; CaMV35S poly A signal: polyadenylation signal from the cauliflower mosaic virus 3'UTR; $Kan^R$: kanamycin resistance; NOS: Nopaline synthase gene; pBR322 ori: replication origin from pBR322; pVS1-REP: replication origin from pVS1; pVS1-STA: STA region from pVS1 plasmid; T-border(L): left border T-DNA repeat; T-border(R): right border T-DNA repeat. The presence of rep and sta regions from pVS1 (Hajdukiewicz et al., 1994, *Plant Molecular Biology*, 25:989-994) enhances the stability of these vectors in *Agrobacterium* even if grown under non-selective media.

The strategy for the construction of the plant expression vector is shown in FIG. 8. The 168phyA gene (SEQ ID NO:3) was amplified by PCR using a pair of primers that flank the gene (SEQ ID NOS:17 and 18). The *E. coli* β-D-glucuronidase (GUS) gene of the pBI221 vector (Clontech laboratories, Inc., CA) was replaced with the 168phyA gene at the BamHI and SacI restriction sites to gain the phyA-221 inter-vector. The binary vector pCAMBIA 1300 (Genebank accession number AF234296) bearing a hygromycin resistant gene driven by a CaMV 35S promoter for plant selection was digested with Hind III and EcoRI and ligated with HindIII/EcoRI linearized phyA-221 inter-vector, resulting in the new expression constructs pCX-168phyA (FIG. 9).

6.5.2 *Agrobacterium* Culture and Transformation

Two individual pCX-168phyA clones (clones 04 and 13) were transformed into *Agrobacterium tumefaciens* EHA 105 by the freezing transformation method of Höfgen and Willmitzer (1988, Storage of competent cells for *Agrobacterium* transformation, *Nucleic Acids Res.* 16:9877). A single colony was inoculated into 20 ml LB liquid medium containing 50 µg/ml kanamycin, 25 µg/ml chloramphenicol, and 50 µg/ml rifampicin, incubated at 28° C. with fast shaking for 2 days until the OD600 nm of culture suspension was about 0.8-1.0. The culture was centrifuged at 4000 rpm for 10 minutes and the pellet was resuspended in 20 ml of AAM medium (see Table 1, infra) for plant transformation.

6.5.3 Generation of Transgenic Rice

Experiments were carried out using a cultivated line, Zhonghua 11, of the japonica rice *Oryza sativa* L. Mature seeds were sterilized and germinated onto N6D medium for 2 weeks. Calluses induced from the scutellum were subcultured onto N6D medium for additional 1 week. Three-week-old calluses were soaked in the bacterium suspension for 20 minutes and the excess bacteria were absorbed with sterile filter paper. The calluses attached with the bacteria were transferred onto a piece of filter paper placed on the N6DC medium and co-cultured in the dark at 25° C. for 3 days. After the cocultivation, the infected calluses were washed with AAD medium (see Table 1, infra) containing 500 mg/L carbenicillin for 3 times, dried with sterile filter paper, and then transferred to N6DS1 medium (see Table 1, infra).

The calluses were cultured on N6DS1 medium for 2 weeks and then transferred onto N6DS2 medium (see Table 1, infra) for further selection for 3-4 weeks. The resistant calluses were transferred onto HIGROW medium (see Table 1, infra) for pre-differentiation in the dark for 10 days and then transferred individually onto MSRS medium (see Table 1, infra) for shoot regeneration in a growth chamber at 24° C. to 26° C., with 16 hours of light at 120 $\mu molm^{-2}s^{-1}$ photon flux density from fluorescent tube. Regenerated plants were transferred to MSCN medium (see Table 1, infra) for further growth. When the resistant plants are about 10 cm high, they were transferred into soil and grown to maturity in a greenhouse.

6.5.4 Generation of Transgenic Tobacco

The seeds of a cultivated tobacco variety "GeXin No 1" (*Nicotiana tobacum*) were sterilized with 30% (v/v) Clorox for 15 minutes, washed with sterile water five times and germinated on the Murashige and Skoog basal medium (MS medium; Sigma M-9274, St. Louis, Mo.). Seedlings were cultured in vitro on the same medium and grown at 22° C. in a 16-hour light/8-hour dark photo-period and at 50 $\mu molm^{-2}s^{-1}$ photon flux density provided by fluorescent tubes.

A single colony of *Agrobacterium* EHA105 containing the desired gene was inoculated into 20 ml of LB liquid medium supplemented with 50 µg/ml kanamycin, 25 µg/ml chloramphenicol, and 50 µg/ml rifampicin and cultured at 28° C. with fast shaking for 2 days. Leaves of tobacco were cut into small pieces of about 1 cm squares and dipped into the 20 ml bacteria suspension for 2-3 minutes. After removing the excess bacteria with sterile filter paper, the explants were transferred onto MS medium (see Table 1, infra) supplemented with 2 mg/L 6-BA (MSB medium) for 2 days at 25-26° C. in the dark. After 2 days of co-cultivation, the explants were transferred onto MSB medium supplemented with 30 mg/L hygromycin and 500 mg/L carbenicillin for shoot regeneration for 3-4 weeks at 26° C. in the stand light conditions. Resistant shoots were excised when they were approximately 1 cm long and transferred to MS medium supplemented with 25 mg/L hygromycin and 200 mg/L carbenicillin for rooting. While the resistant plants were about 8 cm high, they were transferred into soil and grown to maturity in a greenhouse. Four plants were produced from each pCX-168phyA clone (004 and 013) and were named 0041, 0042, 0043, 0044 and 0131, 0132, 0133 and 0134, respectively.

TABLE 1

Media used for tissue culture and transformation of plant

| Medium | Composition |
|---|---|
| N6D | N6[1], 500 mg/L casein, 30 g/L sucrose, 2.5 mg/L 2,4-D, 2.5 g/L phytagel, pH 5.7 |
| N6DC | N6D medium plus 10 g/L glucose, 100 µmol/L acetosyringone, pH 5.2 |
| AAM | AA[2], 500 mg/L casein, 68.5 g/L sucrose, 36 g/L glucose, 200 µmol/L acetosyringone, pH 5.2 |
| AAD | AA, 30 g/L sucrose, 2 mg/L 2,4-Dichlorophenoxyacetic acid (2,4-D), pH 5.7 |
| N6DS1 | N6D medium plus 500 mg/L cefotaxime and 25 mg/L hygromycin |
| N6DS2 | N6D medium plus 300 mg/L cefotaxime and 50 mg/L hygromycin |
| HIGROW | Medium (Gibco BRL 10924-017) plus 2.5 g/L phytagel |
| MSRS | MS medium[3] (sigma M-9274) plus 2 mg/L 6-Benzylaminopurine (6-BA), 0.2 mg/L α-Naphthalene acetic acid (NAA), 0.5 mg/L Zeatin (ZT), 200 mg/L cefotaxime and 50 mg/L hygromycin, pH 5.8 |
| MSCN | MS medium plus 0.2 mg/L NAA and 0.5 mg/L Chlorocholine chloride (CCC) |

[1]Zhu Z-Q, Wang J-J, Sun J-S, Xu Z, Yin G-C, Zhu Z-Y, Bi F-Y, 1975, Establishment of an efficient medium for anther culture of rice through comparative experiments on the nitrogen sources, Sci Sin 18:659-668. (English Abstract).
[2]Hiei Y, Ohta S, Komari T, Kumashiro T., 1994, Efficient transformation of rice (*Oryza sativa* L.) mediated by *Agrobacterium* and sequence analysis of the boundaries of the T-DNA, Plant J 6:271-282.
[3]Murashige T. and Skoog F., 1962, A revised medium for rapid growth and bioassay with tobacco tissue culture, Plant Physiol. 15:473-479.

The clones of the transgenic tobacco were characterized and described in the following section.

6.5.5 DNA Preparation and PCR Analysis

PCR was used to detect specific DNA sequence of the hygromycin B resistance gene. Genomic DNA from transformed and non-transformed (control) plant leaves was prepared by the following method: Plant leaves were weighted and frozen in liquid nitrogen before homogenization. To 50 mg plant tissue, 600 µl extraction buffer (100 mM Tris-HCl, pH 8.0, 50 mM EDTA, 500 mM NaCl and 10 mM β-mercaptoethanol) was added and the mixture was boiled for 10 minutes. The mixture was cooled on ice and then centrifuged at 16000 g for 15 minutes. Plant genomic DNA in the supernatant was then precipitated with 0.1 volume of 10 M ammonium acetate and 2.0 volume of absolute ethanol at −20° C. for 2 hours. The genomic DNA was then pelleted by centrifugation at 16000 g for 30 minutes. The DNA pellet was subsequently washed with 75% (v/v) ethanol before redissolved in water. Typically, 50 µg plant genomic DNA can be obtained from 0.1 g plant tissue.

Figure 10A:
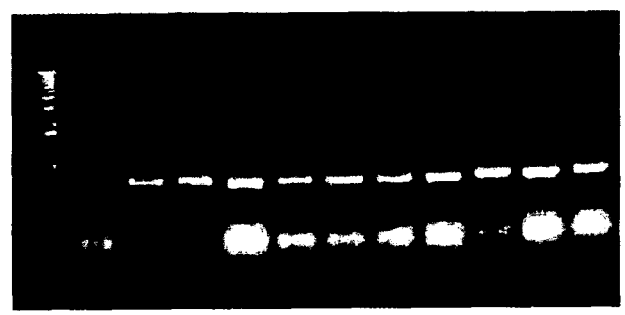
FIGS. 10A and 10B show the screening of hygromycin gene(A) and 168phyA gene(B), respectively, in transgenic tobacco. (A) Lane 1:1 KB plus DNA ladder; Lane 2: Untransformed tobacco as negative control; Lanes 3-4: Transgenic tobacco transformed with the vector pCAMBIA 1300 only (controls); Lanes 5-8: Transgenic tobacco lines of 004 (0041, 0042, 0043, 0044); Lanes 9-12: Transgenic tobacco lines of 013 (0131, 0132, 0133, 0134). (B) Lane 1:1 KB marker; Lanes 2-3: Plasmid pCX-168phyA control as positive control; Lane 4: Untransformed tobacco as negative control; Lanes 5-6: Transgenic tobacco transformed with the vector pCAMBIA 1300 only (controls); Lanes 7-10: Transgenic tobacco lines of 004 (0041, 0042, 0043, 0044); Lanes 11-14: Transgenic tobacco lines of 013 (0131, 0132, 0133, 0134).
Figure 10B:

The PCR reaction consisted of 30 cycles of {30 sec at 94° C. for denaturation, 40 sec at 56° C. for annealing, and 60 sec at 72° C. for extension}. The forward and reverse primers for the hygromycin resistance gene were: 5'-CTA-CAAAGATCGTTATGTTTATCGGCA-3' (SEQ ID NO:19) and 5'-AGACCAATGCGGAG-CATATACG-3' (SEQ ID NO:20), respectively and a fragment of 641 bp from 162 to 803 of the sequence of hygromycin resistance gene (E00287) was amplified. The forward and reverse primers (SEQ ID NOS:17 and 18) were used for the amplification of 168phyA gene. The results of the PCR screening for the transgenic tobacco are shown in FIG. 10. As shown in FIG. 10A, a PCR product of the hygromycin resistance gene was generated from all transformed tobacco, including the plants transformed with pCAMBIA 1300. In contrast, PCR product of 168phyA was only generated from plants transformed with pCX-168PhyA but not from that transformed with pCAMBIA 1300. The results indicated that the vectors pCX-168PhyA and pCAMBIA 1300 were successfully incorporated into the genome of the corresponding tobacco plants by the method described above.

6.5.6 Northern Blotting

Figure 11:
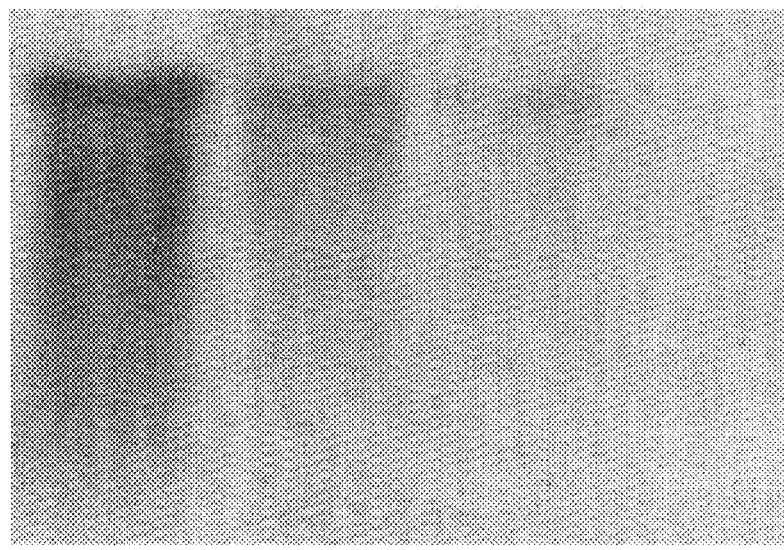
FIG. 11 shows the northern analysis of F0 transgenic tobacco. Twenty (20) μg of total RNA extracted from the plants were loaded onto a 1% (w/v) agarose gel. The 168 phyA cDNA labeled by a DIG-PCR kit was used as a probe. (Roche Diagnostics, Hong Kong). mRNA signals were detected in the transgenic lines (0042, 0043 and 0134) but not in the control lines.
Figure 16:
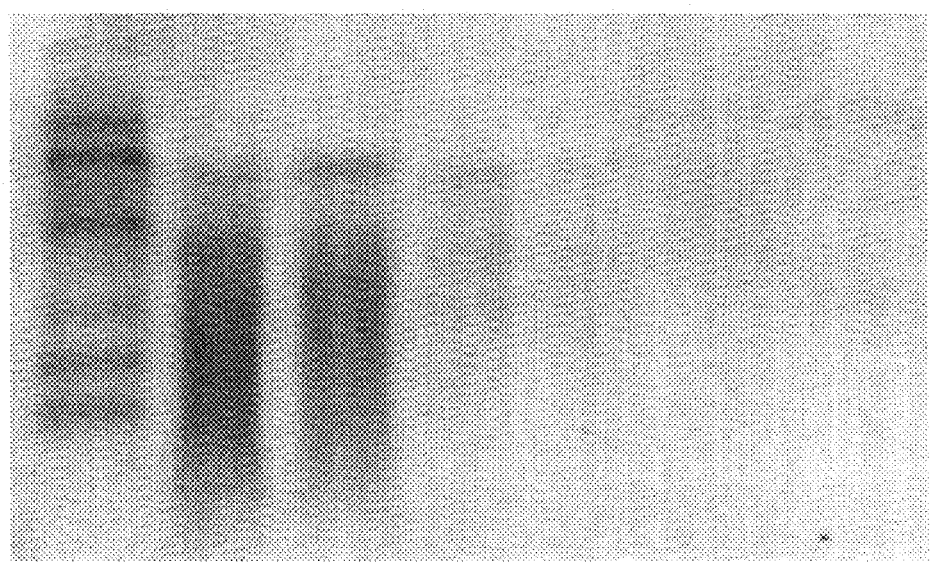
FIG. 16 shows the northern analysis of F1 transgenic tobacco. Twenty (20) μg of total RNA extracted from the plants were loaded onto a 1% (w/v) agarose gel. The 168phyA cDNA labeled by a DIG-PCR kit was used as a probe. (Roche Diagnostics, Hong Kong). mRNA signals were detected in the transgenic lines (0042 and 0134) but not in the control lines.

Total RNA extracted from plant leaves was used as the template for northern blotting detection. RNA of different individual transgenic plants was loaded onto a 1% agarose gel and well separated before transferring overnight onto a nylon membrane by capillary action. The DIG-labeled cDNA of the 168phyA gene excluding the bacterial signal peptide was used as a probe for northern hybridization. All reagents involved were purchased from Roche Diagnostics (Hong Kong) and all procedures were followed according to the manufacturer's manuals. The northern blotting results for the F0 and F1 transgenic tobacco lines are shown in FIGS. 11 and 16, respectively. The phytase enzyme was detected in the protein extract from the F0 lines 0042, 0043 and 0134. As shown in FIG. 16, the mRNA expression was inherited into the F1 lines of 0042 and 0134.

6.5.7 Western Blotting

Total protein extracted from tobacco leaves was used in western blotting experiments. Individual protein samples were well separated by SDS-PAGE on a 10% acrylamide gel and transferred onto a nitrocellulose membrane at 100V, 4° C. for 1 hour. The polyclonal anti-168phyA-antibody was raised in rabbits by immunization with purified 168phyA-encoding phytase that is over-expressed in *Bacillus subtilis*. The polyclonal antibodies were adsorbed with the wild-type tobacco prior to being added as a probe to the sample proteins. NBT/BCIP substrate was applied for signal detection, with procedures undertaken according to manufacturer's protocol.

Figure 12:
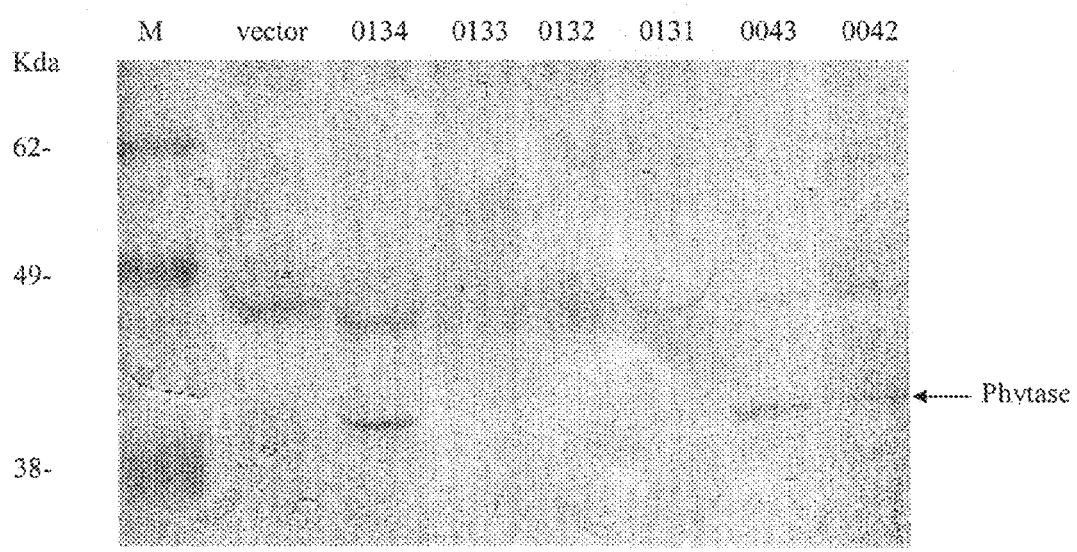
FIG. 12 shows the western analysis of transgenic Tobacco. Thirty (30) μl of soluble protein isolated from tobacco leaves were loaded into each well. Phytase was detected in the transgenic tobacco samples 0042, 0043 and 0134 but not in the control plant.
Figure 13A:
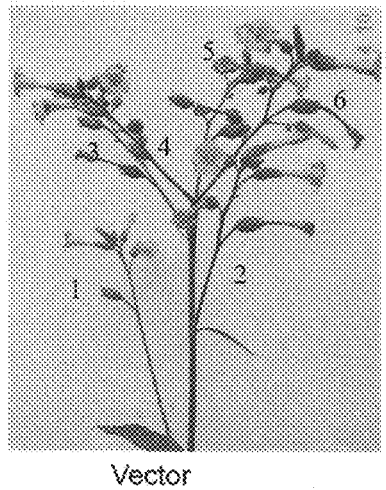
FIGS. 13a-13d show the number of flowering stems in the transgenic tobacco plant (FIGS. 13b-13d) and the control plant (transgenic with the vector only.
Figure 13B:
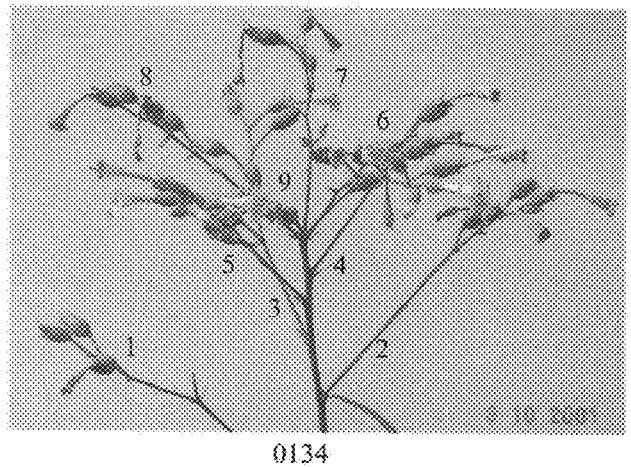
Figure 13C:
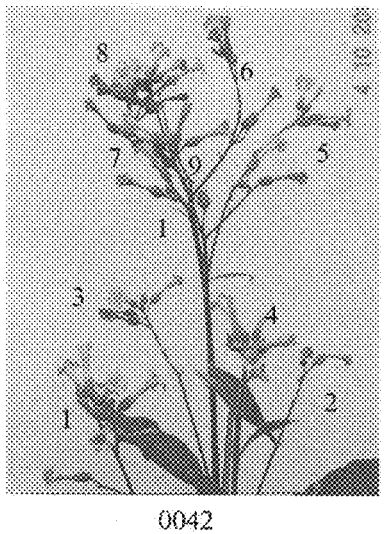
Figure 13D:
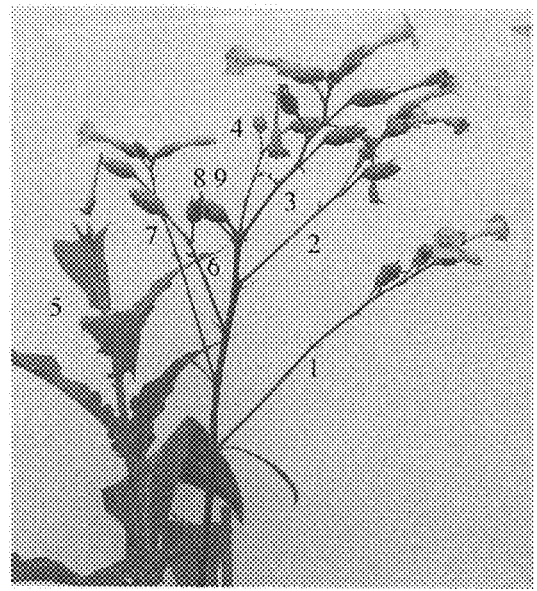
Figure 14A:
FIGS. 14a-14d show the number of major stems in the transgenic tobacco plant (FIGS. 14a-14c) and the control plant (FIG. 14d).
Figure 14B:
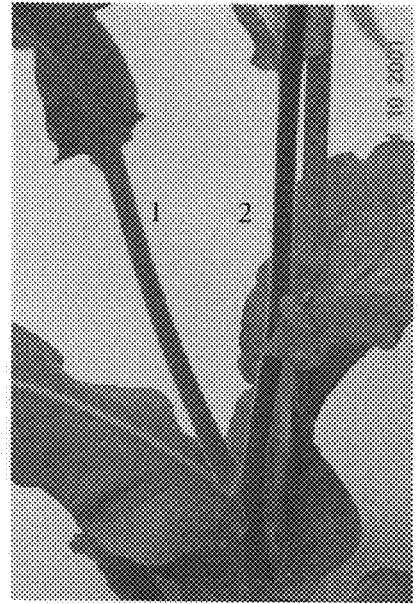
Figure 14C:
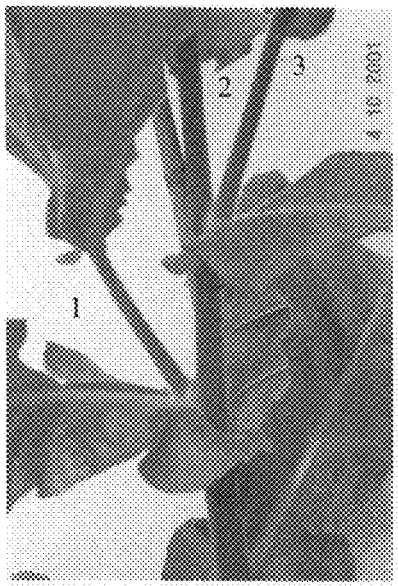
Figure 14D:
Figure 17:
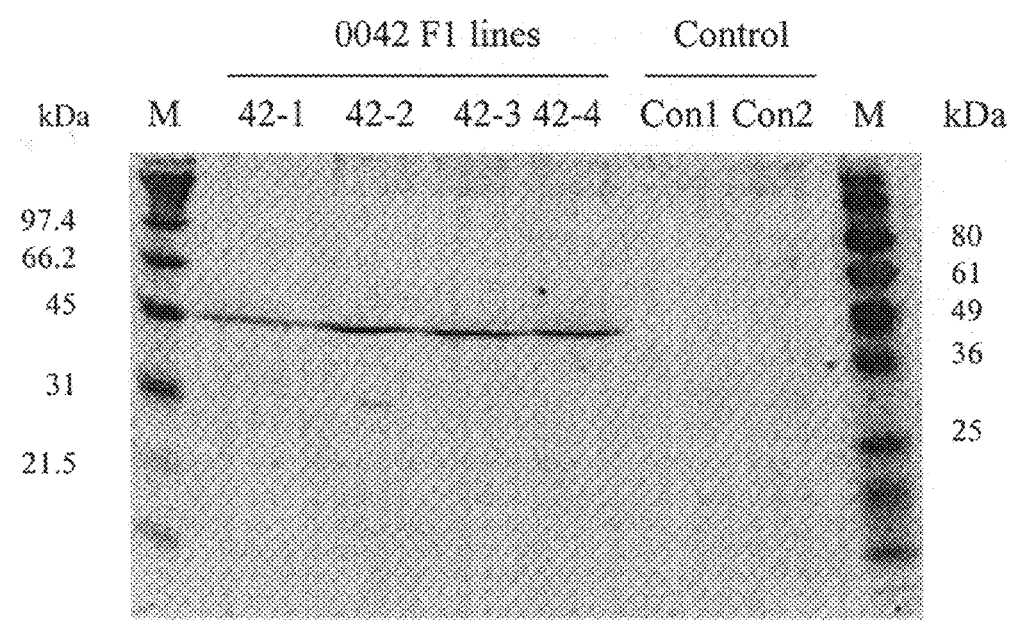
FIG. 17 shows the western analysis of F1 transgenic tobacco. Ten (10) μg of soluble proteins isolated from tobacco leaves were loaded into each well. Phytase was detected in the F1 samples of the transgenic line 0042, but not in the F1 samples of the control line.

The western blotting results for the F0 and F1 transgenic tobacco are shown in FIGS. 12 and 17, respective. The phytase enzyme was detected in the protein extract from the F0 lines 0042, 0043 and 0134. As shown in FIG. 17, the phytase expression was inherited into the F1 lines of 0042. In general, transgenic proteins are not detectable in transgenic plant extract due to their low expression level. For example, recombinant fungal phytase (phyA) expressed in tobacco leaves only gave signal in western blotting after chromatographic purification (Ullah et al., 1999, supra). Hence, the visualization of phytase in western blotting as shown FIGS. 12 and 17 indicated that the expression levels of phytase in the transgenic plants were quite high.

6.5.8 Southern Blotting

The genomic DNA extracted from plant leaves was used for southern analysis. The genomic DNA was cut with HindIII restriction endonuclease in the presence of RNase activity. Digested DNA of different individual transgenic plants was loaded onto a 0.7% agarose gel and well separated before transferring overnight onto a nylon membrane by capillary action. The radiolabeled cDNA of the 168phyA gene excluding the bacterial signal peptide was used as a probe for southern hybridization. All reagents involved were purchased from Roche Diagnostics (Hong Kong) and all procedures were followed according to the manufacturer's manuals.

Figure 15:
FIG. 15 shows the southern blot analysis of F1 transgenic tobacco. Ten (10) μg of HindIII restricted genomic DNA from various F1 lines were loaded into each lane. The 168phyA cDNA radiolabeled by a PCR kit was used as a probe. Specific bands were detected in the transgenic lines (0042 and 0134) but not in the control lines. The F1 lines from 0042 (42-1 and 42-2) were shown to contain a single copy gene whereas the F1 line from 0134 (134-1) was shown to have two gene copies.

As shown in FIG. 15, specific bands were detected in the F1 lines (0042 and 0134) but not in the control lines. The F1 lines from 0042 (42-1 and 42-2) were shown to contain a single copy gene whereas the F1 line from 0134 (134-1) was shown to have two gene copies.

6.5.9 Phenotypes of Control Tobacco and Transgenic Tobacco

Tobacco is a model system in plant transformation because of its high transformation rate and ease of propagation in tissue culture. Tobacco is a dicot plant recognized by its broad leaves, which have high commercial value. Tobacco is an annual plant that can complete the life cycle in 120 days. From seedling to the first flower, it will take about 96-100 days when the growing temperature is above 22° C. and light period longer than 14 hours. Twenty to thirty fruits can be obtained in one tobacco plant; each fruit weighs about 0.3-0.4 g in which more than a thousand seeds are formed. In general, a tobacco plant will bear viable seeds 30 days after the blooming of the first flower.

After transformation, the phenotypes of the transformed plants were followed up and are shown in Table 2. In general, plants transformed with the phytase gene have the first flower blooming when the plants are 101-130 cm high, which is shorter than the height at the time of blooming the first flower of the plants transformed with the vector (135-158 cm). And after flowering, the height of the plants transformed with the phytase gene were still shorter (142-168 cm) than that of the plants transformed with the vector (182-206 cm). Even though the plants transformed with the phytase gene are generally shorter, they usually have more flowering stems (8-10 stems per plant) than the plants transformed with the vector (6 stems) (see Table 2 and FIG. 13). Morphologically, tobacco plants usually have only one major stem. However, four of the phytase-transformed plants developed more than one lateral stems (FIG. 14). Regarding the number of flower buds, tobacco plants transformed with the phytase gene showed increased number of flower buds compared to the tobacco plants transformed with the vector only (see Table 2). Regarding the flowering period, tobacco plant transformed with the phytase gene showed longer flowering period (50 to more than 88 days) than that of the control plants (35-37 days) (see Table 2).

Figure 18:
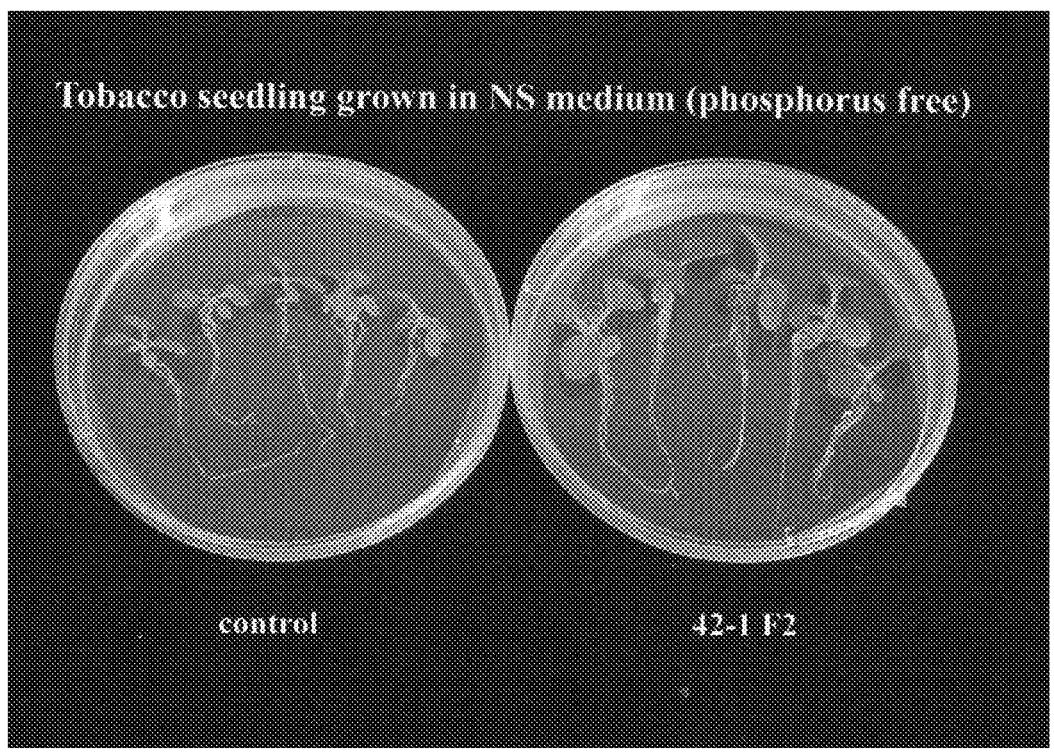
FIG. 18 shows growth of F2 transgenic tobacco seedlings under phosphate deficiency condition. F2 tobacco seeds were grown in a MS medium (which included 1.25 mM phosphate and 30 g/L sucrose) for 15 days before the seedlings were transferred to a modified MS medium (which was phosphate free and the sucrose concentration was reduced to 5 g/L) and grown for another 17 days. More biomass was observed in the transgenic line compared with the control line.

6.5.10 Growth of Transgenic Tobacco Seedlings Under Phosphate Deficiency Condition Control and transgenic (line 42-1) F2 tobacco seeds were sterilized with 33% (v/v) Clorox for 15 min, then rinsed with sterile water 5 times before germination in the MS medium (which included 1.25 mM phosphate and 30 g/L sucrose). After 15 days, seedlings were transferred to a modified MS medium (which was phosphate free and the sucrose concentration was reduced to 5 g/L) and grown for another 17 days. More biomass was observed in the transgenic seedlings compared with the control seedlings in this phosphate starvation experiment (FIG. 18).

6.5.11 Growth of Transgenic Tobacco Seedlings Under Low Phosphate Condition

Figure 19:
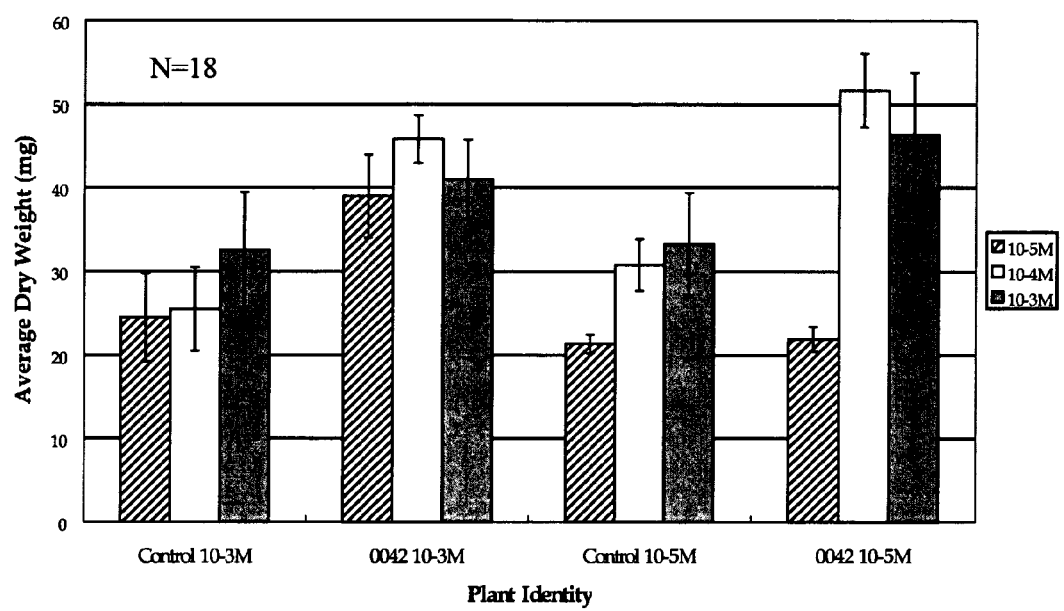
FIG. 19 shows the growth of transgenic tobacco seedlings in agar under low phosphate conditions. The seedlings were first grown on MS agar medium with $10^{-4}$ M or $10^{-5}$ M phosphate for 20 days and then grown on MS agar medium with $10^{-3}$ M, $10^{-4}$ M or $10^{-5}$ M phosphate for another 30 days. The plants were then dried and weighed individually. Each bar is an average of 18 individual plants (N=18).
Figure 20:
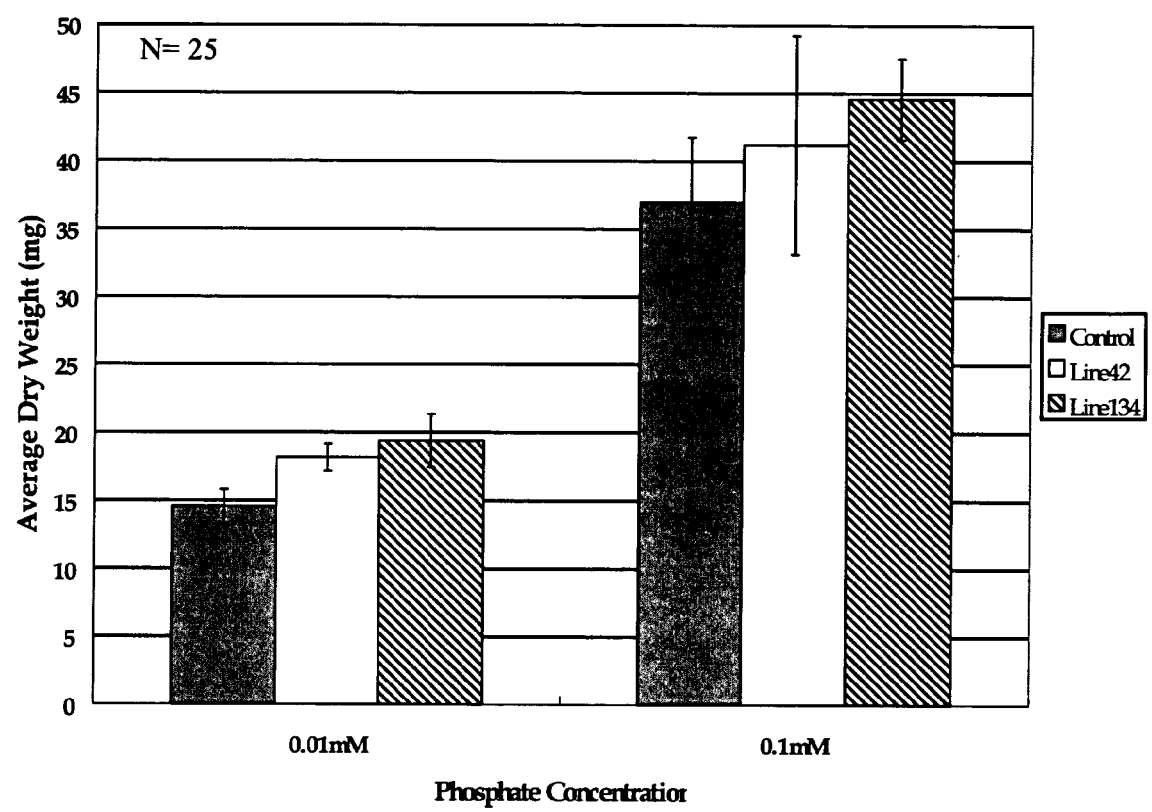
FIG. 20 shows the growth of transgenic tobacco seedlings in liquid medium under low phosphate conditions. The seedlings were first grown on MS0 medium with 1.25 mM phosphate for 10 days and then grown in MS liquid medium with 0.01 or 0.1 mM phosphate for another 20 days. The plants were then dried and weighed individually. Each bar is an average of 25 individual plants (N=25). The transgenic lines (0042 and 0134) attained higher dry weights than the control line under low phosphate conditions."

Surface sterilized control and transgenic tobacco seeds were sowed in petri dishes (60 seeds/9-cm dish) containing 20 ml modified MS agar medium (standard MS medium, except that 10 g sucrose/L, $10^{-3}$M or $10^{-5}$ M phosphate salts were added). After 20 days, 9 seedlings from high phosphate ($10^{-3}$ M) or low phosphate ($10^{-5}$ M) plates were transferred to each of the tissue culture boxes (7 cm×7 cm, 50 ml modified MS agar) containing various phosphate concentrations ($10^{-3}$M, $10^{-4}$ M or $10^{-5}$M). The seedlings were then grown for another 30 days before harvesting for dry weight determination. Each plant was weighed individually. Eighteen (18) plants were weighed in each group and their average weight is shown in FIG. 19. It is statistically significant that the transgenic line 0042 grew bigger than the control line, especially when the availability of phosphate is limited. In addition, an experiment on the growth of seedlings in liquid medium was also carried out. Briefly, tobacco seeds were germinated in MS0 medium (30 g sucrose, 1.25 mM phosphorus) for 10 days, then transferred to liquid MS medium (10 g sucrose, 0.01 or 0.1 mM phosphorus) for 20 days. Twenty-five (25) plants from each line were divided into 5 groups and the dry weight of each group was determined. As shown in FIG. 20, the transgenic lines (0042 and 0134) attained higher dry weights than the control line under low phosphate conditions.

6.5.12 In Vitro Phytase Activity Analysis by HPLC

Five (5) g of young leaf tissue was ground in 10 ml pre-chilled extraction buffer (0.1 M Tris-HCl, pH 7.0, 1 mM phenylmethylsulfonyl fluoride and 0.1 mM CaCl2). Soluble proteins in the aqueous phase were collected by centrifugation at 12000 g for 20 minutes and the protein concentration was quantified by the Bradford protein assay (Bio-Rad). To evaluate the phytase activity in the plant extract, 200 μg of plant proteins from the control plants and the transgenic plants were incubated with 400 μg IP6 (Sigma, P8810) at 37° C. After 4, 6 and 8 hours, 1 volume of 0.05 M HCl was added to stop the enzyme action. To compare the phytase activities in the plant extracts, inositol phosphates (IP6, IP5, IP4, IP3) were purified by anion exchange chromatography (Sandberg and Ahderinne, 1986, HPLC method for determination of inositol Tri-, Tetra, Penta- and Hexaphosphates in foods and intestine contents, *Journal of Food Science* 51(3):547-550). Briefly, 0.5 ml enzyme mix was loaded onto a 2 ml AG-1X8 anion exchange column (Bio-Rad) and the impurities were washed away by 10 column volume of 0.025 M HCl. Subsequently, inositol phosphates were eluted together by 3 M HCl. The eluted samples were then freeze-dried and resuspended in 100 μl mobile phase [50% (v/v) methanol, 0.1% (v/v) formic acid, 1.5% (v/v) tetrabutylammonium hydroxide, and 0.05 M EDTA] before HPLC (Waters 600) analysis (Sandberg and Ahderinne, 1986, supra).

Figure 21:
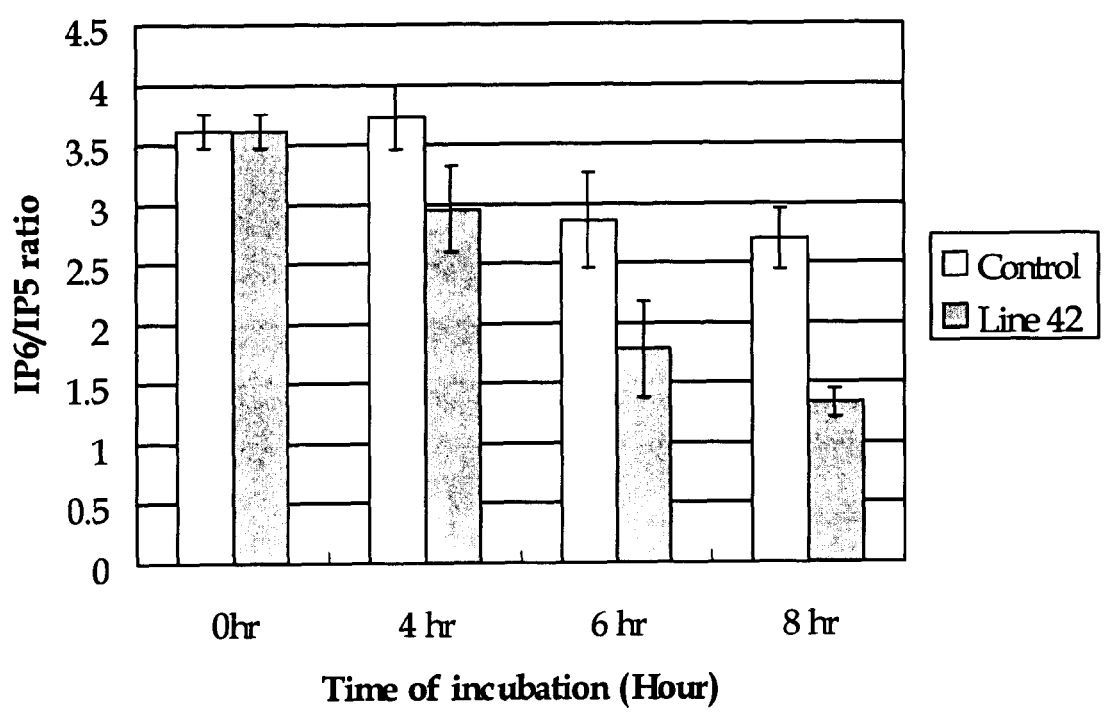
FIG. 21 shows the increased endogenous phytase activity in the transgenic plant. Extracted leaf proteins (200 μg) were incubated with exogenous IP6 (400 μg) at 37° C. for 4, 6 and 8 hours. Inositol phosphates (IP6, IP5, IP4, IP3) were then purified by anion exchange chromatography and analysed by HPLC and the respective peaks of IP6 and IP5 were measured by a refractive index detector. As shown in the figure, the plant extracts from line 42 (N=4) yielded a lower IP6/IP5 ratio when compared with that from the control plant (N=4), indicating that the transgenic plants had higher endogenous phytase activity than the control plants.

Twenty (20) μl was injected into a $C_{18}$ column (Alltech Alltima C18) for inositol phosphate determination. The respective peaks of IP6 and IP5 were measured by a refractive index detector (Shimadzu R1D-10A, Shimadzu Corporation, Japan) and the ratio IP6/IP5 was calculated. Immediately mixed with the plant extract, the IP6/IP5 ratio of the phytic acid substrate was 3.61±0.14 (n=4). During the incubation, IP6 was gradually broken down into lower inositol phosphates (IP5, 4 and 3) and therefore the IP6/IP5 ratio decreased with time. As shown in FIG. 21, the plant extracts from line 42 (N=4) yielded a lower IP6/IP5 ratio when compared with that from the control plant (N=4).

In summary, tobacco plants transformed with the phytase gene have the following phenotypes: (1) Increased number of flowering stems; (2) Increased number of major stems; (3) Increased number of buds; and (4) Extended flowering period (see Table 2). It is expected that the phytase gene-transformed tobacco plants will bear more number of fruit than the control plants since the number of flower buds were increased in the former.

TABLE 2

Phenotypes of transformed tobacco plants

| Plant line | Time of transferring to soil | Time of blooming of the first flower | Plant height at blooming of the first flower (cm) | Plant height after flowering (cm) | No. of main flower stems | No. of major stems* | No. of flower buds* | No. of flowering days |
|---|---|---|---|---|---|---|---|---|
| 0042 | June 8 | August 25 | 102 | 142 | 10 | 3 | 74 | >88[+] |
| 0043 | June 8 | September 8 | 101 | 142 | 9# | 3 | 31# | 58 |
| 0131 | June 8 | September 8 | 125 | 160 | 8 | 1 | 33 | 3 |
| 0133 | June 8 | September 10 | 130 | 168 | 8# | 3 | 47# | 44 |
| 0134 | June 8 | September 4 | 120 | 150 | 9# | 2 | 36# | 50^ |
| Vector control 1 | June 8 | September 4 | 135 | 182 | 6 | 1 | 30 | 36 |
| Vector control 2 | June 15 | September 16 | 158 | 206 | 6 | 1 | 37 | 34 |
| non-transgenic control | June 8 | September 22 | 150 | 185 | 6 | 1 | 32 | 35 |

*Data taken on Oct. 4, 2001.
Only the flower buds on the first major stem was counted. The flower buds on the lateral stems were not mature enough for counting.
[+]Up to Nov. 20, 2001.
^New flowers opened on Nov. 18, 2001.

EQUIVALENTS

Those skilled in the art will recognize, or be able to ascertain many equivalents to the specific embodiments of the invention described herein using no more than routine experimentation. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

We claim:

1. A chimeric expression cassette comprising a nucleotide sequence encoding a phytase, wherein said phytase is from a *Bacillus* strain and comprises the amino acid sequence of SEQ ID NO:4, and said nucleotide sequence is operably linked to regulatory nucleotide sequences such that said regulatory nucleotide sequences cause expression of the nucleotide sequence in plant cells, and wherein the regulatory nucleotide sequences are heterologous to the nucleotide sequence.

2. The chimeric expression cassette of claim 1, wherein said nucleotide sequence comprises SEQ ID NO:3.

3. A chimeric expression cassette comprising a nucleotide sequence encoding a phytase, wherein said phytase is from a *Bacillus* strain and comprises the amino acid sequences of SEQ ID NO:4, except that N-terminal amino acid residues 1 to 26 of SEQ ID NO:4 is deleted, and said nucleotide sequence is operably linked to regulatory nucleotide sequences such that said regulatory nucleotide sequences cause expression of the nucleotide sequence in plant cells, and wherein the regulatory nucleotide sequences are heterologous to the nucleotide sequence.

4. The chimeric expression cassette of claim 3, wherein said nucleotide sequence is SEQ ID NO:3, except that the sequence of nucleotides 100 to 177 of SEQ ID NO:3 is deleted.

5. The chimeric expression cassette of claim 3 or 4, wherein said phytase is expressed intracellularly.

6. An expression vector, comprising the expression cassette of any one of claims 1, 2, 3, and 4.

7. A transformed plant cell comprising the expression vector of claim 6, wherein said plant cell expresses said phytase.

8. The transformed plant cell of claim 7, wherein said cell is of a monocotyledonous species.

9. The transformed plant cell of claim 8, wherein said monocotyledonous species is selected from the group consisting of maize, sorghum, wheat, palm and rice.

10. The transformed plant cell of claim 7, wherein said cell is of a dicotyledonous species.

11. The transformed plant cell of claim 10, wherein said dicotyledonous species is selected from the group consisting of soybean, rapeseed, jojoba, Chinese tallow tree, tobacco, safflower, peanut and sunflower.

12. An in vitro culture comprising the transformed plant cell of claim 8.

13. An in vitro culture comprising the transformed plant cell of claim 10.

14. A transformed plant, wherein a cell of said plant comprises the expression cassette of any one of claims 1, 2, 3, and 4 and expresses said phytase.

15. The transformed plant of claim 14, wherein said plant is a rice plant.

16. The transformed plant of claim 14, wherein said plant is a rapeseed plant.

17. The transformed plant of claim 14, wherein said plant is a sunflower plant.

18. The transformed plant of claim 14, wherein said plant is a safflower plant.

19. The transformed plant of claim 14, wherein said plant is a peanut plant.

20. A method of mobilizing inorganic phosphate from plant phytate in a plant cell for improving plant growth, flowering, and/or fruiting, comprising introducing a nucleic acid molecule comprising the chimeric expression cassette of any one of claims 1, 2, 3, and 4 into said plant cell to produce a transformed plant cell, whereby said transformed plant cell expresses said phytase which mobilizes said inorganic phosphate from plant phytate.

21. The method of claim 20, further comprising the step of producing a whole plant from the transformed plant cell, wherein said plant comprises the cell that expresses said phytase.

22. The method of claim 21, further comprising the step of sexually or clonally reproducing said whole plant, wherein a progeny of said whole plant comprises a cell that expresses said phytase.

23. The method of claim 20, wherein said expression cassette is introduced into said plant cell by electroporation.

24. The method of claim 20, wherein said expression cassette is introduced into said plant cell by microparticle bombardment.

25. The method of claim 20, wherein said expression cassette is introduced into said plant cell by microinjection.

26. A method for mobilizing inorganic phosphate from plant phytate for improving plant growth, flowering, and/or fruiting in an *Agrobacterium*-susceptible dicotyledonous plant, comprising infecting a plant cell of said plant with *Agrobacterium* that comprises the expression cassette of any one of claims 1, 2, 3, and 4, whereby said infected plant cell expresses said phytase which mobilizes said inorganic phosphate.

27. A chimeric expression cassette comprising a nucleotide sequence encoding a phytase, wherein said phytase is from a *Bacillus* strain and comprises the amino acid sequence of SEQ ID NO:4, except that N-terminal amino acid residues 1 to 26 of SEQ ID NO:4 are replaced by a plant signal peptide, said nucleotide sequence being operably linked to regulatory nucleotide sequences such that said regulatory nucleotide sequences cause expression of the nucleotide sequence in plant cells and said phytase is secreted from the plant cells, wherein the regulatory nucleotide sequences are heterologous to the nucleotide sequence.

28. The chimeric expression cassette of claim 27, wherein said nucleotide sequence is SEQ ID NO:3, except that the sequence of nucleotides 100 to 177 of SEQ ID NO:3 is replaced by a plant signal sequence such that said phytase is secreted from the plant cells.

* * * * *

SEQUENCE LISTING

<160> NUMBER OF SEQ ID NOS: 32

<210> SEQ ID NO 1
<211> LENGTH: 1390
<212> TYPE: DNA
<213> ORGANISM: Bacillus licheniformis
<220> FEATURE:
<221> NAME/KEY: CDS
<222> LOCATION: (241)..(1386)

<400> SEQUENCE: 1

```
ttttacccga tggatgggga cttaaacgaa cttgcgtttg agatatacat tccgattcat      60
tgagagatag cgatgttaaa ggcagccccc ggaaaaaatt ccgggggttt tctttgggtt     120
tcgtactcta gagtatcggc ggtcttttt agccatcact tttaacaaaa gtttacatac      180
cctcaaatga taattttcat tggtttgcta ggataaatgt tatgaaaagg aggttaatat     240
```

| | | | | | | | | | | | | | | | | |
|---|---|---|---|---|---|---|---|---|---|---|---|---|---|---|---|---|
| atg | aac | ttt | tac | aaa | acg | ctc | gct | tta | tca | aca | ctc | gca | gca | tcc | tta | 288 |
| Met | Asn | Phe | Tyr | Lys | Thr | Leu | Ala | Leu | Ser | Thr | Leu | Ala | Ala | Ser | Leu | |
| 1 | | | | 5 | | | | | 10 | | | | | 15 | | |
| tgg | tct | ccc | tca | tgg | agc | agt | ctc | ccc | cat | aac | gaa | gct | gcg | gct | cac | 336 |
| Trp | Ser | Pro | Ser | Trp | Ser | Ser | Leu | Pro | His | Asn | Glu | Ala | Ala | Ala | His | |
| | | | 20 | | | | | 25 | | | | | 30 | | | |
| aaa | gaa | ttc | acg | gtg | act | gcc | gat | gca | gag | aca | gag | ccg | gtg | gat | acc | 384 |
| Lys | Glu | Phe | Thr | Val | Thr | Ala | Asp | Ala | Glu | Thr | Glu | Pro | Val | Asp | Thr | |
| | | 35 | | | | | 40 | | | | | 45 | | | | |
| cct | gac | gac | gcg | gca | gat | gac | ccg | gcg | att | tgg | gtt | cat | ccg | aag | cag | 432 |
| Pro | Asp | Asp | Ala | Ala | Asp | Asp | Pro | Ala | Ile | Trp | Val | His | Pro | Lys | Gln | |
| 50 | | | | | 55 | | | | | 60 | | | | | | |
| cct | gaa | aaa | agc | agg | ctc | atc | acc | aca | aac | aaa | aag | tcg | ggc | tta | atc | 480 |
| Pro | Glu | Lys | Ser | Arg | Leu | Ile | Thr | Thr | Asn | Lys | Lys | Ser | Gly | Leu | Ile | |
| 65 | | | | | 70 | | | | | 75 | | | | | 80 | |
| gtc | tat | gat | ttg | aag | gga | aaa | cag | ctt | gcg | gcc | tat | ccg | ttt | ggc | aaa | 528 |
| Val | Tyr | Asp | Leu | Lys | Gly | Lys | Gln | Leu | Ala | Ala | Tyr | Pro | Phe | Gly | Lys | |
| | | | | 85 | | | | | 90 | | | | | 95 | | |
| tta | aac | aat | gtc | gac | ctg | cgc | tac | aat | ttt | ccg | ctc | gat | ggc | aaa | aaa | 576 |
| Leu | Asn | Asn | Val | Asp | Leu | Arg | Tyr | Asn | Phe | Pro | Leu | Asp | Gly | Lys | Lys | |
| | | | 100 | | | | | 105 | | | | | 110 | | | |
| att | gat | att | gcc | ggg | gcc | tca | aac | cgg | tca | gac | ggc | aaa | aac | acg | gtt | 624 |
| Ile | Asp | Ile | Ala | Gly | Ala | Ser | Asn | Arg | Ser | Asp | Gly | Lys | Asn | Thr | Val | |
| | | 115 | | | | | 120 | | | | | 125 | | | | |
| gaa | att | tac | gcc | ttt | gac | ggc | gaa | aaa | agc | aag | ctg | aag | aac | atc | gtc | 672 |
| Glu | Ile | Tyr | Ala | Phe | Asp | Gly | Glu | Lys | Ser | Lys | Leu | Lys | Asn | Ile | Val | |
| 130 | | | | | 135 | | | | | 140 | | | | | | |
| aat | cct | caa | aaa | cct | att | caa | acc | gat | atc | cag | gag | gta | tat | ggc | ttc | 720 |
| Asn | Pro | Gln | Lys | Pro | Ile | Gln | Thr | Asp | Ile | Gln | Glu | Val | Tyr | Gly | Phe | |
| 145 | | | | | 150 | | | | | 155 | | | | | 160 | |
| agc | ctg | tat | cac | agc | cag | aaa | acc | ggc | aag | ttc | tac | gcc | atg | gtg | acc | 768 |
| Ser | Leu | Tyr | His | Ser | Gln | Lys | Thr | Gly | Lys | Phe | Tyr | Ala | Met | Val | Thr | |
| | | | | 165 | | | | | 170 | | | | | 175 | | |
| gga | aag | aac | gga | gaa | ttc | gag | caa | tat | gaa | ctg | ttt | gac | aac | gga | aaa | 816 |
| Gly | Lys | Asn | Gly | Glu | Phe | Glu | Gln | Tyr | Glu | Leu | Phe | Asp | Asn | Gly | Lys | |
| | | | 180 | | | | | 185 | | | | | 190 | | | |
| gga | caa | gtc | gag | ggc | aaa | aag | gtc | cgc | tca | ttc | aaa | atg | agc | tct | caa | 864 |
| Gly | Gln | Val | Glu | Gly | Lys | Lys | Val | Arg | Ser | Phe | Lys | Met | Ser | Ser | Gln | |
| | | 195 | | | | | 200 | | | | | 205 | | | | |
| aca | gaa | ggg | ctt | gcg | gca | gat | gat | gaa | tac | ggc | aaa | atg | tac | atc | gcc | 912 |
| Thr | Glu | Gly | Leu | Ala | Ala | Asp | Asp | Glu | Tyr | Gly | Lys | Met | Tyr | Ile | Ala | |
| | | 210 | | | | | 215 | | | | | 220 | | | | |

```
gaa gaa gac gtt gcg att tgg tct ttc agc gcc gag ccg gac ggc gga      960
Glu Glu Asp Val Ala Ile Trp Ser Phe Ser Ala Glu Pro Asp Gly Gly
225                 230                 235                 240 gat aaa gga aaa atc gtc gat cgt gcc gac gga ccg cat cta act tct     1008
Asp Lys Gly Lys Ile Val Asp Arg Ala Asp Gly Pro His Leu Thr Ser
            245                 250                 255 gat att gaa ggg ctg acg att tac tac gga gaa gac gga gaa ggg tat     1056
Asp Ile Glu Gly Leu Thr Ile Tyr Tyr Gly Glu Asp Gly Glu Gly Tyr
        260                 265                 270 ttg atc gcg tcc agt cag ggc gat aac cgc tat gcc atc tat gac cgg     1104
Leu Ile Ala Ser Ser Gln Gly Asp Asn Arg Tyr Ala Ile Tyr Asp Arg
    275                 280                 285 cgc ggg aaa aac gac tac gtc act gct ttt tca att gag gac ggc aaa     1152
Arg Gly Lys Asn Asp Tyr Val Thr Ala Phe Ser Ile Glu Asp Gly Lys
290                 295                 300 gaa atc gac ggg aca agc gat acc gat gga atc gac gtc atc ggc ttc     1200
Glu Ile Asp Gly Thr Ser Asp Thr Asp Gly Ile Asp Val Ile Gly Phe
305                 310                 315                 320 ggc ctc ggc aaa aca tat cca tac ggc atc ttt gtc gcc caa gac ggc     1248
Gly Leu Gly Lys Thr Tyr Pro Tyr Gly Ile Phe Val Ala Gln Asp Gly
            325                 330                 335 gaa aat acg gaa aat gga caa ccg gcc aat cag aac ttc aaa att gtc     1296
Glu Asn Thr Glu Asn Gly Gln Pro Ala Asn Gln Asn Phe Lys Ile Val
        340                 345                 350 tcc tgg gaa aaa atc gcc gac gcg ctg gac gac aaa cct gat atc gat     1344
Ser Trp Glu Lys Ile Ala Asp Ala Leu Asp Asp Lys Pro Asp Ile Asp
    355                 360                 365 gat cag gtc gat ccc cga aaa ctg aaa aac cga gcc aaa taa ggac        1390
Asp Gln Val Asp Pro Arg Lys Leu Lys Asn Arg Ala Lys
370                 375                 380

<210> SEQ ID NO 2
<211> LENGTH: 381
<212> TYPE: PRT
<213> ORGANISM: Bacillus licheniformis

<400> SEQUENCE: 2

Met Asn Phe Tyr Lys Thr Leu Ala Leu Ser Thr Leu Ala Ala Ser Leu
 1               5                  10                  15

Trp Ser Pro Ser Trp Ser Leu Pro His Asn Glu Ala Ala His
            20                  25                  30

Lys Glu Phe Thr Val Thr Ala Asp Ala Glu Thr Glu Pro Val Asp Thr
        35                  40                  45

Pro Asp Asp Ala Ala Asp Pro Ala Ile Trp Val His Pro Lys Gln
    50                  55                  60

Pro Glu Lys Ser Arg Leu Ile Thr Thr Asn Lys Lys Ser Gly Leu Ile
65                  70                  75                  80

Val Tyr Asp Leu Lys Gly Lys Gln Leu Ala Ala Tyr Pro Phe Gly Lys
                85                  90                  95

Leu Asn Asn Val Asp Leu Arg Tyr Asn Phe Pro Leu Asp Gly Lys Lys
            100                 105                 110

Ile Asp Ile Ala Gly Ala Ser Asn Arg Ser Asp Gly Lys Asn Thr Val
        115                 120                 125

Glu Ile Tyr Ala Phe Asp Gly Glu Lys Ser Lys Leu Lys Asn Ile Val
    130                 135                 140

Asn Pro Gln Lys Pro Ile Gln Thr Asp Ile Gln Glu Val Tyr Gly Phe
145                 150                 155                 160

Ser Leu Tyr His Ser Gln Lys Thr Gly Lys Phe Tyr Ala Met Val Thr
```

-continued

```
                       165                 170                 175
Gly Lys Asn Gly Glu Phe Glu Gln Tyr Glu Leu Phe Asp Asn Gly Lys
                   180                 185                 190

Gly Gln Val Glu Gly Lys Lys Val Arg Ser Phe Lys Met Ser Ser Gln
               195                 200                 205

Thr Glu Gly Leu Ala Ala Asp Asp Glu Tyr Gly Lys Met Tyr Ile Ala
           210                 215                 220

Glu Glu Asp Val Ala Ile Trp Ser Phe Ser Ala Glu Pro Asp Gly Gly
225                 230                 235                 240

Asp Lys Gly Lys Ile Val Asp Arg Ala Asp Gly Pro His Leu Thr Ser
                245                 250                 255

Asp Ile Glu Gly Leu Thr Ile Tyr Tyr Gly Glu Asp Gly Glu Gly Tyr
            260                 265                 270

Leu Ile Ala Ser Ser Gln Gly Asp Asn Arg Tyr Ala Ile Tyr Asp Arg
        275                 280                 285

Arg Gly Lys Asn Asp Tyr Val Thr Ala Phe Ser Ile Glu Asp Gly Lys
    290                 295                 300

Glu Ile Asp Gly Thr Ser Asp Thr Asp Gly Ile Asp Val Ile Gly Phe
305                 310                 315                 320

Gly Leu Gly Lys Thr Tyr Pro Tyr Gly Ile Phe Val Ala Gln Asp Gly
                325                 330                 335

Glu Asn Thr Glu Asn Gly Gln Pro Ala Asn Gln Asn Phe Lys Ile Val
            340                 345                 350

Ser Trp Glu Lys Ile Ala Asp Ala Leu Asp Asp Lys Pro Asp Ile Asp
        355                 360                 365

Asp Gln Val Asp Pro Arg Lys Leu Lys Asn Arg Ala Lys
    370                 375                 380

<210> SEQ ID NO 3
<211> LENGTH: 1380
<212> TYPE: DNA
<213> ORGANISM: Bacillus subtilis
<220> FEATURE:
<221> NAME/KEY: CDS
<222> LOCATION: (100)..(1248)

<400> SEQUENCE: 3
gagtcagaaa ccctataaaa aaaggttcat tttcctcacg gtaatcacct gtatatattt      60
tacaatagta gtgttagtga taaaagagga gggtaccaa atg aag gtt cca aaa      114
                                            Met Lys Val Pro Lys
                                              1               5 aca atg ctg cta agc act gcc gcg ggt tta ttg ctt agc ctg aca gca      162
Thr Met Leu Leu Ser Thr Ala Ala Gly Leu Leu Leu Ser Leu Thr Ala
              10                  15                  20 acc tcg gtg tcg gct cat tat gtg aat gag gaa cat cat ttc aaa gtg      210
Thr Ser Val Ser Ala His Tyr Val Asn Glu Glu His His Phe Lys Val
          25                  30                  35 act gca cac acg gag aca gat ccg gtc gca tct ggc gat gat gca gca      258
Thr Ala His Thr Glu Thr Asp Pro Val Ala Ser Gly Asp Asp Ala Ala
     40                  45                  50 gat gac ccg gcc att tgg gtt cat gaa aaa cac ccg gaa aaa agc aag      306
Asp Asp Pro Ala Ile Trp Val His Glu Lys His Pro Glu Lys Ser Lys
 55                  60                  65 ttg att aca aca aat aag aag tca ggg ctc gtt gtg tat gat tta gac      354
Leu Ile Thr Thr Asn Lys Lys Ser Gly Leu Val Val Tyr Asp Leu Asp
 70                  75                  80                  85 gga aaa cag ctt cat tct tat gag ttt ggc aag ctc aat aat gtc gat      402
```

```
Gly Lys Gln Leu His Ser Tyr Glu Phe Gly Lys Leu Asn Asn Val Asp
                 90                  95                 100 ctg cgc tat gat ttt cca ttg aac ggc gaa aaa att gat att gct gcc        450
Leu Arg Tyr Asp Phe Pro Leu Asn Gly Glu Lys Ile Asp Ile Ala Ala
                105                 110                 115 gca tcc aac cgg tcc gaa gga aaa aat aca att gaa gta tat gca ata        498
Ala Ser Asn Arg Ser Glu Gly Lys Asn Thr Ile Glu Val Tyr Ala Ile
            120                 125                 130 gac ggg gat aaa gga aaa ttg aaa agc att aca gat ccg aac cat cct        546
Asp Gly Asp Lys Gly Lys Leu Lys Ser Ile Thr Asp Pro Asn His Pro
        135                 140                 145 att tcc acc aat att tct gag gtt tat gga ttc agc ttg tat cac agc        594
Ile Ser Thr Asn Ile Ser Glu Val Tyr Gly Phe Ser Leu Tyr His Ser
150                 155                 160                 165 cag aaa aca gga gca ttt tac gca tta gtg aca ggc aaa caa ggg gaa        642
Gln Lys Thr Gly Ala Phe Tyr Ala Leu Val Thr Gly Lys Gln Gly Glu
                170                 175                 180 ttt gag cag tat gaa att gtt gat ggt gga aag ggt tat gta aca ggg        690
Phe Glu Gln Tyr Glu Ile Val Asp Gly Gly Lys Gly Tyr Val Thr Gly
                185                 190                 195 aaa aag gtg cgt gaa ttt aag ttg aat tct cag acc gaa ggc ctt gtt        738
Lys Lys Val Arg Glu Phe Lys Leu Asn Ser Gln Thr Glu Gly Leu Val
            200                 205                 210 gcg gat gat gag tac gga aac cta tac ata gca gag gaa gat gag gcc        786
Ala Asp Asp Glu Tyr Gly Asn Leu Tyr Ile Ala Glu Glu Asp Glu Ala
        215                 220                 225 atc tgg aaa ttt aac gct gag ccc ggc gga ggg tca aag ggg cag gtt        834
Ile Trp Lys Phe Asn Ala Glu Pro Gly Gly Gly Ser Lys Gly Gln Val
230                 235                 240                 245 gtt gac cgt gcg aca gga gat cat ttg aca gct gat att gaa gga ctg        882
Val Asp Arg Ala Thr Gly Asp His Leu Thr Ala Asp Ile Glu Gly Leu
                250                 255                 260 aca atc tat tat gca cca aat ggc aaa gga tat ctc atg gct tca agt        930
Thr Ile Tyr Tyr Ala Pro Asn Gly Lys Gly Tyr Leu Met Ala Ser Ser
                265                 270                 275 caa gga aat aac agc tat gca atg tat gaa cgg cag ggg aaa aat cgc        978
Gln Gly Asn Asn Ser Tyr Ala Met Tyr Glu Arg Gln Gly Lys Asn Arg
            280                 285                 290 tat gta gcc aac ttt gag att aca gat ggc gag aag ata gac ggt act       1026
Tyr Val Ala Asn Phe Glu Ile Thr Asp Gly Glu Lys Ile Asp Gly Thr
        295                 300                 305 agt gac acg gat ggt att gat gtt ctc ggt ttc gga ctt ggc cca aaa       1074
Ser Asp Thr Asp Gly Ile Asp Val Leu Gly Phe Gly Leu Gly Pro Lys
310                 315                 320                 325 tat ccg tac ggg att ttt gtg gcg cag gac ggc gaa aat att gat aac       1122
Tyr Pro Tyr Gly Ile Phe Val Ala Gln Asp Gly Glu Asn Ile Asp Asn
                330                 335                 340 gga caa gcc gtc aat caa aat ttc aaa att gta tcg tgg gaa caa att       1170
Gly Gln Ala Val Asn Gln Asn Phe Lys Ile Val Ser Trp Glu Gln Ile
                345                 350                 355 gca cag cat ctc ggc gaa atg cct gat ctt cat aaa cag gta aat ccg       1218
Ala Gln His Leu Gly Glu Met Pro Asp Leu His Lys Gln Val Asn Pro
            360                 365                 370 agg aag ctg aaa gac cgt tct gac ggc tag aatagaaagc agcttgtgca         1268
Arg Lys Leu Lys Asp Arg Ser Asp Gly
        375                 380 gctgcttttt tctatgaata aaaaaatcgt tcatagcaat gaacgatttt tcaagaaagc     1328
gccagatgaa tcgcttttag ttttgcagga agctcatcaa acgtaaatgc gg             1380
```

```
<210> SEQ ID NO 4
<211> LENGTH: 382
<212> TYPE: PRT
<213> ORGANISM: Bacillus subtilis

<400> SEQUENCE: 4

Met Lys Val Pro Lys Thr Met Leu Leu Ser Thr Ala Ala Gly Leu Leu
  1               5                  10                  15

Leu Ser Leu Thr Ala Thr Ser Val Ser Ala His Tyr Val Asn Glu Glu
             20                  25                  30

His His Phe Lys Val Thr Ala His Thr Glu Thr Asp Pro Val Ala Ser
         35                  40                  45

Gly Asp Ala Ala Asp Asp Pro Ala Ile Trp Val His Glu Lys His
     50                  55                  60

Pro Glu Lys Ser Lys Leu Ile Thr Thr Asn Lys Lys Ser Gly Leu Val
 65                  70                  75                  80

Val Tyr Asp Leu Asp Gly Lys Gln Leu His Ser Tyr Glu Phe Gly Lys
                 85                  90                  95

Leu Asn Asn Val Asp Leu Arg Tyr Asp Phe Pro Leu Asn Gly Glu Lys
            100                 105                 110

Ile Asp Ile Ala Ala Ala Ser Asn Arg Ser Glu Gly Lys Asn Thr Ile
        115                 120                 125

Glu Val Tyr Ala Ile Asp Gly Asp Lys Gly Lys Leu Lys Ser Ile Thr
    130                 135                 140

Asp Pro Asn His Pro Ile Ser Thr Asn Ile Ser Glu Val Tyr Gly Phe
145                 150                 155                 160

Ser Leu Tyr His Ser Gln Lys Thr Gly Ala Phe Tyr Ala Leu Val Thr
                165                 170                 175

Gly Lys Gln Gly Glu Phe Glu Gln Tyr Glu Ile Val Asp Gly Gly Lys
            180                 185                 190

Gly Tyr Val Thr Gly Lys Lys Val Arg Glu Phe Lys Leu Asn Ser Gln
        195                 200                 205

Thr Glu Gly Leu Val Ala Asp Asp Glu Tyr Gly Asn Leu Tyr Ile Ala
    210                 215                 220

Glu Glu Asp Glu Ala Ile Trp Lys Phe Asn Ala Glu Pro Gly Gly Gly
225                 230                 235                 240

Ser Lys Gly Gln Val Val Asp Arg Ala Thr Gly Asp His Leu Thr Ala
                245                 250                 255

Asp Ile Glu Gly Leu Thr Ile Tyr Tyr Ala Pro Asn Gly Lys Gly Tyr
            260                 265                 270

Leu Met Ala Ser Ser Gln Gly Asn Asn Ser Tyr Ala Met Tyr Glu Arg
        275                 280                 285

Gln Gly Lys Asn Arg Tyr Val Ala Asn Phe Glu Ile Thr Asp Gly Glu
    290                 295                 300

Lys Ile Asp Gly Thr Ser Asp Thr Asp Gly Ile Asp Val Leu Gly Phe
305                 310                 315                 320

Gly Leu Gly Pro Lys Tyr Pro Tyr Gly Ile Phe Val Ala Gln Asp Gly
                325                 330                 335

Glu Asn Ile Asp Asn Gly Gln Ala Val Asn Gln Asn Phe Lys Ile Val
            340                 345                 350

Ser Trp Glu Gln Ile Ala Gln His Leu Gly Glu Met Pro Asp Leu His
        355                 360                 365

Lys Gln Val Asn Pro Arg Lys Leu Lys Asp Arg Ser Asp Gly
    370                 375                 380
```

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)
<223> OTHER INFORMATION: deoxyinosine
<220> FEATURE:
<221> NAME/KEY: modified_base
<222> LOCATION: (9)
<223> OTHER INFORMATION: deoxyinosine
<220> FEATURE:
<221> NAME/KEY: modified_base
<222> LOCATION: (18)
<223> OTHER INFORMATION: deoxyinosine

<400> SEQUENCE: 5
gaygcngcng aygayccngc                                            20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)
<223> OTHER INFORMATION: deoxyinosine

<400> SEQUENCE: 6
tcrtaytgyt craaytcncc                                            20

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atgaattcgt cgggcttaat cgtctatg                                   28

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atggatcctc aggctgcttc ggatgaa                                    27

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
```
atgaattcat ggcttcagcc gtatcac                                        27

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atggatccgt gttttgccg tctgacc                                         27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcgaattcga taccgatgga atcgacg                                        27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atggatcctc atagatggca tagcggt                                        27

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atttaacata tgaacttta caaaacgctc                                      30

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atggatccgt ccttatttgg ctcggt                                         26

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aggaattcca tatgaaggtt ccaaaaacaa tgc                                      33

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
taggatcctc atctggcgct ttcttgt                                             27

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atggatccat ggctcattat gtgaatgagg aacat                                    35

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
attagagctc ctagccgtca gaacggtctt                                          30

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctacaaagat cgttatgttt atcggca                                             27

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agaccaatgc ggagcatata cg                                                  22

<210> SEQ ID NO 21
<211> LENGTH: 1290
<212> TYPE: DNA
<213> ORGANISM: Bacillus subtilis

<400> SEQUENCE: 21
cacatttgac aattttcaca aaaacttaac actgacaatc atgtatatat gttacaattg         60
aagtgcacgt tcataaaagg aggaagtaaa atgaatcatt caaaaacact tttgttaacc        120

-continued

```
gcggcggccg gactgatgct cacatgcggt gcggtgtctt cccaggcaaa gcataagctg     180
tccgatcctt atcattttac cgtgaatgca gcggcggaaa cggaaccggt tgatacggcc     240
ggtgacgcgg ctgatgatcc tgcgatttgg ctggacccca agactcctca gaacagcaaa     300
ttgattacga ccaataaaaa atcaggttta gtcgtttaca gccttgatgg taagatgctt     360
cattcctata ataccgggaa gctgaacaat gtcgatatcc gttatgattt tccgttgaac     420
ggcaaaaaag tcgatatcgc ggcagcatcc aatcggtctg aaggaaaaaa taccattgag     480
atttacgcta ttgatggaaa aaacggcaca ttacaaagca tgacagatcc agaccatccg     540
attgcaacag caattaatga ggtatacggt tttaccttat accacagtca aaaaacagga     600
aaatattacg cgatggtgac aggaaaagag ggtgaatttg aacaatacga attaaaggcg     660
gacaaaaatg gatacatatc cggcaaaaag gtacgggcgt ttaaaatgaa ttcccagacg     720
gaagggatgg cagcagacga tgaatacggc aggctttata tcgcagaaga agatgaggcc     780
atttggaagt tcagcgccga gccggacggc ggcagtaacg gaacggttat cgaccgtgcc     840
gacggcaggc atttaactcg tgatattgaa ggattgacga tttactacgc tgctgacggg     900
aaaggctatc tgatggcatc aagccaggga acagcagct acgccattta tgacagacaa      960
ggaaagaaca aatatgttgc ggattttcgc ataacagacg gtcctgaaac agacgggaca    1020
agcgatacag acggaattga cgttctgggt ttcggactgg ggcctgaata tccgttcggt    1080 attttttgtcg cacaggacgg tgaaaatata gatcacggcc aaaaggccaa tcaaaatttt    1140
aaaatcgtgc catgggaaag aattgctgat caaatcggtt tccgcccgct ggcaaatgaa    1200
caggttgacc cgagaaaact gaccgacaga agcggaaaat aaacatgcaa aaagcagctt    1260
atacaagctg cttttttgcat gtgaagaacg                                    1290
```

<210> SEQ ID NO 22
<211> LENGTH: 383
<212> TYPE: PRT
<213> ORGANISM: Bacillus subtilis

<400> SEQUENCE: 22

```
Met Asn His Ser Lys Thr Leu Leu Thr Ala Ala Gly Leu Met
 1               5                  10                  15

Leu Thr Cys Gly Ala Val Ser Ser Gln Ala Lys His Lys Leu Ser Asp
             20                  25                  30

Pro Tyr His Phe Thr Val Asn Ala Ala Ala Glu Thr Glu Pro Val Asp
         35                  40                  45

Thr Ala Gly Asp Ala Ala Asp Asp Pro Ala Ile Trp Leu Asp Pro Lys
     50                  55                  60

Thr Pro Gln Asn Ser Lys Leu Ile Thr Thr Asn Lys Lys Ser Gly Leu
 65                  70                  75                  80

Val Val Tyr Ser Leu Asp Gly Lys Met Leu His Ser Tyr Asn Thr Gly
                 85                  90                  95

Lys Leu Asn Asn Val Asp Ile Arg Tyr Asp Phe Pro Leu Asn Gly Lys
            100                 105                 110

Lys Val Asp Ile Ala Ala Ala Ser Asn Arg Ser Glu Gly Lys Asn Thr
        115                 120                 125

Ile Glu Ile Tyr Ala Ile Asp Gly Lys Asn Gly Thr Leu Gln Ser Met
    130                 135                 140

Thr Asp Pro Asp His Pro Ile Ala Thr Ala Ile Asn Glu Val Tyr Gly
145                 150                 155                 160

Phe Thr Leu Tyr His Ser Gln Lys Thr Gly Lys Tyr Tyr Ala Met Val
```

```
                   165                 170                 175
Thr Gly Lys Glu Gly Glu Phe Glu Gln Tyr Glu Leu Lys Ala Asp Lys
                180                 185                 190

Asn Gly Tyr Ile Ser Gly Lys Lys Val Arg Ala Phe Lys Met Asn Ser
            195                 200                 205

Gln Thr Glu Gly Met Ala Ala Asp Asp Glu Tyr Gly Arg Leu Tyr Ile
        210                 215                 220

Ala Glu Glu Asp Glu Ala Ile Trp Lys Phe Ser Ala Glu Pro Asp Gly
225                 230                 235                 240

Gly Ser Asn Gly Thr Val Ile Asp Arg Ala Asp Gly Arg His Leu Thr
                245                 250                 255

Arg Asp Ile Glu Gly Leu Thr Ile Tyr Tyr Ala Ala Asp Gly Lys Gly
            260                 265                 270

Tyr Leu Met Ala Ser Ser Gln Gly Asn Ser Ser Tyr Ala Ile Tyr Asp
        275                 280                 285

Arg Gln Gly Lys Asn Lys Tyr Val Ala Asp Phe Arg Ile Thr Asp Gly
    290                 295                 300

Pro Glu Thr Asp Gly Thr Ser Asp Thr Asp Gly Ile Asp Val Leu Gly
305                 310                 315                 320

Phe Gly Leu Gly Pro Glu Tyr Pro Phe Gly Ile Phe Val Ala Gln Asp
                325                 330                 335

Gly Glu Asn Ile Asp His Gly Gln Lys Ala Asn Gln Asn Phe Lys Ile
            340                 345                 350

Val Pro Trp Glu Arg Ile Ala Asp Gln Ile Gly Phe Arg Pro Leu Ala
        355                 360                 365

Asn Glu Gln Val Asp Pro Arg Lys Leu Thr Asp Arg Ser Gly Lys
    370                 375                 380

<210> SEQ ID NO 23
<211> LENGTH: 1724
<212> TYPE: DNA
<213> ORGANISM: Bacillus sp.

<400> SEQUENCE: 23
catatgttga caatttcag cgagttaatg aaagaaacca ataaatcaaa aattagagaa     60
aaacattaat ctgatgcgct ttcatatcgc gttacccgat taatagaata gaaattacaa    120
ataaaacatt gtactaaata ttcattttaa atatttgctc acgtcaattt tttctcttca    180
taaatcctca cattcggaca atcttcacaa aaacttaaca ctgaacttcc tgtatgtatt    240
ttacaattaa agtgcacgtt cataaaagga ggatggaaaa tgaatcattc aaaaacactt    300 tgttaaccg cggcagccgg attgatgctc acatgcggtg cggtttcttc tcaggccaaa    360
cataagctgt ctgatcctta tcattttacc gtgaatgcgg cggcggaaac ggagccggtt    420
gatacagccg gtgatgcagc tgatgatcct gcgatttggc tggaccccaa gaatcctcag    480
aacagcaaat tgatcacaac caataaaaaa tcaggcttag ccgtgtacag cctagaggga    540
aagatgcttc attcctatca taccgggaag ctgaacaatg ttgatatccg atatgatttt    600
ccgttgaacg gaaaaaaagt cgatattgcg gcggcatcca atcggtctga aggaaagaat    660
accattgaga tttacgccat tgacgggaaa acggcacat acaaagcat acgatcca       720 aaccgcccga ttgcatcagc aattgatgaa gtatacggtt tcagcttgta ccacagtcaa    780
aaaacaggaa atattacgc gatggtgaca ggaaaagaag gcgaatttga acaatacgaa    840
ttaaatgcgg ataaaatgg atacatatcc ggcaaaaagg taagggcgtt taaaatgaat    900
```

```
tctcagacag aagggatggc agcagacgat gaatacggca gtctttatat cgcagaagaa    960
gatgaggcca tctggaagtt cagcgctgag ccggacggcg gcagtaacgg aacggttatc   1020
gatcgtgccg atggcaggca tttaacccct gatattgaag gactgacgat ttactacgct   1080
gctgacggga aaggctatct gcttgcctca agccagggta cagcagcta tgcgatttat    1140
gaaagacagg gacagaacaa atatgttgcg gactttcaga taacagacgg gcctgaaaca   1200
gacggcacaa gcgatacaga cggaattgac gttctgggtt tcgggctggg gcctgaatat   1260
ccgttcggtc tttttgtcgc acaggacgga gagaatatag atcacggcca aaaggccaat   1320
caaaatttta aaatggtgcc atgggaaaga atcgctgata aaatcggctt tcacccgcag   1380
gtcaataaac aggtcgaccc gagaaaaatg accgacagaa gcggaaaata acatgaaaa   1440
aagcagctta tccaagctgc tttttgatgt gaagagcgtt tcatgagaaa gtcttggaac   1500
ggatagccgt aagcacagcc ggcagccggt catacgtgta cgccggtact gtctcttgat   1560
aattaagcgc cgcgatttgt ttacgttcac ccgggtttgt catataaaaa tggatcttat   1620
ccggaaaatc cgcaaacccg ctgtaagaaa caaatgttga aaacggggc gcgggagaaa    1680
ggtctgtcag ctgaaaggcc tgacaagccg caatgtctaa gctt                   1724
```

<210> SEQ ID NO 24
<211> LENGTH: 383
<212> TYPE: PRT
<213> ORGANISM: Bacillus sp.

<400> SEQUENCE: 24

```
Met Asn His Ser Lys Thr Leu Leu Leu Thr Ala Ala Gly Leu Met
 1               5                  10                  15

Leu Thr Cys Gly Ala Val Ser Ser Gln Ala Lys His Lys Leu Ser Asp
                20                  25                  30

Pro Tyr His Phe Thr Val Asn Ala Ala Ala Glu Thr Glu Pro Val Asp
            35                  40                  45

Thr Ala Gly Asp Ala Ala Asp Asp Pro Ala Ile Trp Leu Asp Pro Lys
        50                  55                  60

Asn Pro Gln Asn Ser Lys Leu Ile Thr Thr Asn Lys Lys Ser Gly Leu
 65                  70                  75                  80

Ala Val Tyr Ser Leu Glu Gly Lys Met Leu His Ser Tyr His Thr Gly
                 85                  90                  95

Lys Leu Asn Asn Val Asp Ile Arg Tyr Asp Phe Pro Leu Asn Gly Lys
            100                 105                 110

Lys Val Asp Ile Ala Ala Ala Ser Asn Arg Ser Glu Gly Lys Asn Thr
        115                 120                 125

Ile Glu Ile Tyr Ala Ile Asp Gly Lys Asn Gly Thr Leu Gln Ser Ile
    130                 135                 140

Thr Asp Pro Asn Arg Pro Ile Ala Ser Ala Ile Asp Glu Val Tyr Gly
145                 150                 155                 160

Phe Ser Leu Tyr His Ser Gln Lys Thr Gly Lys Tyr Tyr Ala Met Val
                165                 170                 175

Thr Gly Lys Glu Gly Glu Phe Glu Gln Tyr Glu Leu Asn Ala Asp Lys
            180                 185                 190

Asn Gly Tyr Ile Ser Gly Lys Lys Val Arg Ala Phe Lys Met Asn Ser
        195                 200                 205

Gln Thr Glu Gly Met Ala Ala Asp Asp Glu Tyr Gly Ser Leu Tyr Ile
    210                 215                 220

Ala Glu Glu Asp Glu Ala Ile Trp Lys Phe Ser Ala Glu Pro Asp Gly
```

```
                225                 230                 235                 240
Gly Ser Asn Gly Thr Val Ile Asp Arg Ala Asp Gly Arg His Leu Thr
                245                 250                 255
Pro Asp Ile Glu Gly Leu Thr Ile Tyr Tyr Ala Ala Asp Gly Lys Gly
                260                 265                 270
Tyr Leu Leu Ala Ser Ser Gln Gly Asn Ser Ser Tyr Ala Ile Tyr Glu
                275                 280                 285
Arg Gln Gly Gln Asn Lys Tyr Val Ala Asp Phe Gln Ile Thr Asp Gly
                290                 295                 300
Pro Glu Thr Asp Gly Thr Ser Asp Thr Asp Gly Ile Ala Val Leu Gly
305                 310                 315                 320
Phe Gly Leu Gly Pro Glu Tyr Pro Phe Gly Leu Phe Val Ala Gln Asp
                325                 330                 335
Gly Glu Asn Ile Asp His Gly Gln Lys Ala Asn Gln Asn Phe Lys Met
                340                 345                 350
Val Pro Trp Glu Arg Ile Ala Asp Lys Ile Gly Phe His Pro Gln Val
                355                 360                 365
Asn Lys Gln Val Asp Pro Arg Lys Met Thr Asp Arg Ser Gly Lys
                370                 375                 380

<210> SEQ ID NO 25
<211> LENGTH: 9
<212> TYPE: PRT
<213> ORGANISM: Bacillus sp.

<400> SEQUENCE: 25

Asp Ala Ala Asp Asp Pro Ala Ile Trp
1               5

<210> SEQ ID NO 26
<211> LENGTH: 7
<212> TYPE: PRT
<213> ORGANISM: Bacillus sp.

<400> SEQUENCE: 26

Gly Glu Phe Glu Gln Tyr Glu
1               5

<210> SEQ ID NO 27
<211> LENGTH: 19
<212> TYPE: PRT
<213> ORGANISM: Bacillus subtilis

<400> SEQUENCE: 27

Asp Ala Ala Asp Asp Pro Ala Ile Trp Val His Glu Lys His Pro Glu
1               5                   10                  15

Lys Ser Lys

<210> SEQ ID NO 28
<211> LENGTH: 19
<212> TYPE: PRT
<213> ORGANISM: Bacillus subtilis

<400> SEQUENCE: 28

Asp Ala Ala Asp Asp Pro Ala Ile Trp Leu Asp Pro Lys Thr Pro Gln
1               5                   10                  15

Asn Ser Lys

<210> SEQ ID NO 29
```

```
<211> LENGTH: 19
<212> TYPE: PRT
<213> ORGANISM: Bacillus subtilis

<400> SEQUENCE: 29

Asp Ala Ala Asp Asp Pro Ala Ile Trp Leu Asp Pro Lys Thr Pro Gln
 1               5                  10                  15

Asn Ser Lys

<210> SEQ ID NO 30
<211> LENGTH: 17
<212> TYPE: PRT
<213> ORGANISM: Bacillus subtilis

<400> SEQUENCE: 30

Ala Phe Tyr Ala Leu Val Thr Gly Lys Gln Gly Glu Phe Glu Gln Tyr
 1               5                  10                  15

Glu

<210> SEQ ID NO 31
<211> LENGTH: 17
<212> TYPE: PRT
<213> ORGANISM: Bacillus subtilis

<400> SEQUENCE: 31

Lys Tyr Tyr Ala Met Val Thr Gly Lys Glu Gly Glu Phe Glu Gln Tyr
 1               5                  10                  15

Glu

<210> SEQ ID NO 32
<211> LENGTH: 17
<212> TYPE: PRT
<213> ORGANISM: Bacillus subtilis

<400> SEQUENCE: 32

Lys Tyr Tyr Ala Met Val Thr Gly Lys Glu Gly Glu Phe Glu Gln Tyr
 1               5                  10                  15

Glu
```